United States Patent
Lee et al.

(10) Patent No.: US 12,134,793 B2
(45) Date of Patent: Nov. 5, 2024

(54) RECOMBINANT MICROORGANISM HAVING INCREASED ABILITY TO PRODUCE HYDROPHOBIC MATERIAL AND CELL-MEMBRANE ENGINEERING METHOD FOR PREPARATION THEREOF

(71) Applicant: KOREA ADVANCED INSTITUTE OF SCIENCE AND TECHNOLOGY, Daejeon (KR)

(72) Inventors: Sang Yup Lee, Daejeon (KR); Dongsoo Yang, Daejeon (KR); Seon Young Park, Daejeon (KR)

(73) Assignee: KOREA ADVANCED INSTITUTE OF SCIENCE AND TECHNOLOGY, Daejeon (KR)

( * ) Notice: Subject to any disclaimer, the term of this patent is extended or adjusted under 35 U.S.C. 154(b) by 0 days.

(21) Appl. No.: 17/515,614

(22) Filed: Nov. 1, 2021

(65) Prior Publication Data
US 2022/0136028 A1    May 5, 2022

(30) Foreign Application Priority Data

Nov. 2, 2020    (KR) ........................ 10-2020-0144521

(51) Int. Cl.
| | | |
|---|---|---|
| C12P 23/00 | (2006.01) | |
| C07K 14/245 | (2006.01) | |
| C12N 1/20 | (2006.01) | |
| C12N 9/04 | (2006.01) | |
| C12N 9/10 | (2006.01) | |
| C12N 9/90 | (2006.01) | |
| C12P 17/16 | (2006.01) | |

(52) U.S. Cl.
CPC ............ *C12P 23/00* (2013.01); *C07K 14/245* (2013.01); *C12N 1/20* (2013.01); *C12N 9/0006* (2013.01); *C12N 9/1029* (2013.01); *C12N 9/1051* (2013.01); *C12N 9/90* (2013.01); *C12P 17/165* (2013.01); *C12Y 101/01336* (2015.07); *C12Y 204/01044* (2013.01); *C12Y 204/01129* (2013.01); *C12Y 501/0302* (2013.01)

(58) Field of Classification Search
CPC .................. C12P 23/00; C12P 17/165; C12Y 101/01336; C12Y 204/01044; C12Y 204/01129; C12Y 501/0302; C07K 14/245; C12N 1/20; C12N 9/0006; C12N 9/1029; C12N 9/1051; C12N 9/90
See application file for complete search history.

(56) References Cited

FOREIGN PATENT DOCUMENTS

| EP | 0307247 B1 | 3/1989 |
|---|---|---|
| WO | 9108291 A2 | 6/1991 |
| WO | 2017097828 A1 | 6/2017 |
| WO | 2020004936 A1 | 1/2020 |

OTHER PUBLICATIONS

Shin, Jonghyeok et al. "Endocytosing Escherichia coli as a Whole-Cell Biocatalyst of Fatty Acids." ACS synthetic biology 8.5 (2019): 1055-1066. Web. (Year: 2019).*
Meier-Dieter U, Starman R, Barr K, Mayer H, Rick PD. Biosynthesis of enterobacterial common antigen in Escherichia coli. Biochemical characterization of Tn10 insertion mutants defective in enterobacterial common antigen synthesis. J Biol Chem. Aug. 15, 1990;265(23):13490-7. PMID: 2166030. (Year: 1990).*
Shibayama K, Ohsuka S, Tanaka T, Arakawa Y, Ohta M. Conserved structural regions involved in the catalytic mechanism of Escherichia coli K-12 WaaO (Rfal). J Bacteriol. Oct. 1998;180(20):5313-8. doi: 10.1128/JB.180.20.5313-5318.1998. PMID: 9765561; PMCID: PMC107578. (Year: 1998).*
Wang, J.; Ma, W.; Wang, Z.; Li, Y.; Wang, X. Construction and Characterization of an Escherichia coli Mutant Producing Kdo2-Lipid A. Mar. Drugs 2014, 12, 1495-1511. https://doi.org/10.3390/md12031495 (Year: 2014).*
Matsuoka S. Biological functions of glucolipids in Bacillus subtilis. Genes Genet Syst. 2017;92(5):217-221. doi: 10.1266/ggs.17-00017. Epub Oct. 6, 2017. PMID: 28993557. (Year: 2017).* French, Shawn et al. "Bacteria Getting into Shape: Genetic Determinants of E. coli Morphology." mBio 8.2 (2017): n. pag. Web. (Year: 2017).*
Becker J, Wittmann C. Systems metabolic engineering of Escherichia coli for the heterologous production of high value molecules-a veteran at new shores. Curr Opin Biotechnol. Dec. 2016;42:178-188. doi: 10.1016/j.copbio.2016.05.004. Epub Aug. 8, 2016. PMID: 27513555. (Year: 2016).*

(Continued)

*Primary Examiner* — Louise W Humphrey
*Assistant Examiner* — John Paul Selwanes
(74) *Attorney, Agent, or Firm* — HULTQUIST, PLLC; Steven J. Hultquist

(57) ABSTRACT

Disclosed are a recombinant microorganism for producing a hydrophobic material, which is subjected to cell-membrane engineering in order to be imparted with at least one characteristic among an increase in a cell-membrane area, an increase in formation and secretion of an outer membrane vesicle, and an increase in formation of an inner membrane vesicle, and a cell-membrane engineering method for preparation thereof, whereby an insoluble hydrophobic material can be produced with high efficiency, the recombinant microorganism for high-efficiency production of carotenoids or violacein analogues is useful for producing natural pigments, antioxidants, antibiotics, cosmetic additives, anticancer agents, food additives, or nutritional supplements, and the natural pigment production technology developed herein achieves a great increase in production ability. Therefore, the present invention is effective at preparing a recombinant strain for efficient production of a variety of industrially and medically useful metabolites and at establishing an efficient preparation method.

8 Claims, 35 Drawing Sheets
Specification includes a Sequence Listing.

(56) References Cited

OTHER PUBLICATIONS

Shen, H-J, et al., "Dynamic control of the mevalonate pathway expressio for improved zeaxanthin production in *Escherichia coli* and comparative proteome analysis", Metabolic Engineering, 2016, pp. 180-190, vol. 38, Publisher: Elsevier.

Yang, D., et al., "Production of Rainbow Colorants by Metabolically Engineered *Escherichia coli*", Advanced Science, 2021, p. 2100743; 10.1002/advs.202100743, vol. 8, No. 13.

Choi, H.S., et al., "In Silico Indentification of Gene Amplification Targets for Improvement of Lycopene Production", Applied and Environmental Microbiology, 2010, pp. 3097-3105, vol. 76, No. 10, Publisher: American Society for Microbiology.

Kole, R., et al., "RNA therapeutics: Beyond RNA interference and antisense oligonucleotides", Nat Rev Drug Discov, Feb. 5, 2016, pp. 125-140, vol. 11, No. 2, Publisher: HHS Public Access.

Ma, T., et al., "Lipid engineering combined with systematic metabolic engineering of *Saccharomyces cerevisiae* for high-yield production of lycopene", Metabolic Engineering, 2018, pp. 134-142, vol. 52, Publisher: Elsevier.

Na, D., et al., "Metabolic engineering of *Excherichia coli* using synthetic small regulatory RNAs", Nature Biotechnology, 2012, pp. 170-176, vol. 31, No. 2, Publisher: NPG.

Park, S.Y., et al., "Metabolic engineering of *Escherichia coli* for high-level astaxanthin production with high productivity", Metabolic Engineering, 2018, pp. 105-115, vol. 49, Publisher: Elsevier.

Phylactou, L.A., et al., "Ribozymes as therapeutic tools for genetic disease", Human Molecular Genetics, 1998, pp. 1649-1653, vol. 7, No. 10, Publisher: Oxford University Press.

Wu, T., et al., "Membrane engineering—a novel strategy to enhance the production and accumulation of -carotene in *Echerichia coli*", Metabolic Engineering, 2017, Page(s) http://dx.doi.org/10.1016/j.ymben.2017.07.001, Publisher: Elsevier.

Office Action Issued in Korean Patent Application No. 10-2021-0115493 on Aug. 9, 2023.

English Translation of Office Action Issued in Korean Patent Application No. 10-2021-0115493 on Aug. 9, 2023.

Pichler, H., et al., "Modifications of membrane lipid compositions in single-celled organisms—From basics to applications", Methods, 2018, pp. 50-65, vol. 147, Publisher: Elsevier.

Issue of PESR in European Patent Application No. 23154792.8 on Jun. 7, 2023.

Kulp, A.J., et al., "Genome-Wide Assessment of Outer Membrane Vesicle Production in *Escherichia coli*", PLoS One, 2015, e0139200; doi:10.1371/journal.pone.0139200, vol. 10, No. 9.

Wu, T., et al., Sonthetic Biology, 2019, pp. 1037-1046, vol. 8, Publisher: ACS.

\* cited by examiner

[Figure 1]
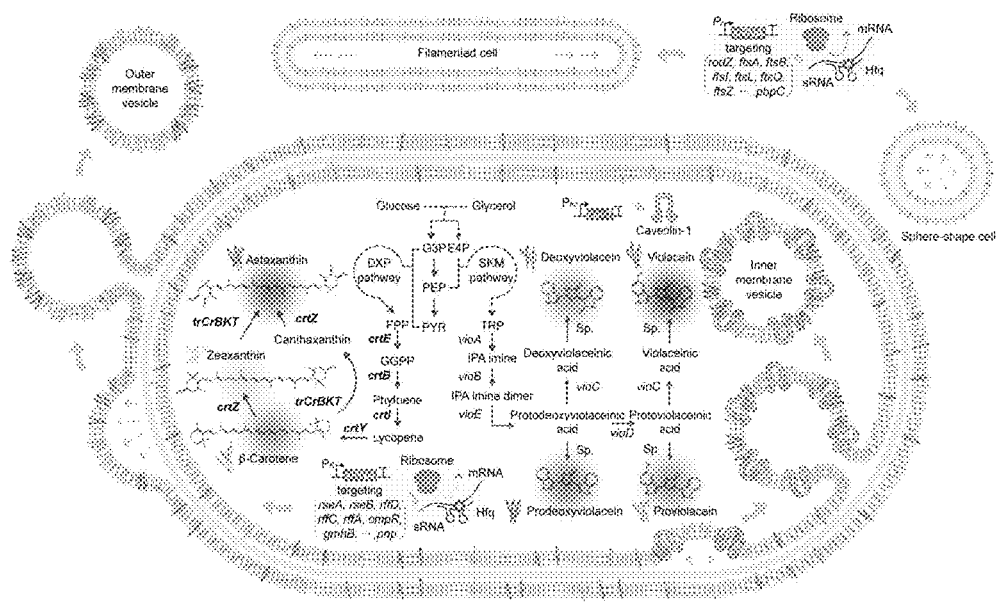
[Figure 2a]
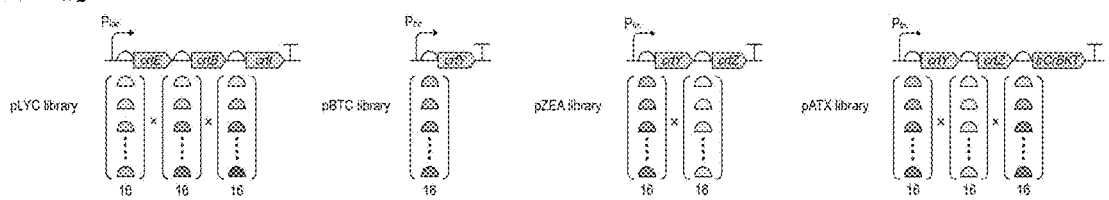

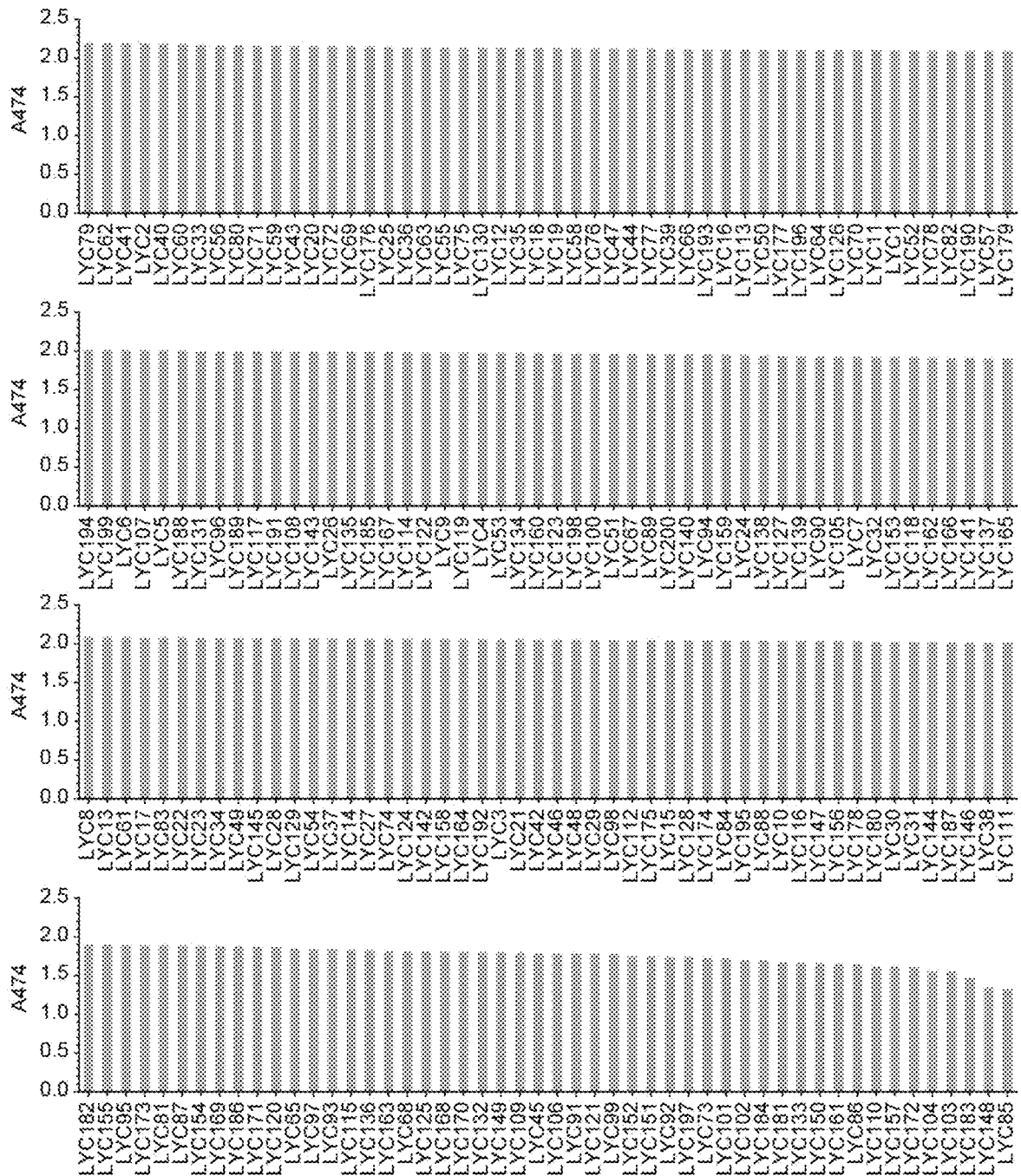
[Figure 2b]

[Figure 2c]
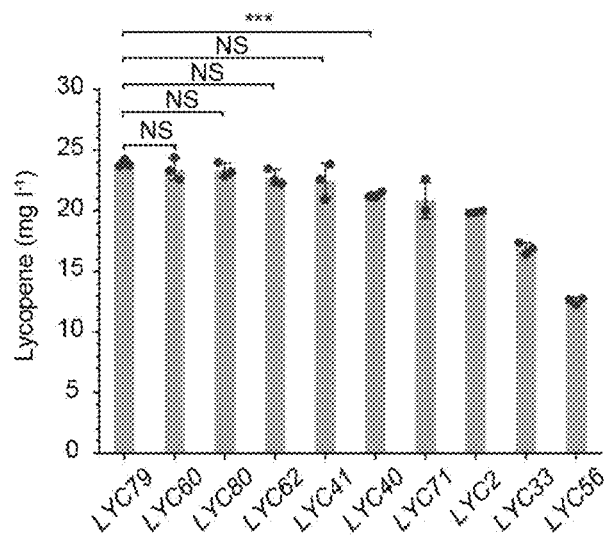
[Figure 2d]
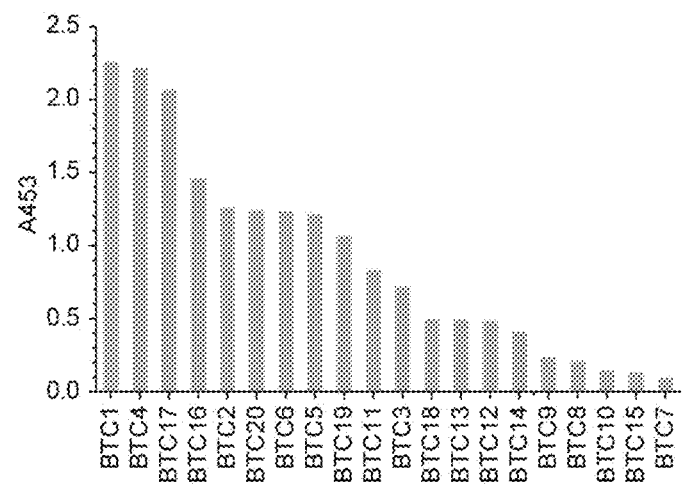

[Figure 2e]
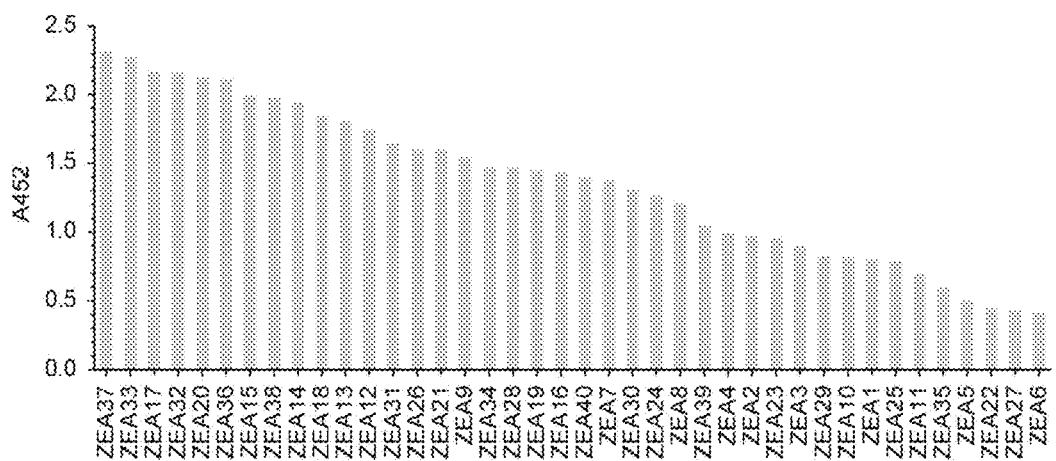

[Figure 2f]
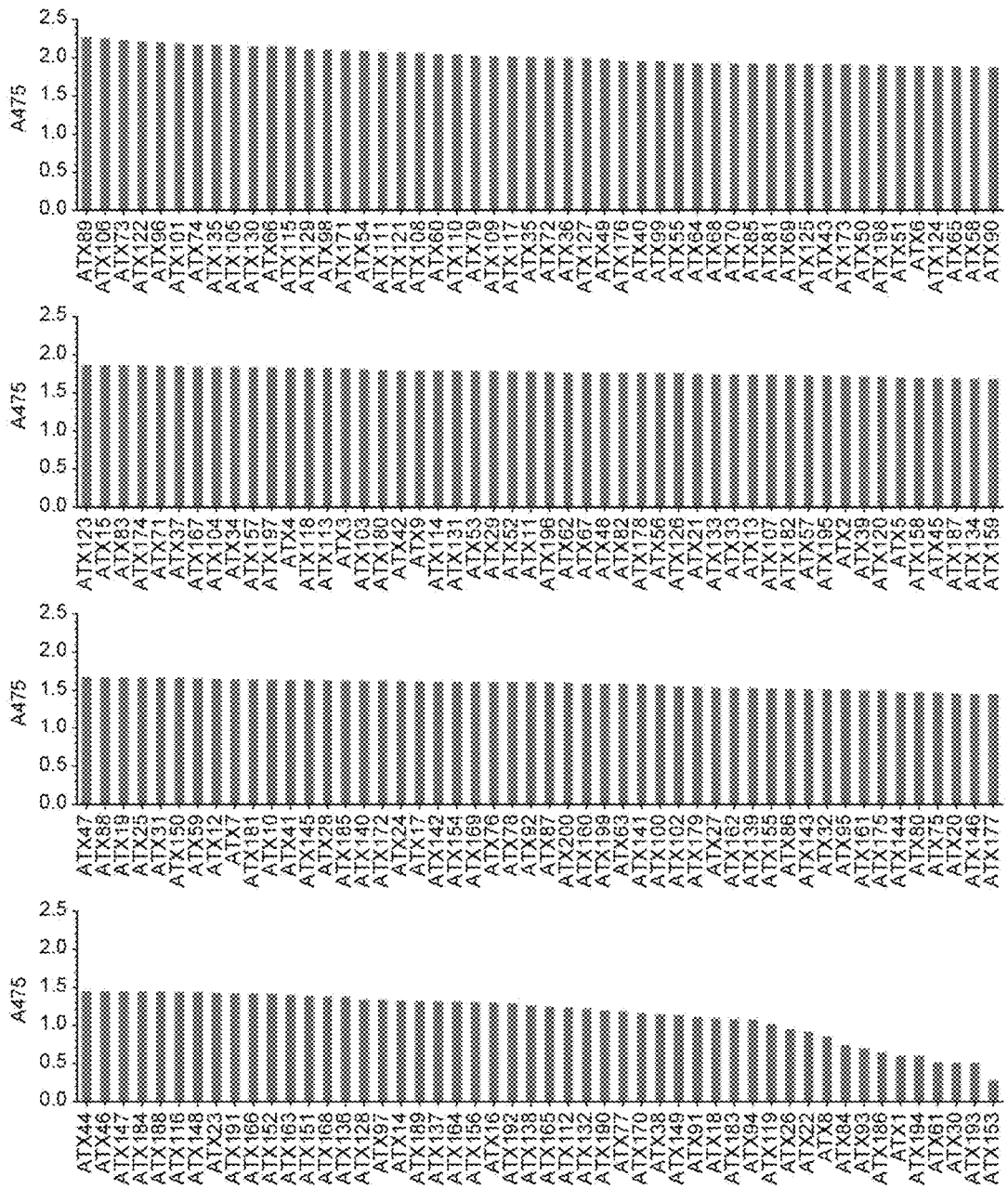

[Figure 2g]
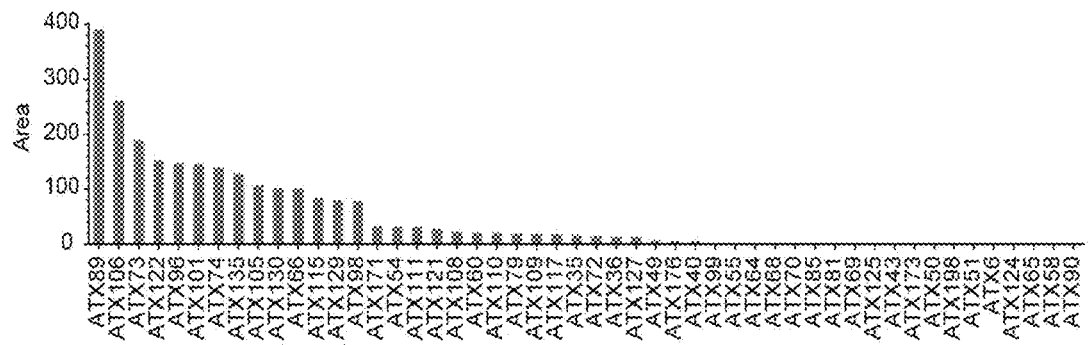
[Figure 2h]
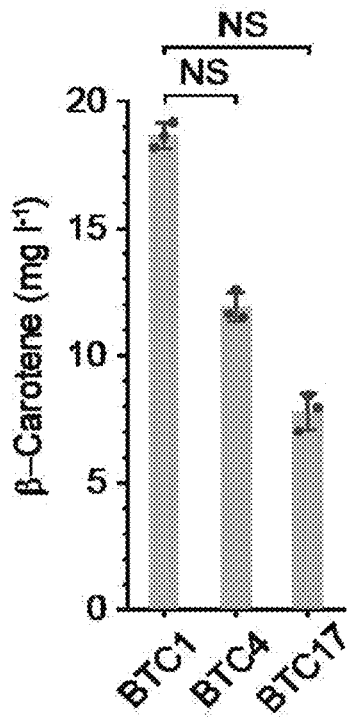

【Figure 2i】
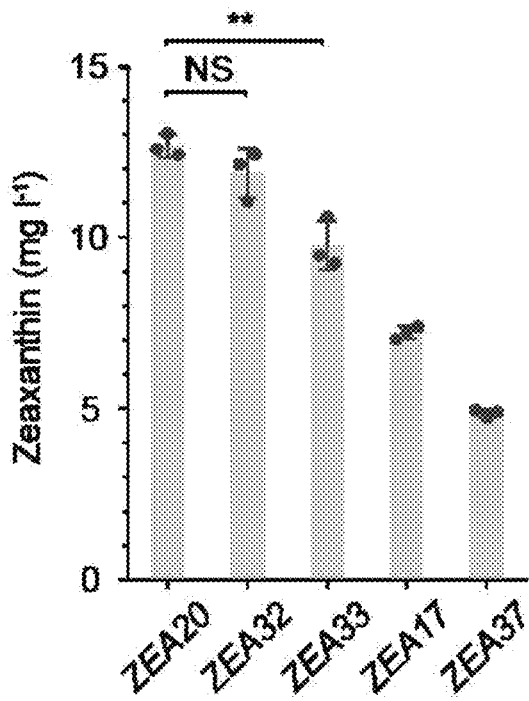
【Figure 2j】
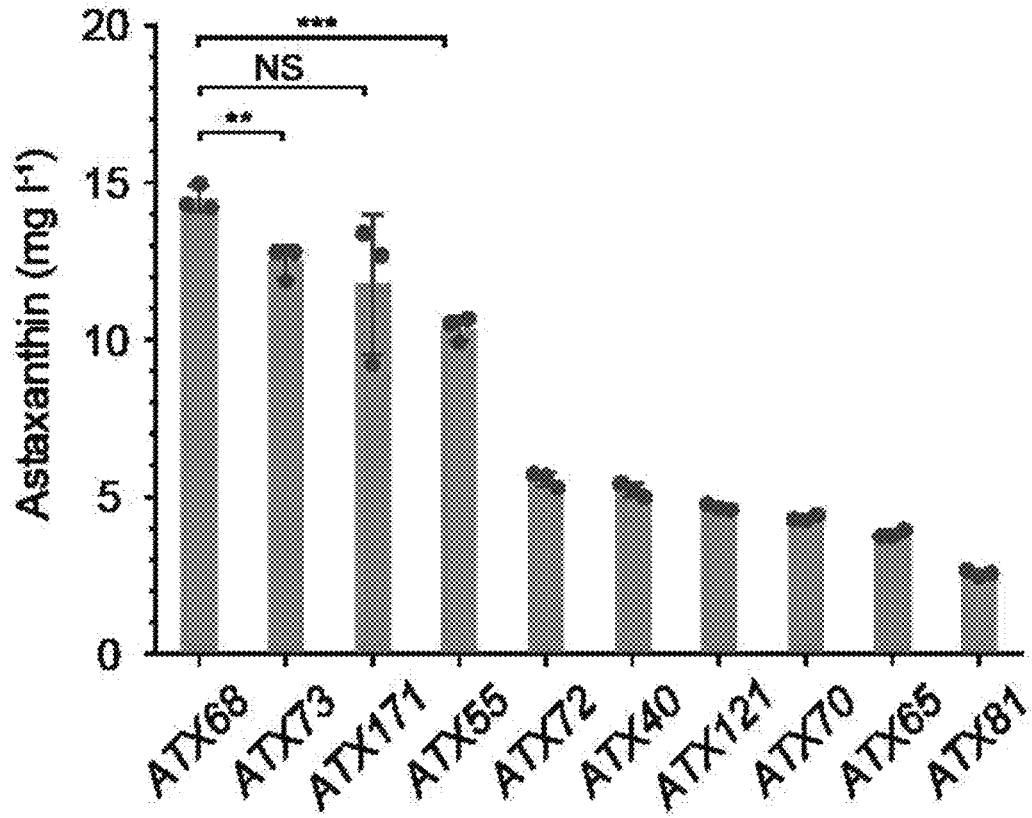

【Figure 3a】
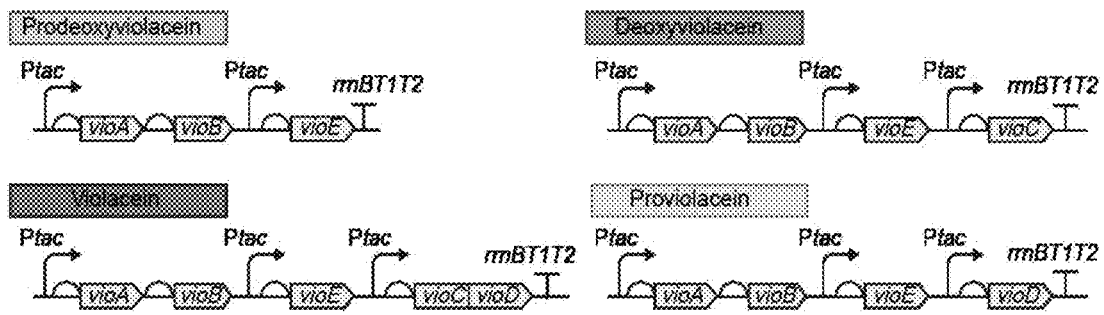
【Figure 3b】
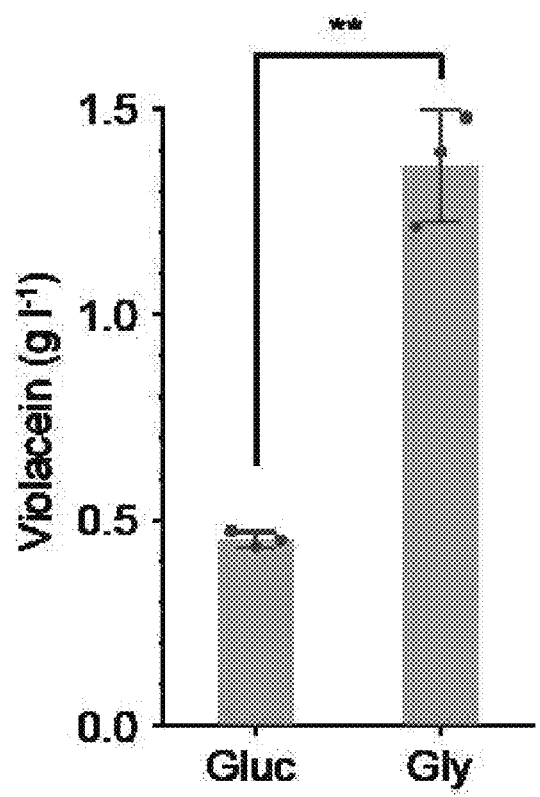

[Figure 3c]
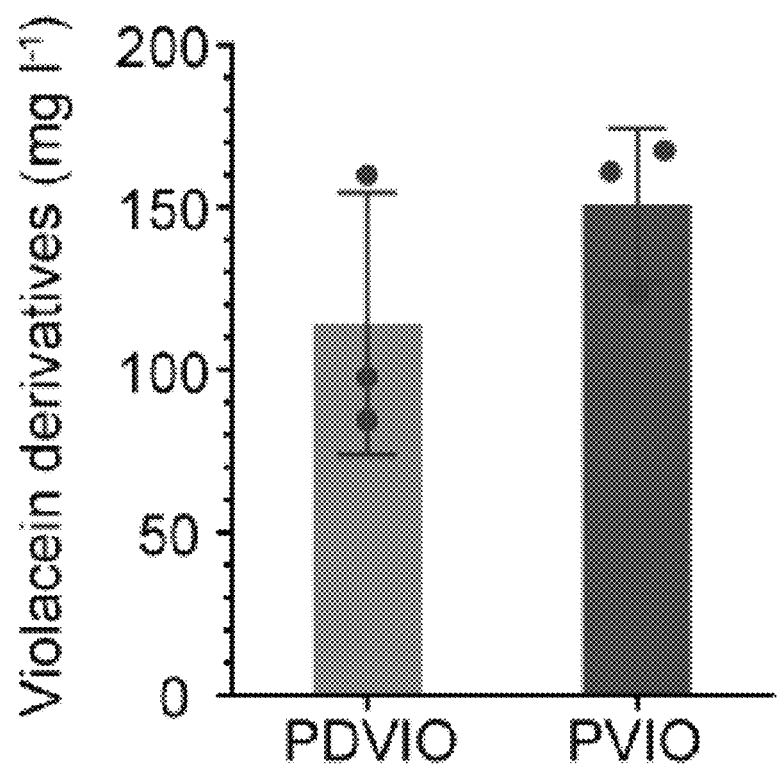

[Figure 3d]
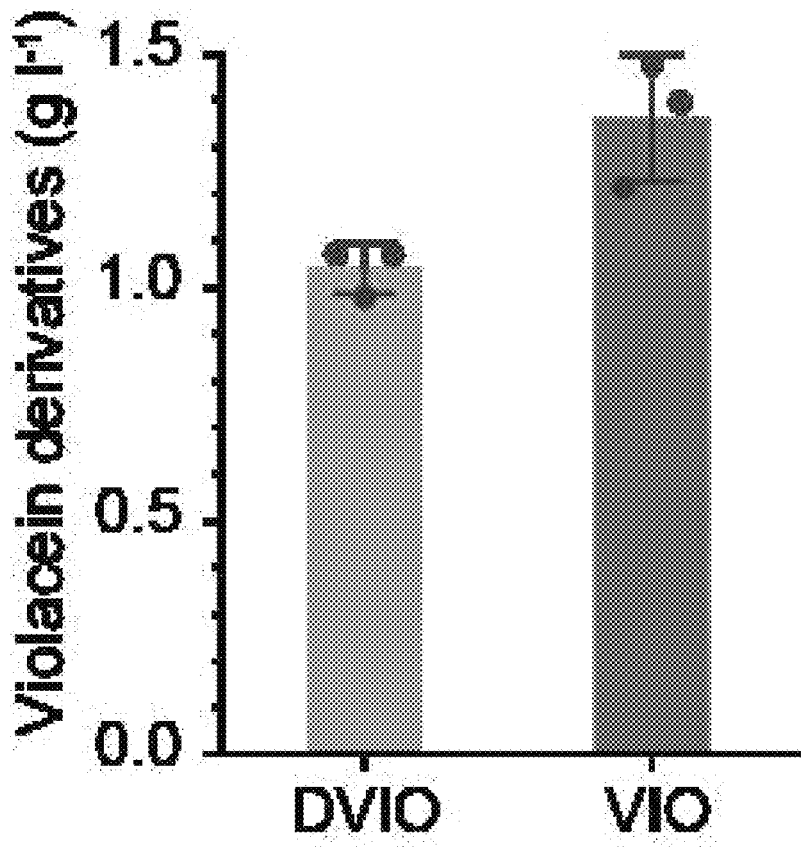
[Figure 3e]
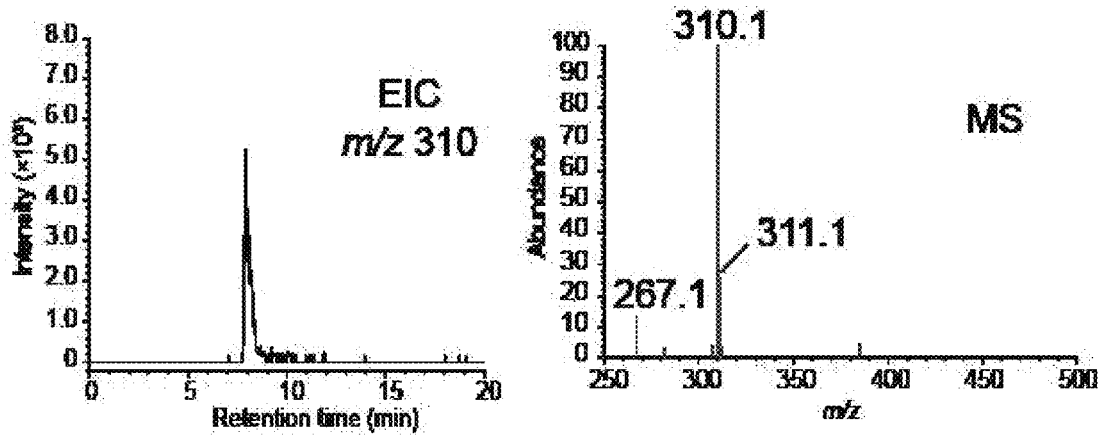

[Figure 3f]
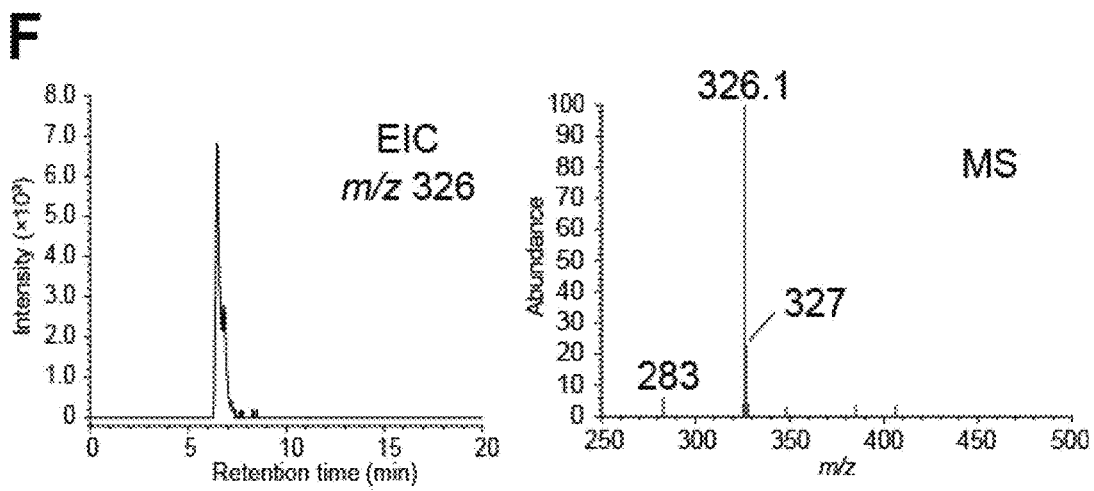
[Figure 3g]
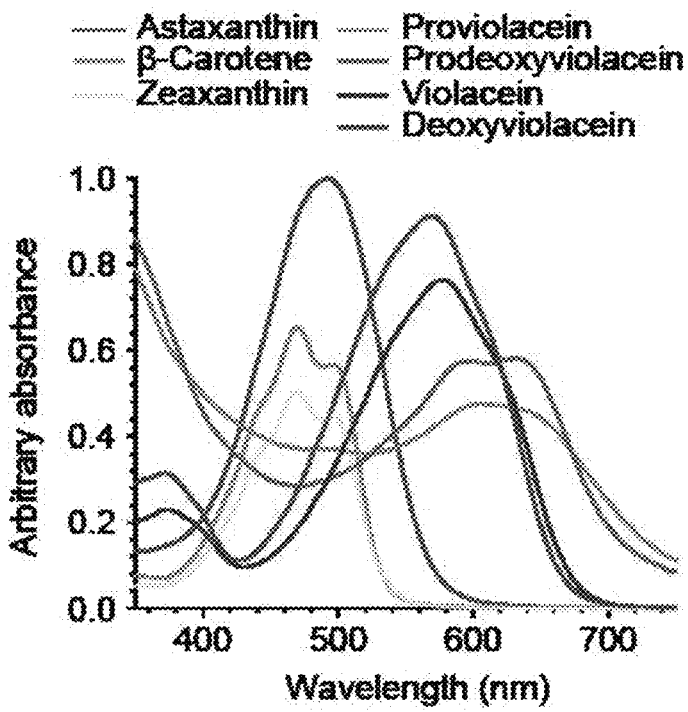

[Figure 4a]
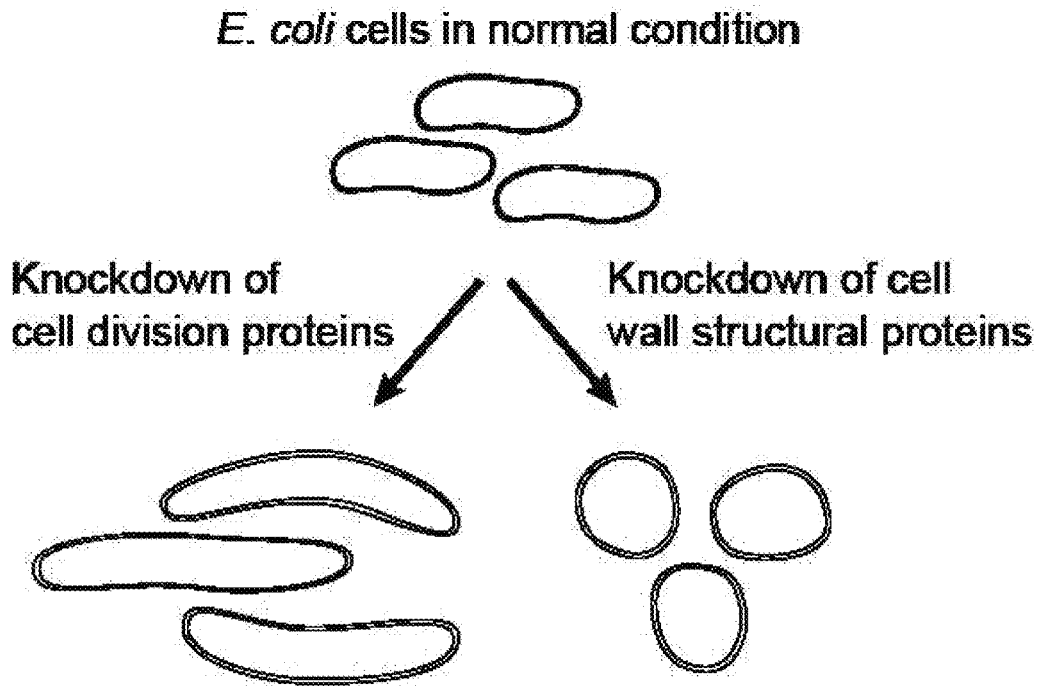
[Figure 4b]
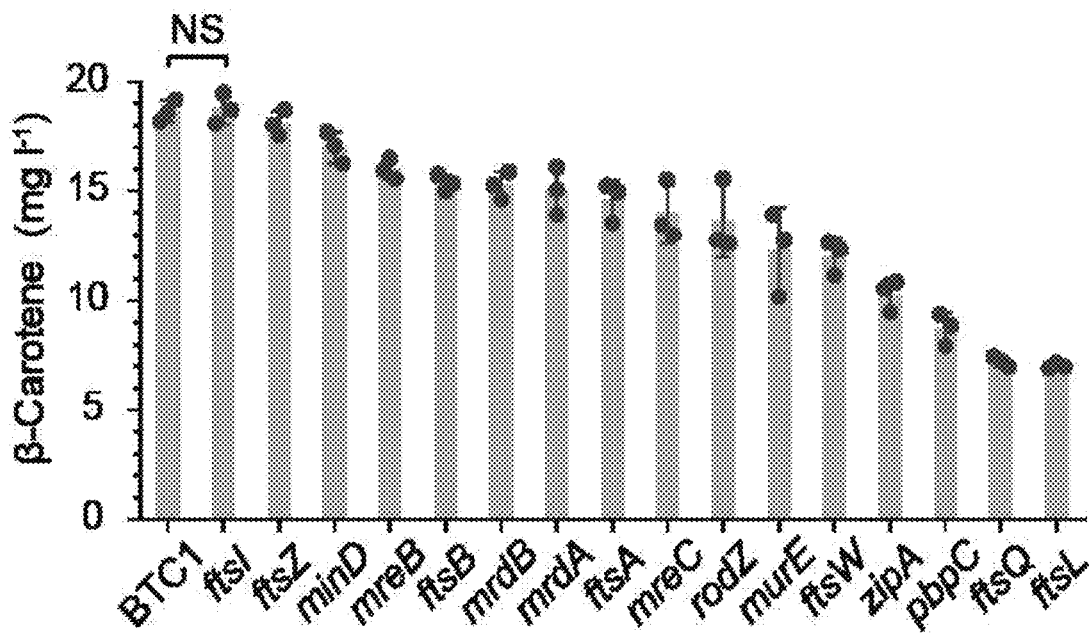

[Figure 4c]
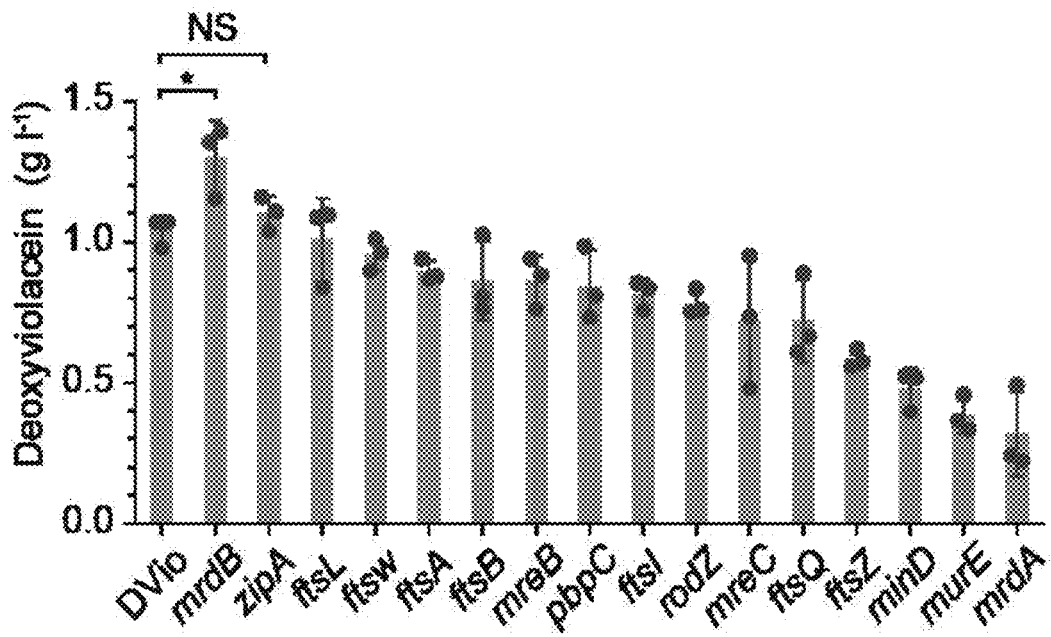
[Figure 4d]
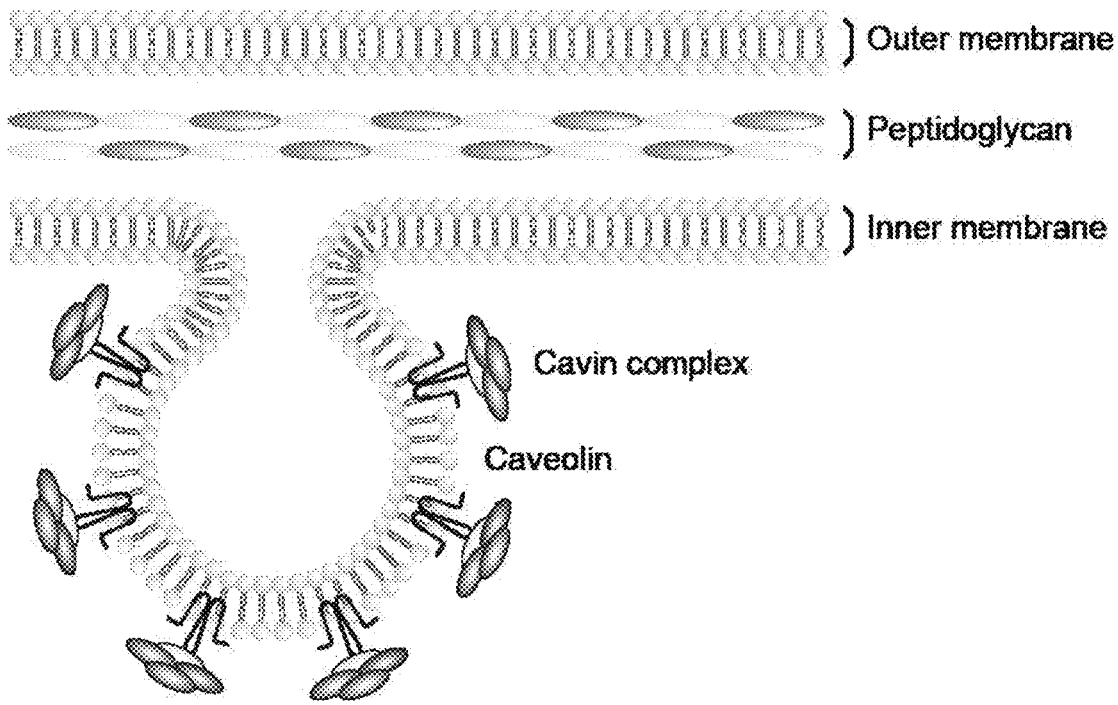

【Figure 4e】
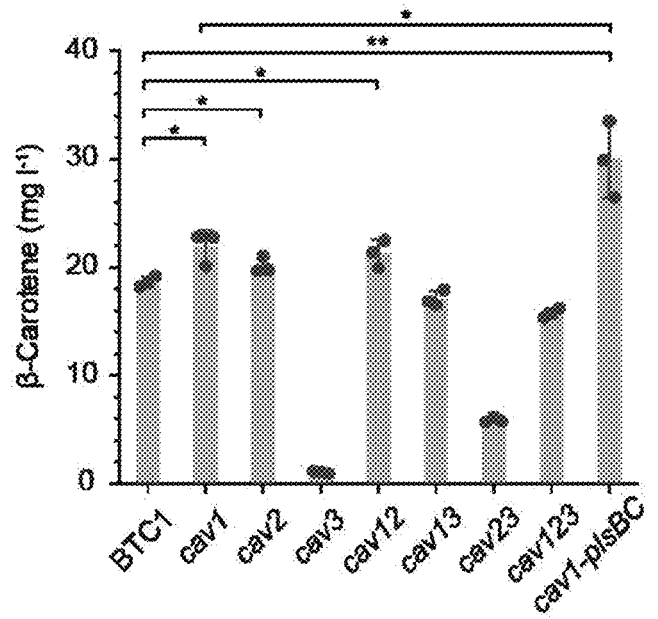
【Figure 4f】
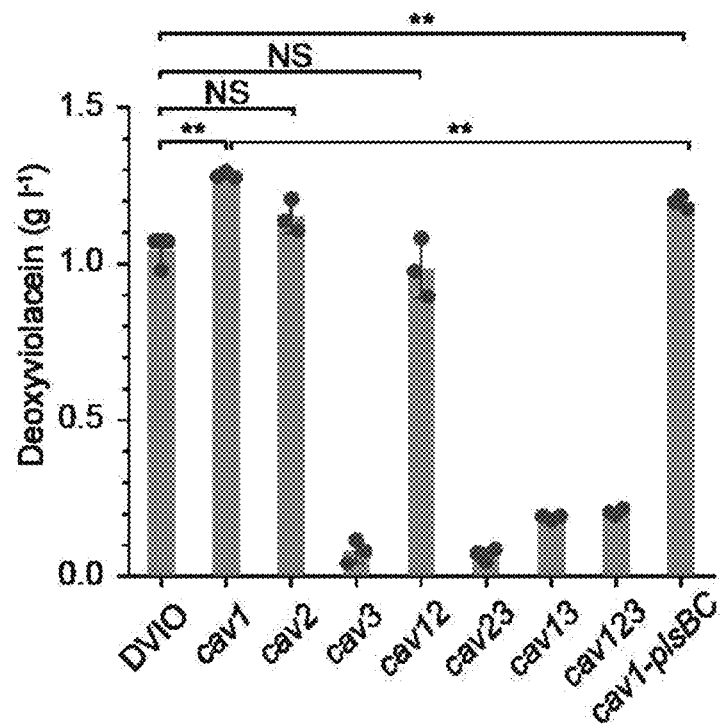

[Figure 4g]
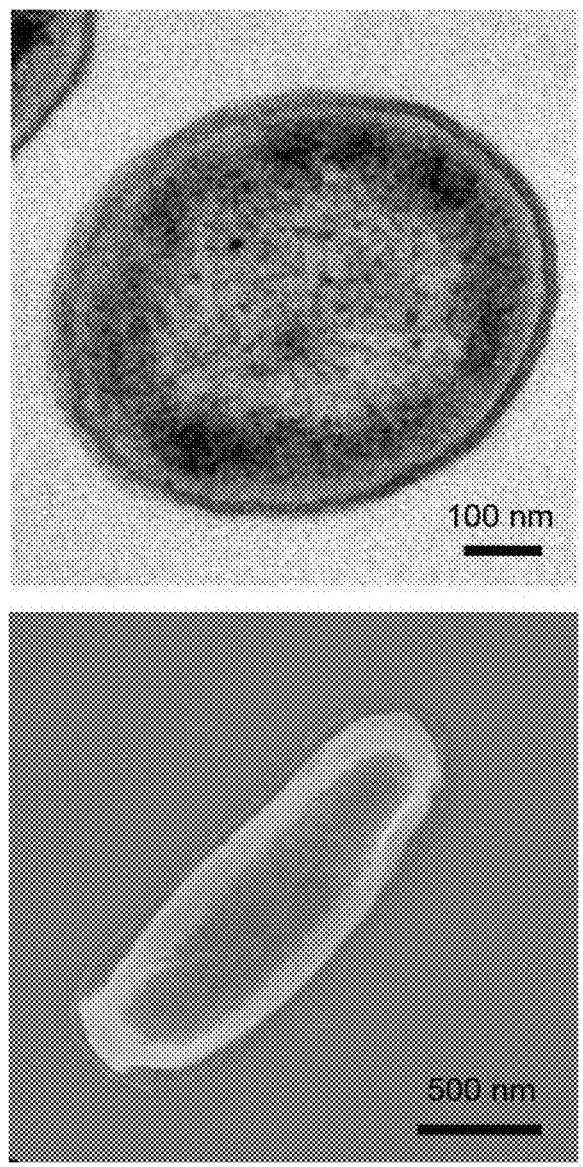

[Figure 4h]
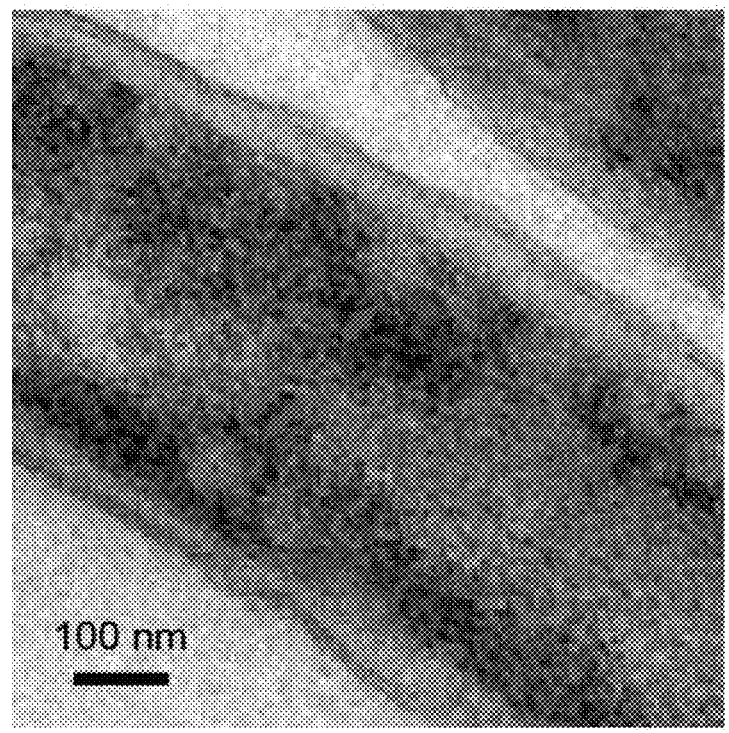
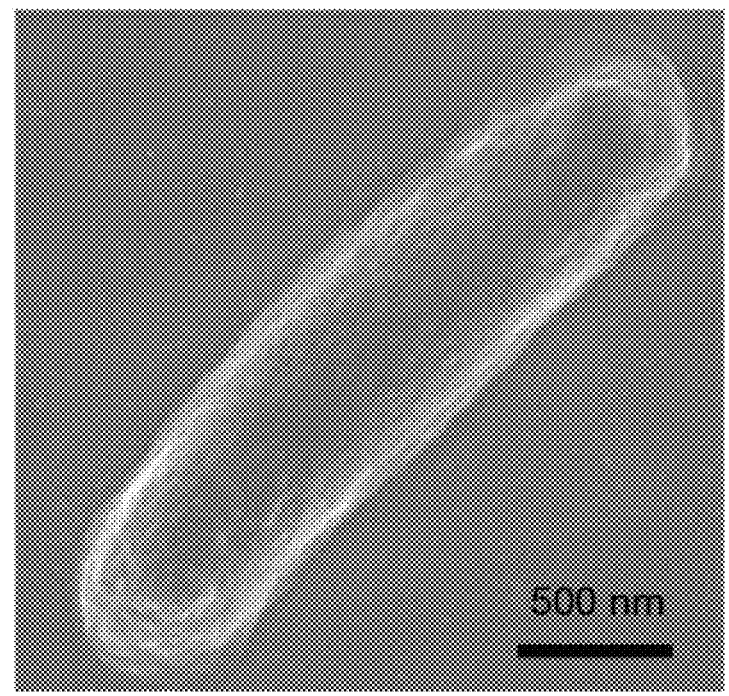

[Figure 4i]
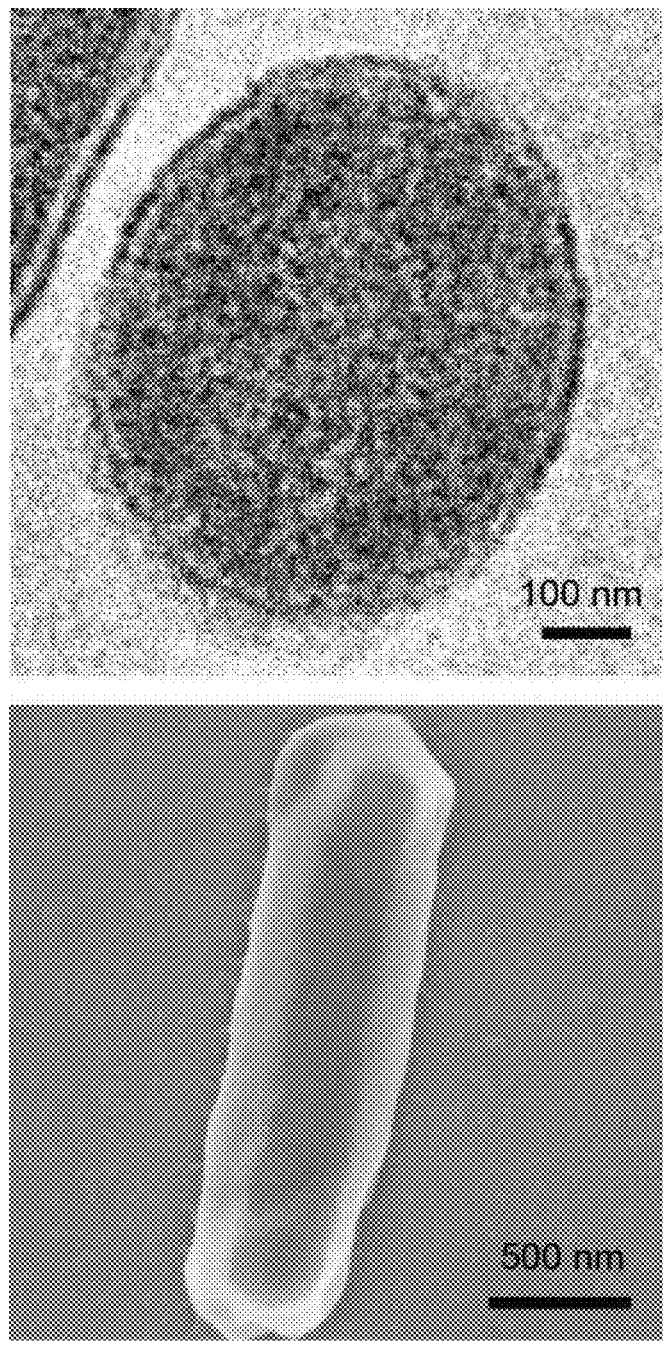

[Figure 4j]
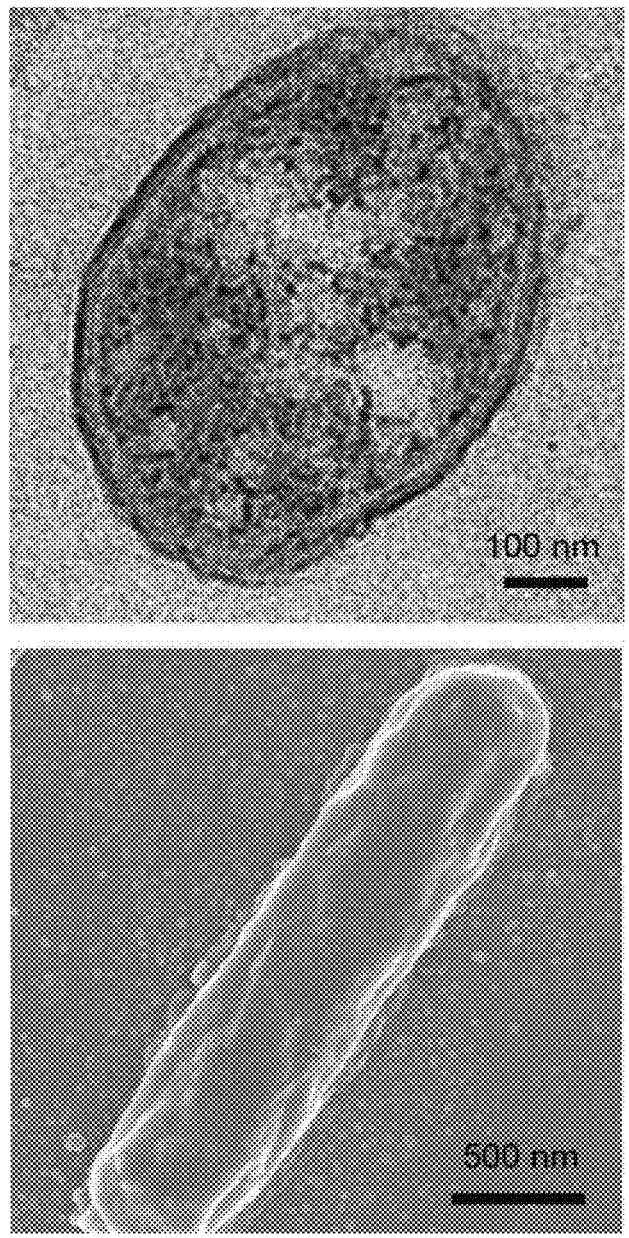

[Figure 5a]
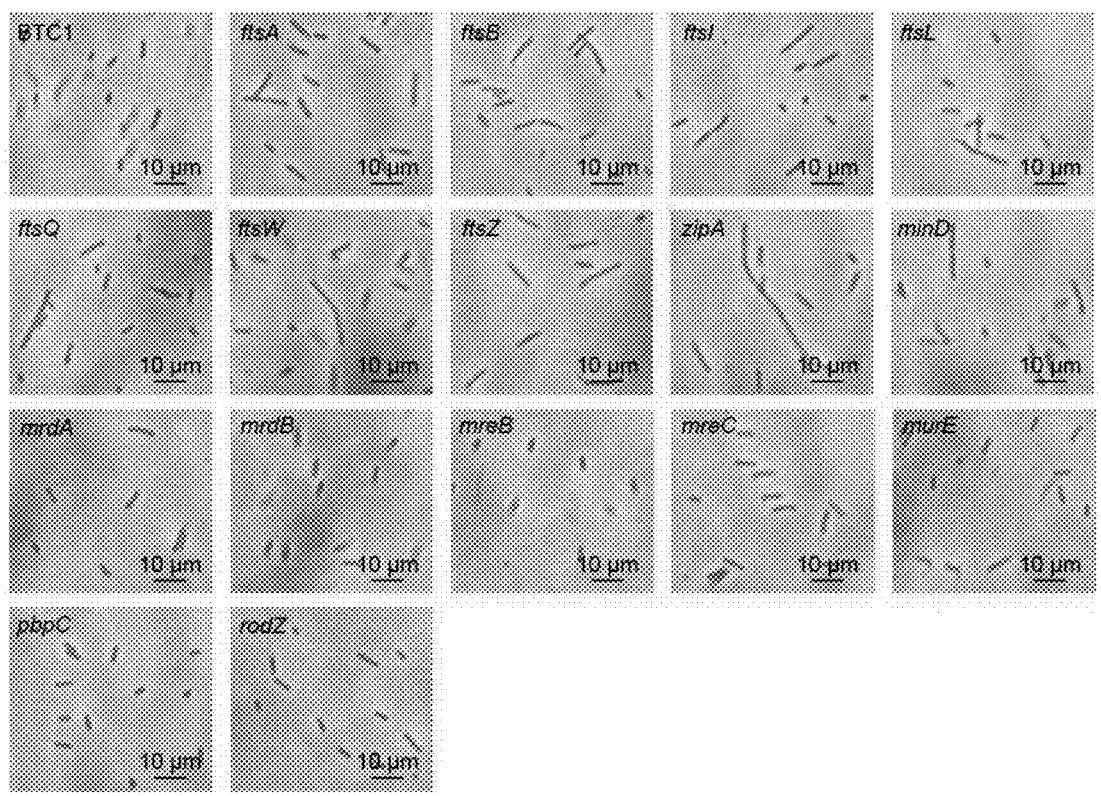

[Figure 5b]
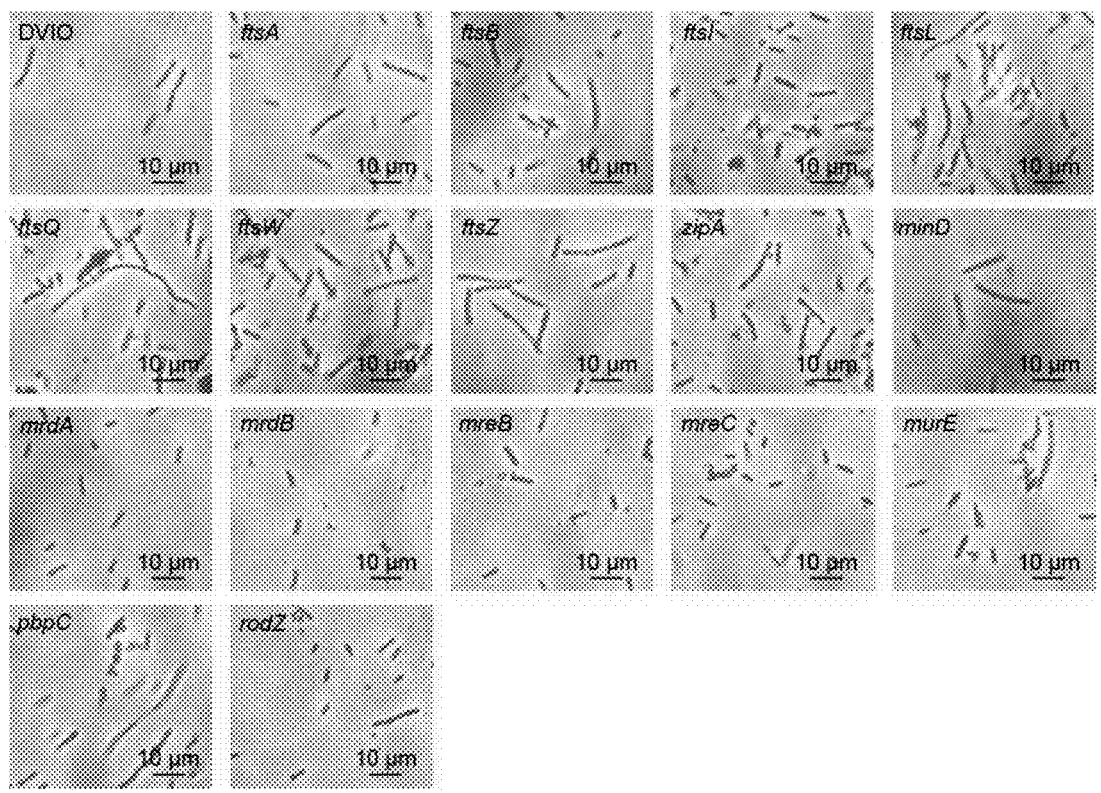

[Figure 6a]
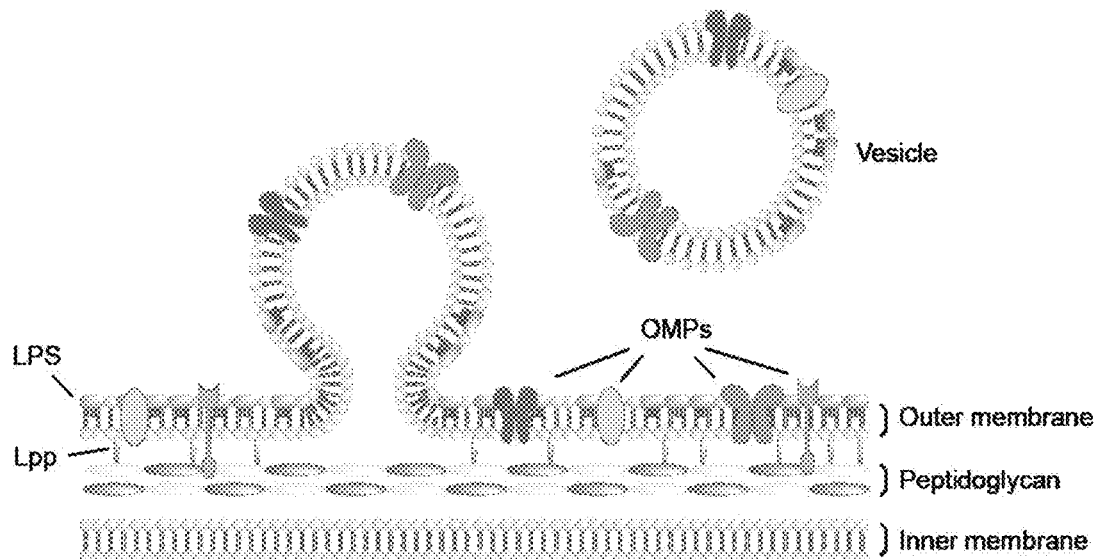
[Figure 6b]
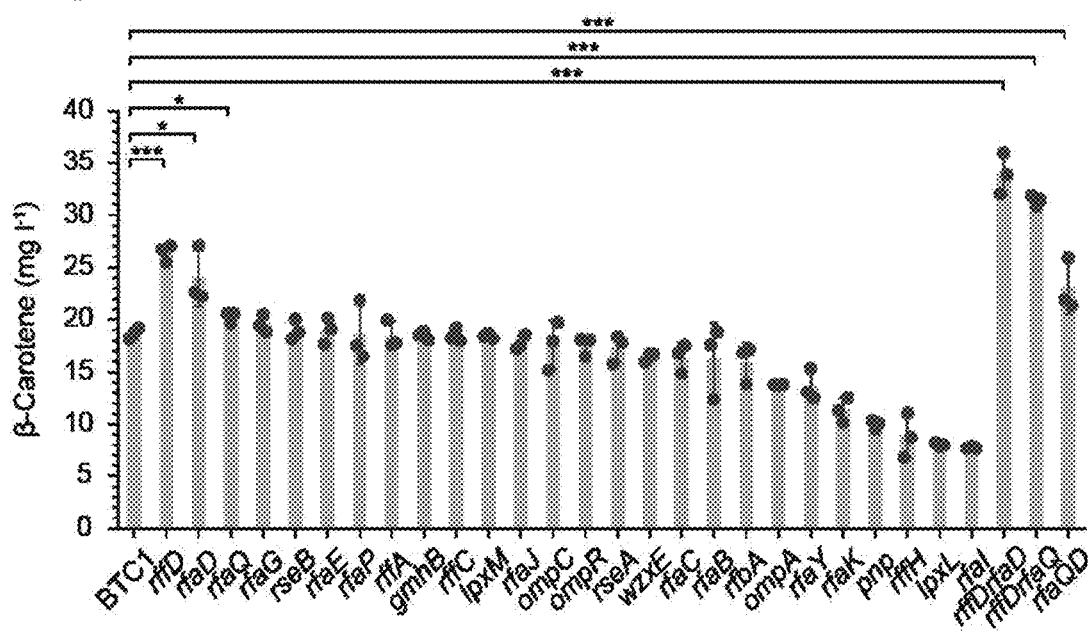

【Figure 6c】
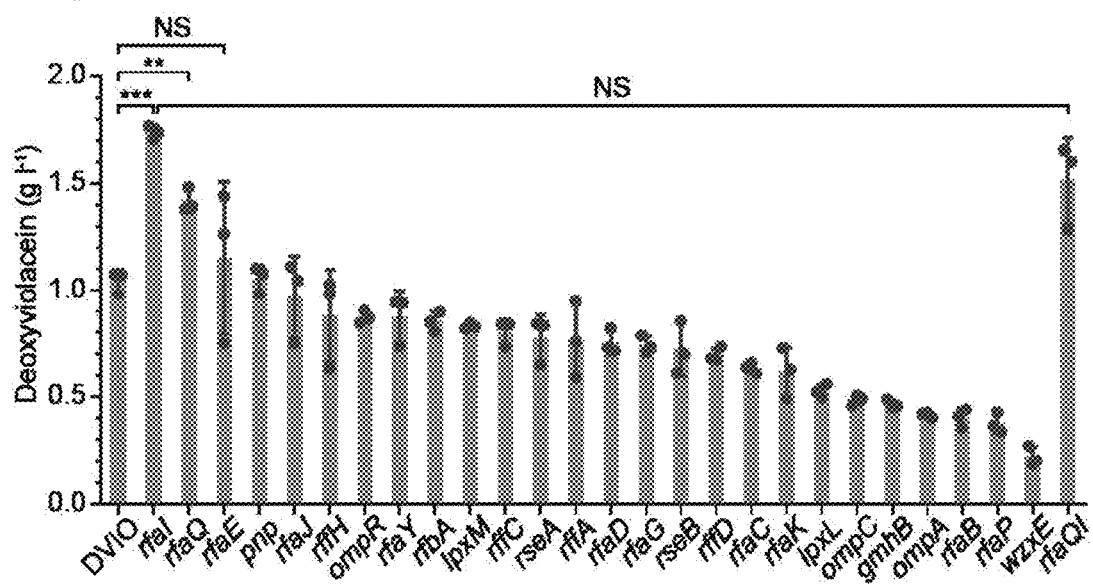
【Figure 6d】
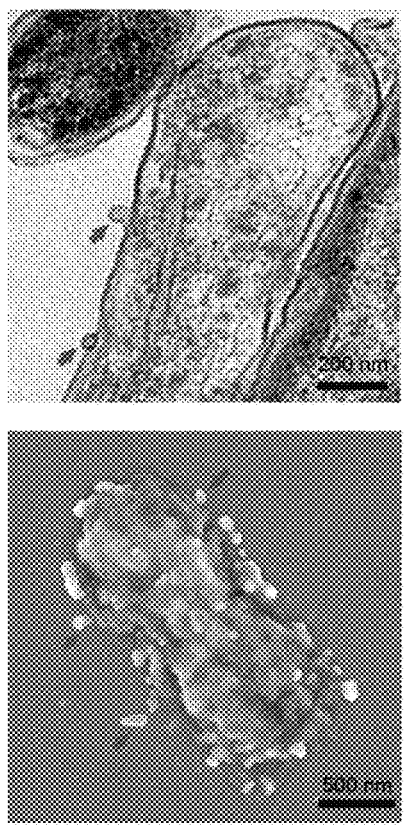

[Figure 6e]
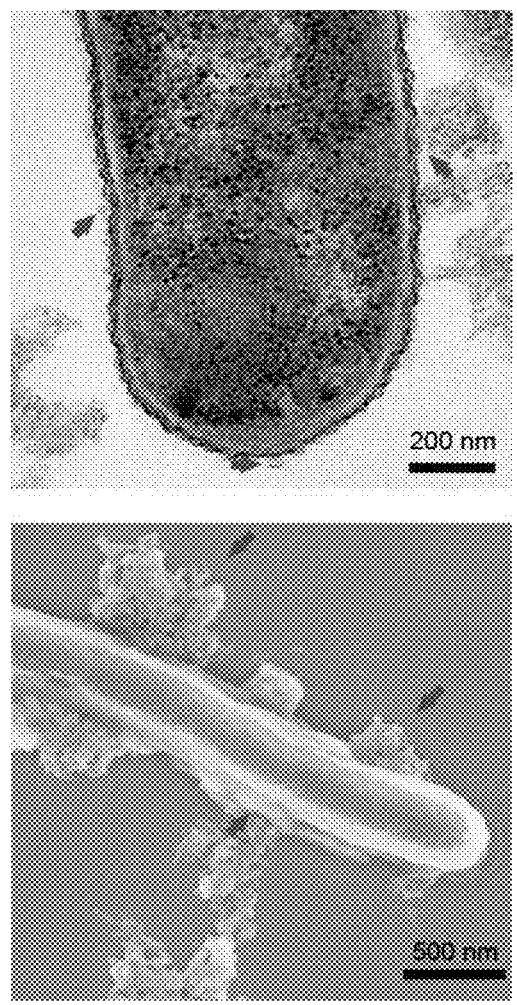

[Figure 6f]
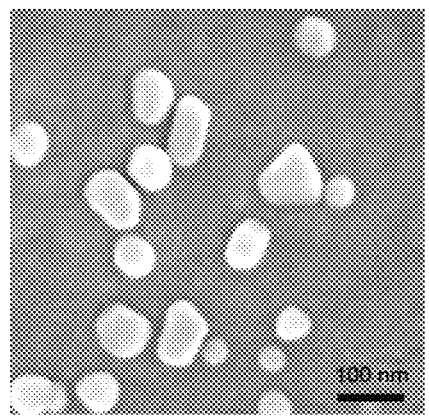
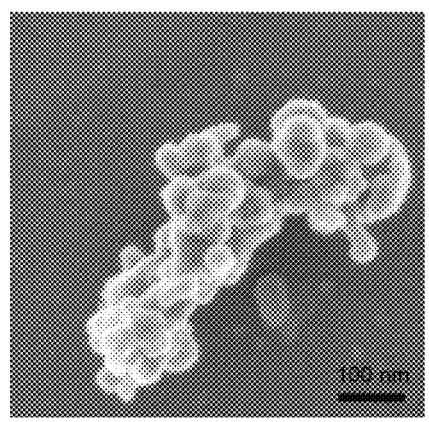
[Figure 6g]
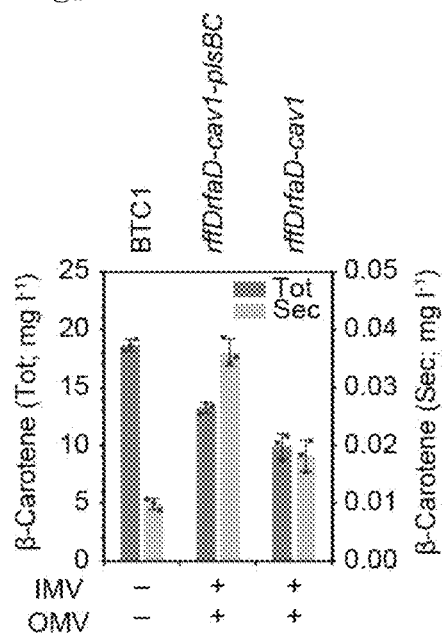

[Figure 6h]
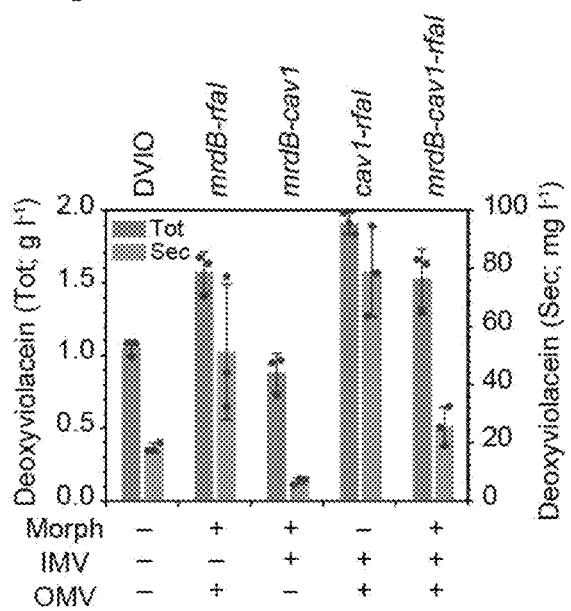
[Figure 6i]
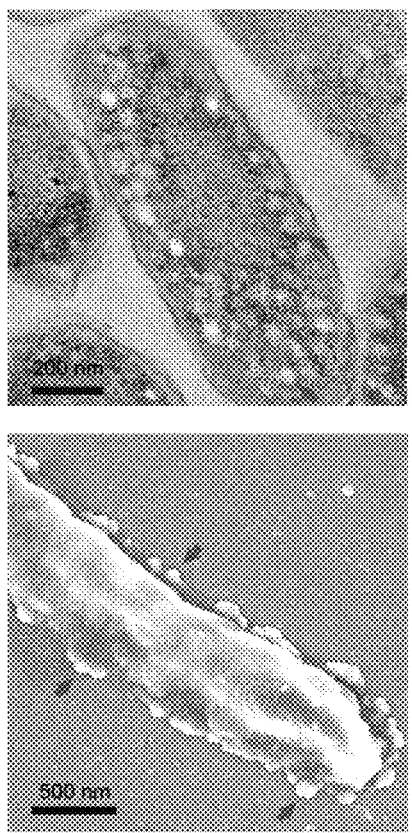

【Figure 6j】
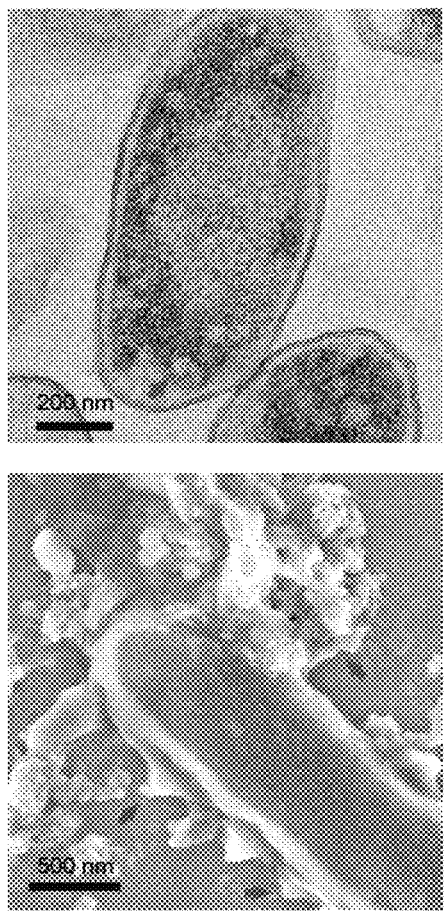
【Figure 7a】
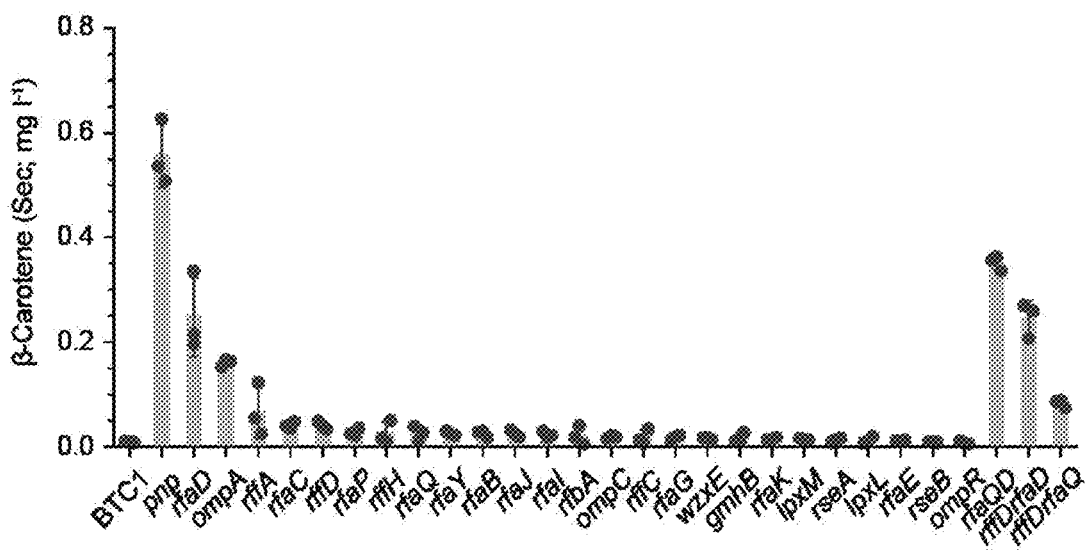

[Figure 7b]
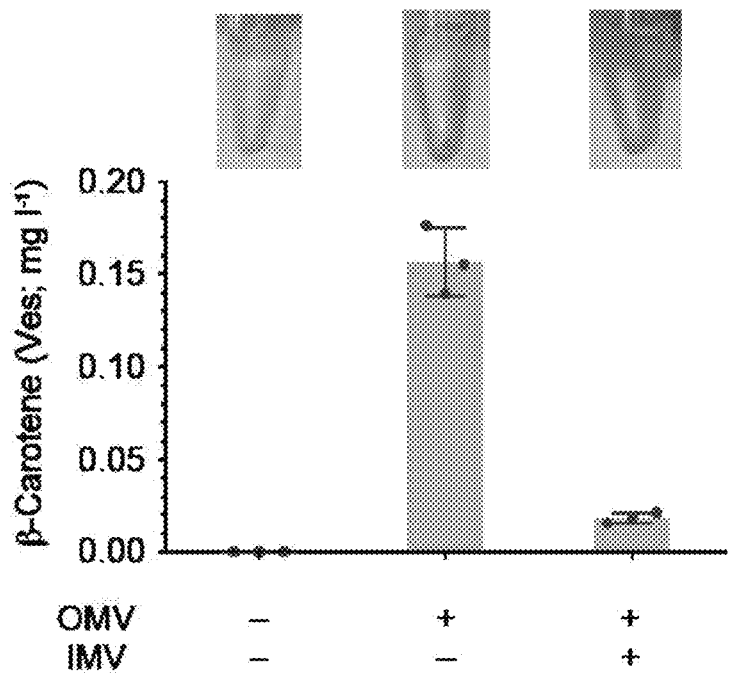
[Figure 7c]
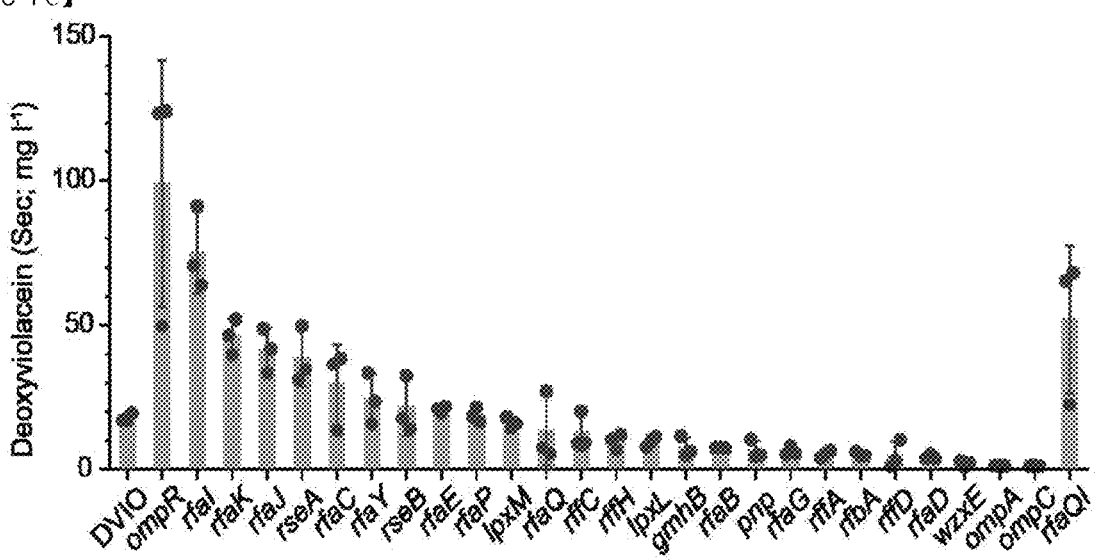

【Figure 7d】
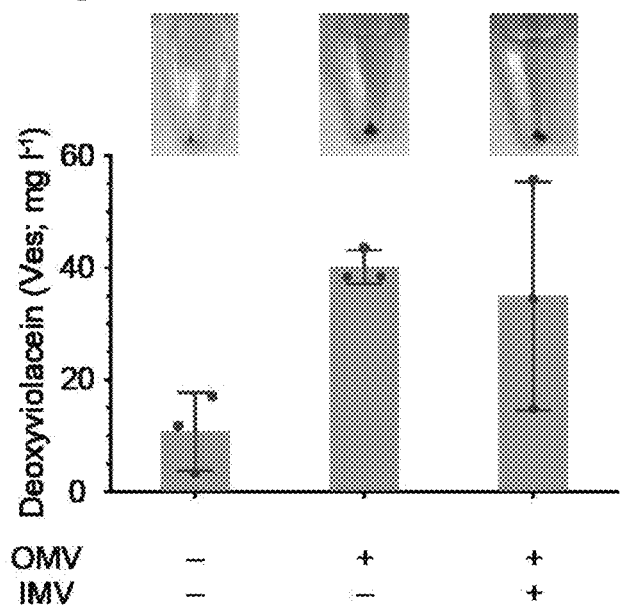
【Figure 7e】
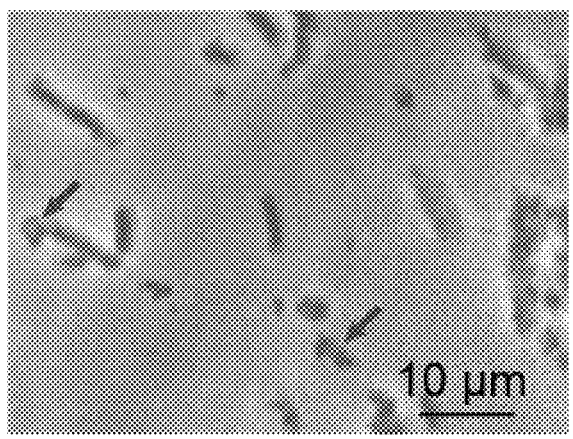
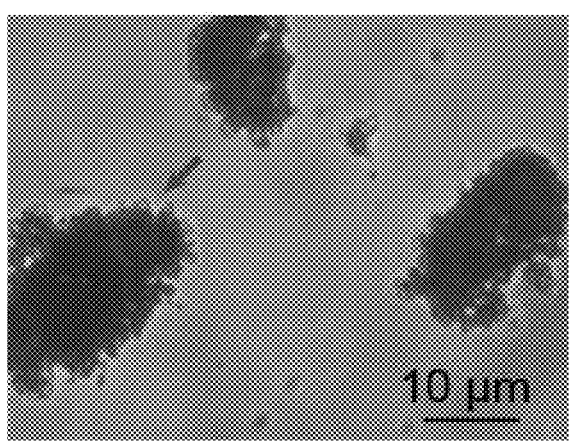

[Figure 7f]
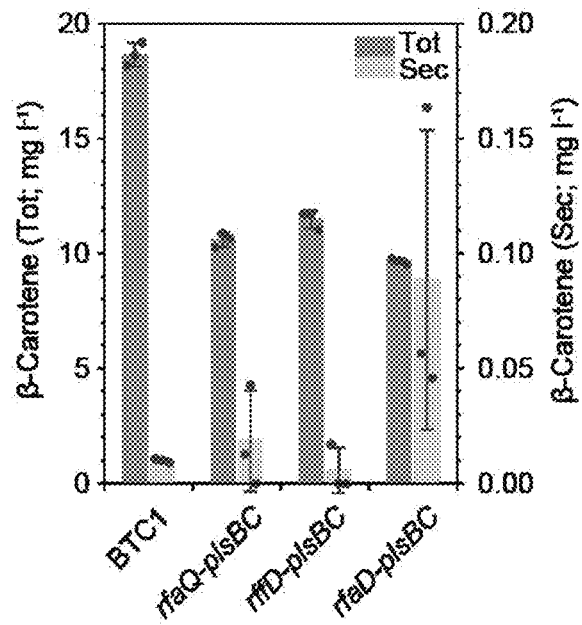
[Figure 7g]
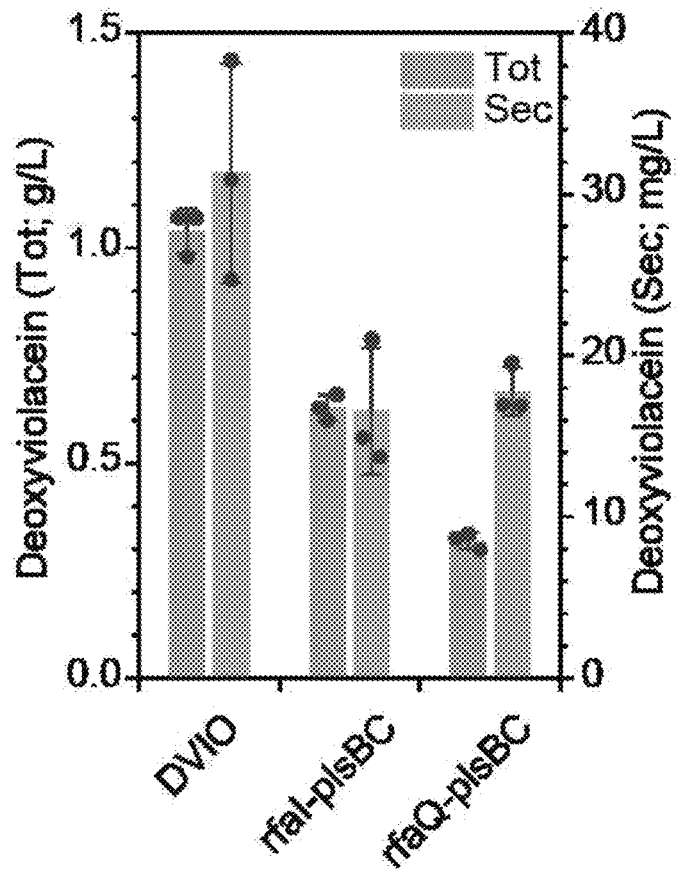

[Figure 7h]
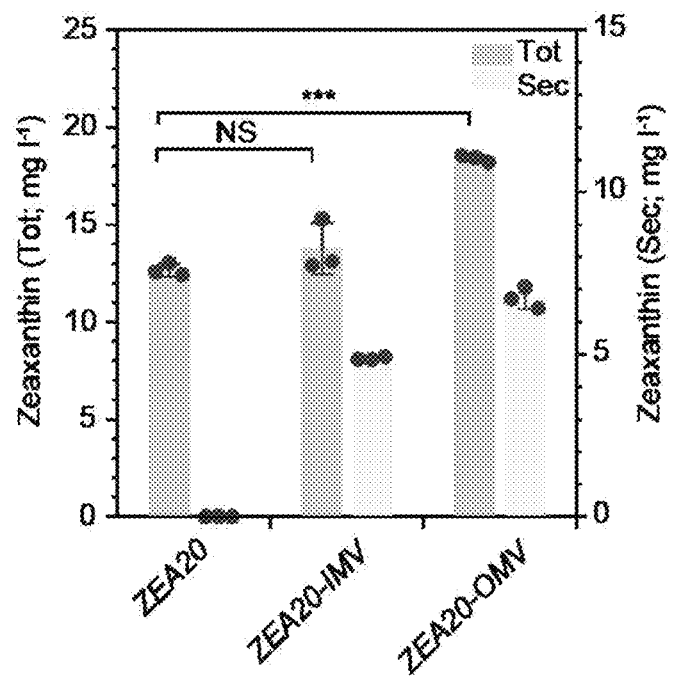
[Figure 7i]
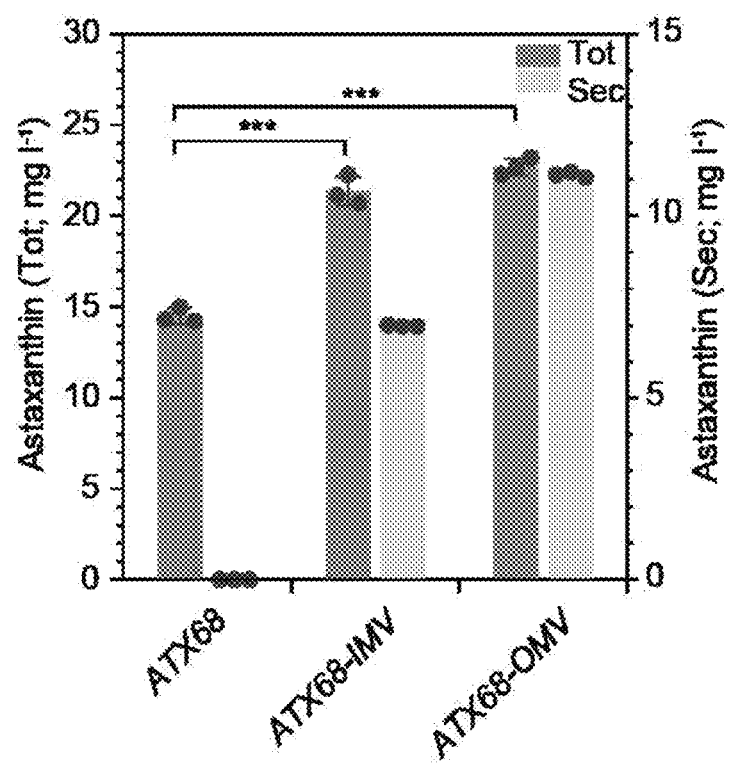

【Figure 7j】
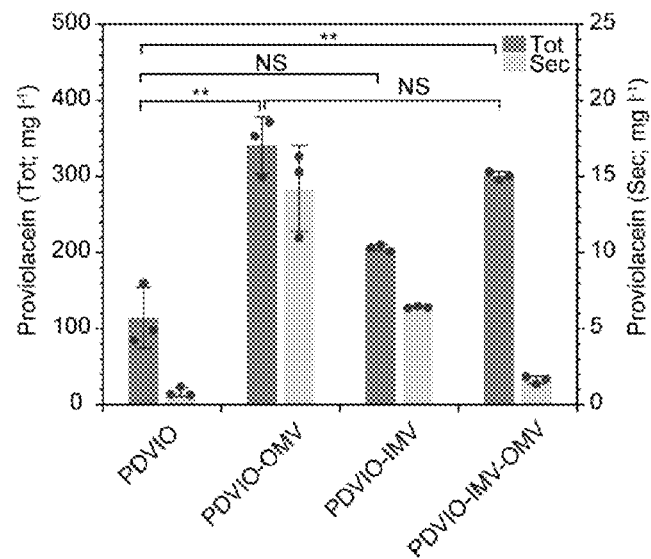
【Figure 7k】
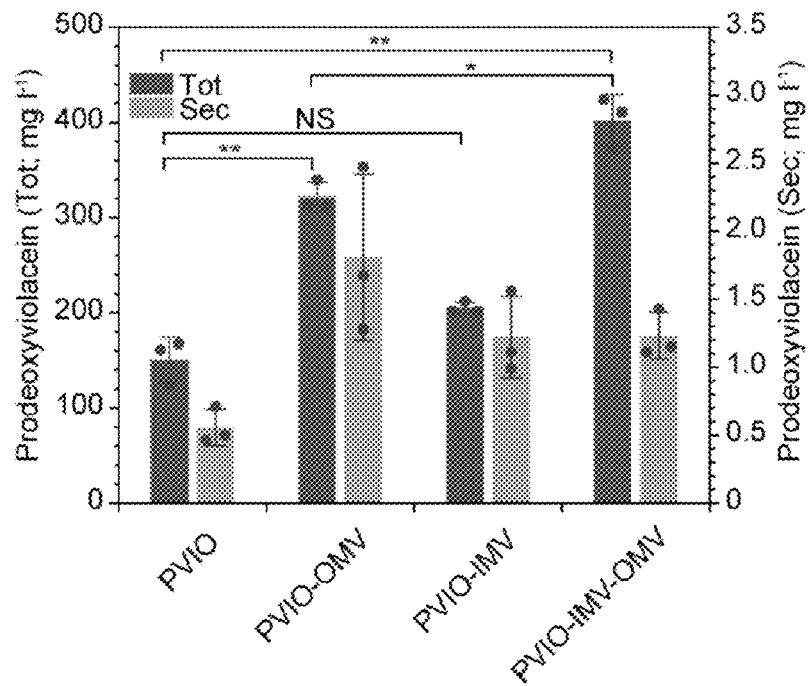

[Figure 7I]
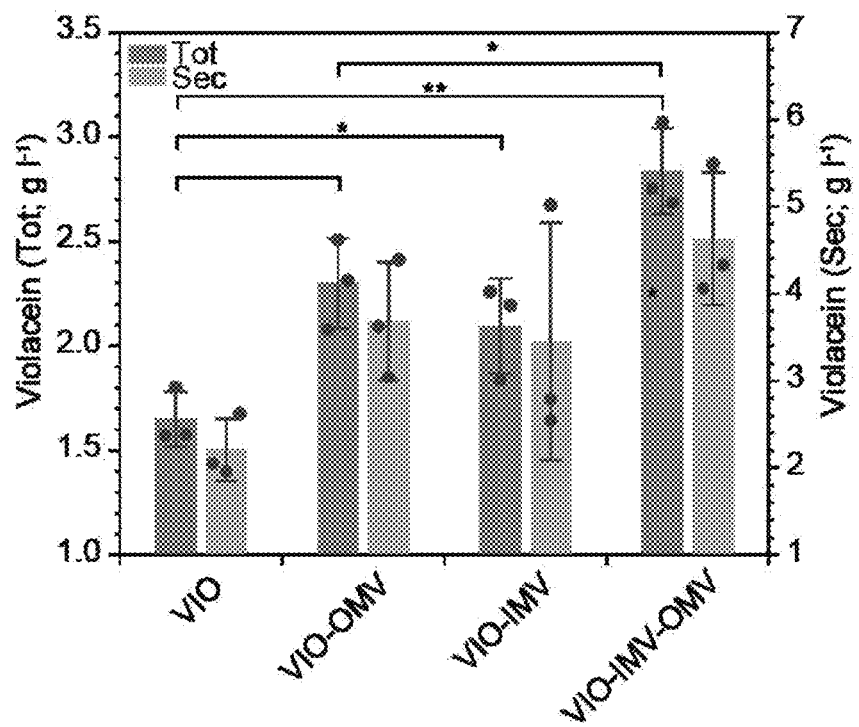
[Figure 8a]
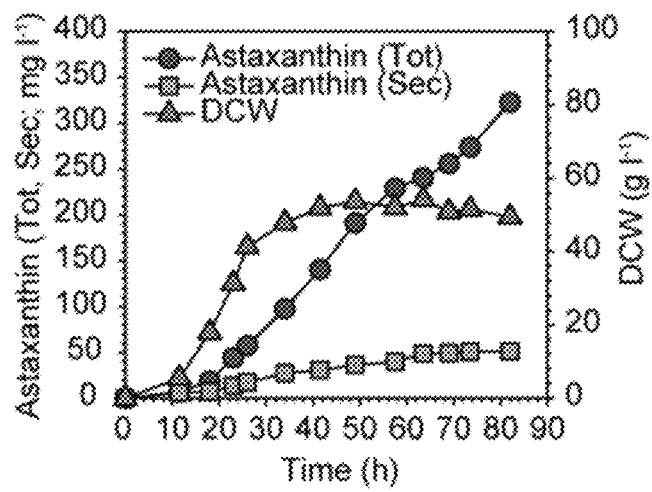

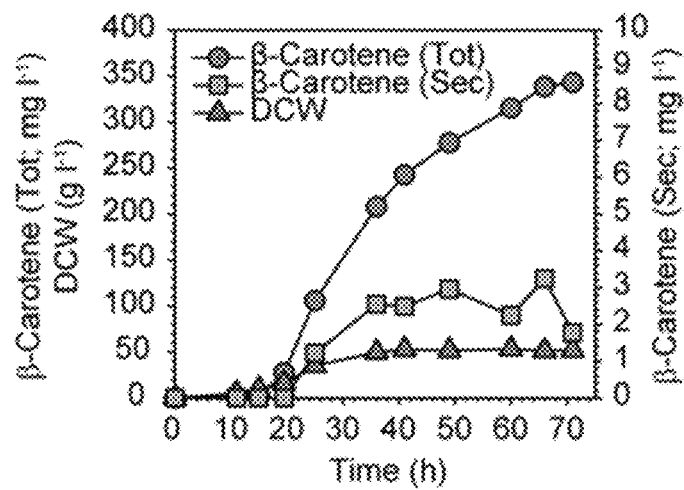
[Figure 8b]
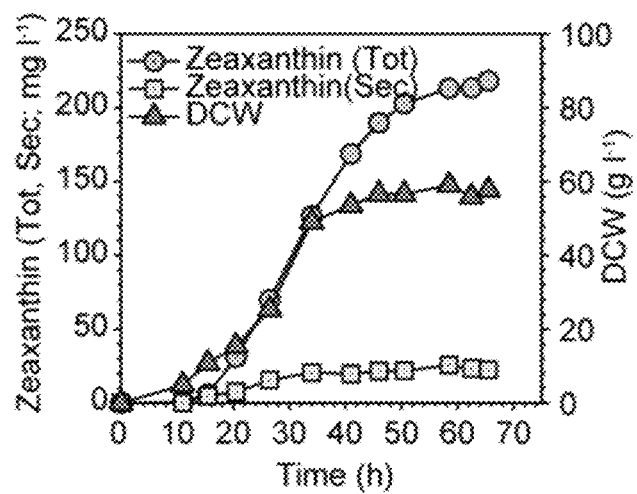
[Figure 8c]

[Figure 8d]
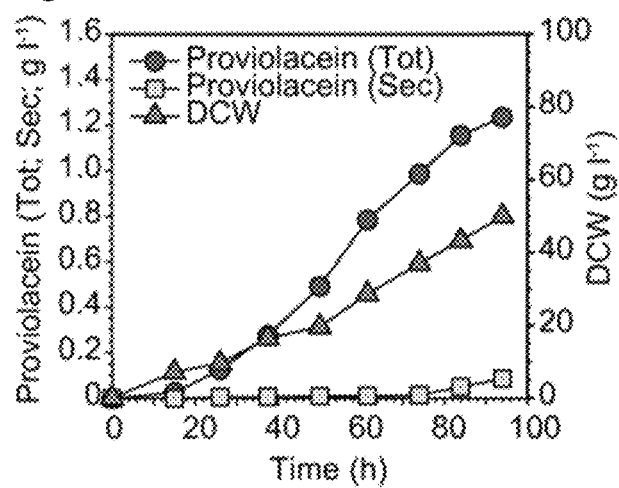
[Figure 8e]
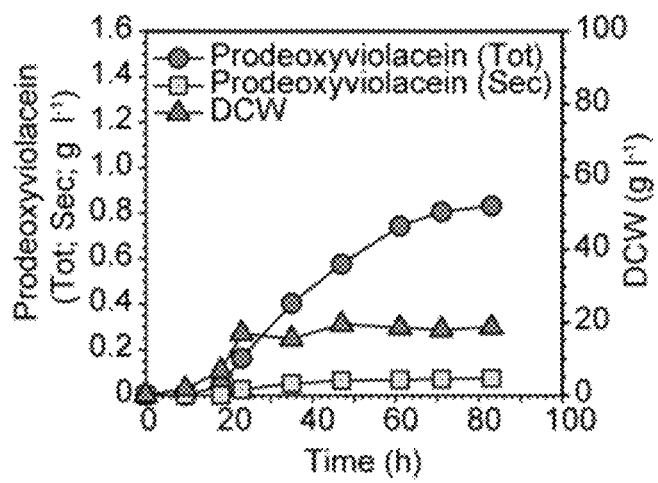

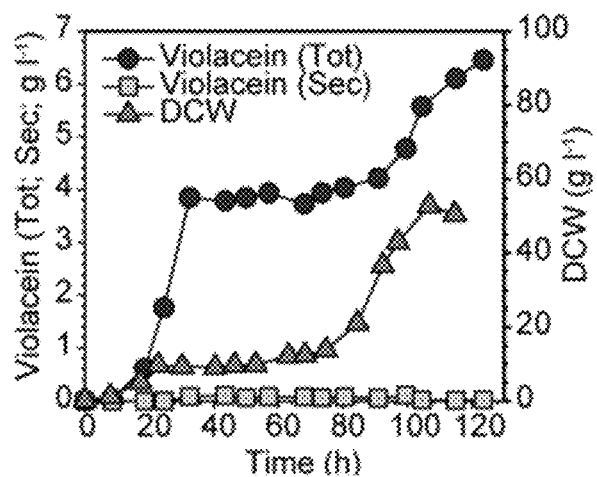
[Figure 8f]
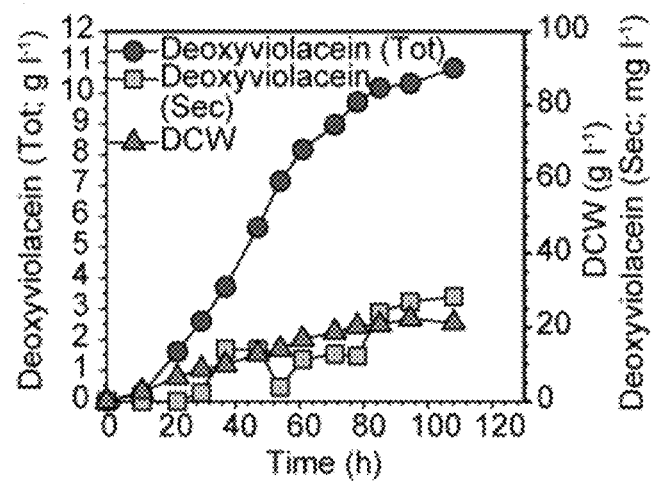
[Figure 8g]

SEQUENCE LISTING

<160> NUMBER OF SEQ ID NOS: 49

<210> SEQ ID NO 1
<211> LENGTH: 20
<212> TYPE: DNA
<213> ORGANISM: Artificial Sequence
<220> FEATURE:
<223> OTHER INFORMATION: pTac15K plasmid primer-Forward

<400> SEQUENCE: 1
cttggctgtt ttggcggatg                                           20

<210> SEQ ID NO 2
<211> LENGTH: 29
<212> TYPE: DNA
<213> ORGANISM: Artificial Sequence
<220> FEATURE:
<223> OTHER INFORMATION: pTac15K plasmid primer-Reverse

<400> SEQUENCE: 2
tgtttcctgt gtgaaattgt tatccgctc                                 29

<210> SEQ ID NO 3
<211> LENGTH: 69
<212> TYPE: DNA
<213> ORGANISM: Artificial Sequence
<220> FEATURE:
<223> OTHER INFORMATION: crtE primer-Forward

<400> SEQUENCE: 3
ataacaattt cacacaggaa acacgytcmg cggaaagrag catcgwccat gtatccgttt    60
ataaggaca                                                           69

<210> SEQ ID NO 4
<211> LENGTH: 20
<212> TYPE: DNA
<213> ORGANISM: Artificial Sequence
<220> FEATURE:
<223> OTHER INFORMATION: crtE primer-Reverse

<400> SEQUENCE: 4
ttaactgacg gcagcgagtt                                           20

<210> SEQ ID NO 5
<211> LENGTH: 61
<212> TYPE: DNA
<213> ORGANISM: Artificial Sequence
<220> FEATURE:
<223> OTHER INFORMATION: crtB primer-Forward

<400> SEQUENCE: 5
cgctgccgtc agttaaarcc ttgttcaaag gmsyatctag gatgaataat ccgtcgttac    60
t                                                                   61

<210> SEQ ID NO 6
<211> LENGTH: 30
<212> TYPE: DNA
<213> ORGANISM: Artificial Sequence
<220> FEATURE:
<223> OTHER INFORMATION: crtB primer-Reverse

<400> SEQUENCE: 6
ttcgaacggt tcttagagcg ggcgctgcca                                30

```
<210> SEQ ID NO 7
<211> LENGTH: 52
<212> TYPE: DNA
<213> ORGANISM: Artificial Sequence
<220> FEATURE:
<223> OTHER INFORMATION: crtI primer-Forward

<400> SEQUENCE: 7
gctctaagaa ccgttcgaaw gsagcrtmca agatgaaacc aactacggta at        52

<210> SEQ ID NO 8
<211> LENGTH: 35
<212> TYPE: DNA
<213> ORGANISM: Artificial Sequence
<220> FEATURE:
<223> OTHER INFORMATION: crtI primer-Reverse

<400> SEQUENCE: 8
cgccaaaaca gccaagttaa atcagatcct ccagc                            35

<210> SEQ ID NO 9
<211> LENGTH: 18
<212> TYPE: DNA
<213> ORGANISM: Artificial Sequence
<220> FEATURE:
<223> OTHER INFORMATION: pTrcCDFS plasmid primer-Forward

<400> SEQUENCE: 9
tctagagtcg acctgcag                                               18

<210> SEQ ID NO 10
<211> LENGTH: 20
<212> TYPE: DNA
<213> ORGANISM: Artificial Sequence
<220> FEATURE:
<223> OTHER INFORMATION: pTrcCDFS plasmid primer-Reverse

<400> SEQUENCE: 10
tctgtttcct gtgtgaaatt                                             20

<210> SEQ ID NO 11
<211> LENGTH: 61
<212> TYPE: DNA
<213> ORGANISM: Artificial Sequence
<220> FEATURE:
<223> OTHER INFORMATION: crtY primer-Forward

<400> SEQUENCE: 11
caatttcaca caggaaacag accttcctcc awaagragca tcmastatgg gagcggctat 60
g                                                                 61

<210> SEQ ID NO 12
<211> LENGTH: 36
<212> TYPE: DNA
<213> ORGANISM: Artificial Sequence
<220> FEATURE:
<223> OTHER INFORMATION: crtY primer 1-Reverse

<400> SEQUENCE: 12
gcaggtcgac tctagattaa cgatgagtcg tcataa                           36

<210> SEQ ID NO 13
<211> LENGTH: 20
<212> TYPE: DNA
<213> ORGANISM: Artificial Sequence
<220> FEATURE:
```

<223> OTHER INFORMATION: crtY primer 2-Reverse

<400> SEQUENCE: 13
ttaacgatga gtcgtcataa    20

<210> SEQ ID NO 14
<211> LENGTH: 67
<212> TYPE: DNA
<213> ORGANISM: Artificial Sequence
<220> FEATURE:
<223> OTHER INFORMATION: crtZ primer-Forward

<400> SEQUENCE: 14
cattatgacg actcatcgtt aaagtacatc cgammgsagc atccttkatg ttgtggattt    60
ggaatgc    67

<210> SEQ ID NO 15
<211> LENGTH: 31
<212> TYPE: DNA
<213> ORGANISM: Artificial Sequence
<220> FEATURE:
<223> OTHER INFORMATION: crtZ primer-Reverse

<400> SEQUENCE: 15
gcaggtcgac tctagattac ttcccggatg c    31

<210> SEQ ID NO 16
<211> LENGTH: 52
<212> TYPE: DNA
<213> ORGANISM: Artificial Sequence
<220> FEATURE:
<223> OTHER INFORMATION: trCrBKT primer-Forward

<400> SEQUENCE: 16
agacaggtcg ackccacccc gcaaaggags atcgkcratg ggtccgggca tc    52

<210> SEQ ID NO 17
<211> LENGTH: 27
<212> TYPE: DNA
<213> ORGANISM: Artificial Sequence
<220> FEATURE:
<223> OTHER INFORMATION: trCrBKT primer-Reverse

<400> SEQUENCE: 17
agacagaagc ttttacgcca gcgccgc    27

<210> SEQ ID NO 18
<211> LENGTH: 20
<212> TYPE: DNA
<213> ORGANISM: Artificial Sequence
<220> FEATURE:
<223> OTHER INFORMATION: pTacCDFS plasmid primer-Forward

<400> SEQUENCE: 18
tggaattcga gctcggtacc    20

<210> SEQ ID NO 19
<211> LENGTH: 20
<212> TYPE: DNA
<213> ORGANISM: Artificial Sequence
<220> FEATURE:
<223> OTHER INFORMATION: pTacCDFS plasmid primer-Reverse

<400> SEQUENCE: 19
ttcacacagg aaacagacca    20

<210> SEQ ID NO 20
<211> LENGTH: 42
<212> TYPE: DNA
<213> ORGANISM: Artificial Sequence
<220> FEATURE:
<223> OTHER INFORMATION: vioAB primer-Forward

<400> SEQUENCE: 20
cacacaggaa acagaccaat gaagcattct tccgatatct gc            42

<210> SEQ ID NO 21
<211> LENGTH: 21
<212> TYPE: DNA
<213> ORGANISM: Artificial Sequence
<220> FEATURE:
<223> OTHER INFORMATION: vioAB mid primer-Reverse

<400> SEQUENCE: 21
gccaggcttc ggaatcgaat g                                    21

<210> SEQ ID NO 22
<211> LENGTH: 21
<212> TYPE: DNA
<213> ORGANISM: Artificial Sequence
<220> FEATURE:
<223> OTHER INFORMATION: vioAB mid primer-Forward

<400> SEQUENCE: 22
cattcgattc cgaagcctgg c                                    21

<210> SEQ ID NO 23
<211> LENGTH: 47
<212> TYPE: DNA
<213> ORGANISM: Artificial Sequence
<220> FEATURE:
<223> OTHER INFORMATION: vioAB primer-Reverse

<400> SEQUENCE: 23
ggtaccgagc tcgaattcca ttatcaggcc tctctagaaa gctttcc        47

<210> SEQ ID NO 24
<211> LENGTH: 41
<212> TYPE: DNA
<213> ORGANISM: Artificial Sequence
<220> FEATURE:
<223> OTHER INFORMATION: vioC primer-Forward

<400> SEQUENCE: 24
cacacaggaa acagaccaat gaaaagagca atcatagtcg g              41

<210> SEQ ID NO 25
<211> LENGTH: 45
<212> TYPE: DNA
<213> ORGANISM: Artificial Sequence
<220> FEATURE:
<223> OTHER INFORMATION: vioC primer-Reverse

<400> SEQUENCE: 25
ggtaccgagc tcgaattcca ttatcagttg accctcccta tcttg          45

<210> SEQ ID NO 26
<211> LENGTH: 39
<212> TYPE: DNA
<213> ORGANISM: Artificial Sequence
<220> FEATURE:

<223> OTHER INFORMATION: vioD primer-Forward

<400> SEQUENCE: 26
cacacaggaa acagaccaat gaagattctg gtcatcggc    39

<210> SEQ ID NO 27
<211> LENGTH: 42
<212> TYPE: DNA
<213> ORGANISM: Artificial Sequence
<220> FEATURE:
<223> OTHER INFORMATION: vioD primer-Reverse

<400> SEQUENCE: 27
ggtaccgagc tcgaattcca ttatcagcgt tgcagcgcgt ag    42

<210> SEQ ID NO 28
<211> LENGTH: 38
<212> TYPE: DNA
<213> ORGANISM: Artificial Sequence
<220> FEATURE:
<223> OTHER INFORMATION: vioE primer-Forward

<400> SEQUENCE: 28
cacacaggaa acagaccaat ggaaaaccgg gaaccgcc    38

<210> SEQ ID NO 29
<211> LENGTH: 42
<212> TYPE: DNA
<213> ORGANISM: Artificial Sequence
<220> FEATURE:
<223> OTHER INFORMATION: vioE primer-Reverse

<400> SEQUENCE: 29
ggtaccgagc tcgaattcca ttactagcgc ttggcggcga ag    42

<210> SEQ ID NO 30
<211> LENGTH: 41
<212> TYPE: DNA
<213> ORGANISM: Artificial Sequence
<220> FEATURE:
<223> OTHER INFORMATION: vioE_frag primer-Forward

<400> SEQUENCE: 30
cctgataatg gaattcgagc tgactgcacg gtgcaccaat g    41

<210> SEQ ID NO 31
<211> LENGTH: 21
<212> TYPE: DNA
<213> ORGANISM: Artificial Sequence
<220> FEATURE:
<223> OTHER INFORMATION: vioE_frag primer-Reverse

<400> SEQUENCE: 31
caggtcgact ctagaggatc c    21

<210> SEQ ID NO 32
<211> LENGTH: 41
<212> TYPE: DNA
<213> ORGANISM: Artificial Sequence
<220> FEATURE:
<223> OTHER INFORMATION: vio_frag primer-Forward

<400> SEQUENCE: 32
gctagtaatg gaattcgagc tgactgcacg gtgcaccaat g    41

<210> SEQ ID NO 33
<211> LENGTH: 53
<212> TYPE: DNA
<213> ORGANISM: Artificial Sequence
<220> FEATURE:
<223> OTHER INFORMATION: cav2 primer-Forward

<400> SEQUENCE: 33
ttaactggat cctttcacac aggaaacaga ccatggggct tgagactgag aag        53

<210> SEQ ID NO 34
<211> LENGTH: 24
<212> TYPE: DNA
<213> ORGANISM: Artificial Sequence
<220> FEATURE:
<223> OTHER INFORMATION: cav primer-Reverse

<400> SEQUENCE: 34
catccgccaa aacagccaag cttg                                         24

<210> SEQ ID NO 35
<211> LENGTH: 53
<212> TYPE: DNA
<213> ORGANISM: Artificial Sequence
<220> FEATURE:
<223> OTHER INFORMATION: cav3 primer-Forward

<400> SEQUENCE: 35
ttaactctgc agtttcacac aggaaacaga ccatgatggc cgaagagcat acc        53

<210> SEQ ID NO 36
<211> LENGTH: 537
<212> TYPE: DNA
<213> ORGANISM: Artificial Sequence
<220> FEATURE:
<223> OTHER INFORMATION: cav1 gene

<400> SEQUENCE: 36
atgtctgggg gcaaatacgt agactcggag ggacatctct acaccgttcc catccgggaa   60
cagggcaaca tctacaagcc caacaacaag gccatggcag acgagctgag cgagaagcaa  120
gtgtacgacg cgcacaccaa ggagatcgac ctggtcaacc gcgaccctaa acacctcaac  180
gatgacgtgg tcaagattga cttttgaagat gtgattgcag aaccagaagg gacacacagt  240
tttcacggca tttggaaggc cagcttcacc accttcactg tgacgaaata ctggttttac  300
cgcttgctgt ctgccctctt tggcatcccg atggcactca tctggggcat ttacttcgcc  360
attctctctt tcctgcacat ctgggcagtt gtaccatgca ttaagagctt cctgattgag  420
attcagtgca ccagccgtgt ctattccatc tacgtccaca ccgtctgtga cccactcttt  480
gaagctgttg ggaaaatatt cagcaatgtc cgcatcaact gcagaaaga aatataa     537

<210> SEQ ID NO 37
<211> LENGTH: 489
<212> TYPE: DNA
<213> ORGANISM: Artificial Sequence
<220> FEATURE:
<223> OTHER INFORMATION: cav2 gene

<400> SEQUENCE: 37
atggggcttg agactgagaa ggcagatgtc caactgttca tggatgatga ttcttactca   60
catcactcag gactggaata tgcagatcca gaaaagtttg cggactccga ccaggatcgt  120
gacccccacc gcttaaatag tcacttaaaa ctgggctttg aagatgtgat cgcggagcct  180

```
gtcacaactc atagtttcga taaggtttgg atttgctcac acgcattatt tgaaatttca      240
aagtacgtta tgtataagtt ccttactgta tttttggcca tccctcttgc ctttatcgca      300
ggaatcctgt tcgctacctt gagttgtctg cacatttgga ttcttatgcc attcgtaaag      360
acatgcctta tggtgttgcc atcagtgcaa accatctgga agtccgtcac tgatgtaatt      420
attgccccct tgtgtacatc tgtgggccgc tgcttttcga gcgtctcact tcaattgtcg      480
caggattaa                                                              489

<210> SEQ ID NO 38
<211> LENGTH: 456
<212> TYPE: DNA
<213> ORGANISM: Artificial Sequence
<220> FEATURE:
<223> OTHER INFORMATION: cav3 gene

<400> SEQUENCE: 38
atgatggccg aagagcatac cgatcttgaa gctcaaattg taaaggatat tcattgtaag       60
gaaattgact tggttaatcg tgatcctaag aacatcaacg aggatatcgt taaggtagac      120
ttcgaggatg ttattgcaga acctgttgga acatacagtt tcgacggtgt ctggaaggtg      180
tcgtacacta cgtttaccgt tagtaagtat tggtgctatc gcttactgtc cactctgttg      240
ggtgtccccc ttgctttgct ttggggattc ctgttcgcgt gtatctcttt ttgccatatt      300
tgggctgtcg ttccatgtat taaatcgtac ttaattgaga ttcaatgtat ctctcatatt      360
tatagtcttt gtatccgcac gttctgtaat ccccttttg cggccttggg gcaggtgtgc       420
tcaagtatta aggttgtact tcgtaaggag gtctaa                                456

<210> SEQ ID NO 39
<211> LENGTH: 55
<212> TYPE: DNA
<213> ORGANISM: Artificial Sequence
<220> FEATURE:
<223> OTHER INFORMATION: plsB primer-Forward

<400> SEQUENCE: 39
ctagagtcga cctgcagttt cacacaggaa acagaccatg tccggctggc acga            55

<210> SEQ ID NO 40
<211> LENGTH: 37
<212> TYPE: DNA
<213> ORGANISM: Artificial Sequence
<220> FEATURE:
<223> OTHER INFORMATION: plsB primer-Reverse

<400> SEQUENCE: 40
tctgtttcct gtgtgaaatt acccttcgcc ctgcgtc                               37

<210> SEQ ID NO 41
<211> LENGTH: 59
<212> TYPE: DNA
<213> ORGANISM: Artificial Sequence
<220> FEATURE:
<223> OTHER INFORMATION: plsC primer-Forward

<400> SEQUENCE: 41
gaagggtaat ttcacacagg aaacagacca tgctatatat ctttcgtctt attattacc       59

<210> SEQ ID NO 42
<211> LENGTH: 38
<212> TYPE: DNA
<213> ORGANISM: Artificial Sequence
```

```
<220> FEATURE:
<223> OTHER INFORMATION: plsC primer 1-Reverse

<400> SEQUENCE: 42
ccgccaaaac agccaagctt ttaaactttt ccggcggc                              38

<210> SEQ ID NO 43
<211> LENGTH: 41
<212> TYPE: DNA
<213> ORGANISM: Artificial Sequence
<220> FEATURE:
<223> OTHER INFORMATION: sRNA primer 1-Forward

<400> SEQUENCE: 43
cactagatct caaatgtgct ggaattctaa caccgtgcgt g                         41

<210> SEQ ID NO 44
<211> LENGTH: 43
<212> TYPE: DNA
<213> ORGANISM: Artificial Sequence
<220> FEATURE:
<223> OTHER INFORMATION: sRNA primer 1-Reverse

<400> SEQUENCE: 44
ccttataaat caaacatgtg cggcgaattg ggtacctata aac                       43

<210> SEQ ID NO 45
<211> LENGTH: 22
<212> TYPE: DNA
<213> ORGANISM: Artificial Sequence
<220> FEATURE:
<223> OTHER INFORMATION: sRNA primer 2-Forward

<400> SEQUENCE: 45
gcacatgttt gatttataag gg                                              22

<210> SEQ ID NO 46
<211> LENGTH: 22
<212> TYPE: DNA
<213> ORGANISM: Artificial Sequence
<220> FEATURE:
<223> OTHER INFORMATION: sRNA primer 2-Reverse

<400> SEQUENCE: 46
cagcacattt gagatctagt gg                                              22

<210> SEQ ID NO 47
<211> LENGTH: 40
<212> TYPE: DNA
<213> ORGANISM: Artificial Sequence
<220> FEATURE:
<223> OTHER INFORMATION: ptrc primer-Forward

<400> SEQUENCE: 47
atgtgacagc ttatcgcatg cttgacaatt aatcatccgg                           40

<210> SEQ ID NO 48
<211> LENGTH: 42
<212> TYPE: DNA
<213> ORGANISM: Artificial Sequence
<220> FEATURE:
<223> OTHER INFORMATION: plsC primer-Reverse

<400> SEQUENCE: 48
cctgggttta cctaggcatg cttaaacttt tccggcggct tc                        42
```

```
<210> SEQ ID NO 49
<211> LENGTH: 43
<212> TYPE: DNA
<213> ORGANISM: Artificial Sequence
<220> FEATURE:
<223> OTHER INFORMATION: cav1 primer-Reverse

<400> SEQUENCE: 49
cctgggttta cctaggcatg cttatatttc tttctgcaag ttg            43
```

RECOMBINANT MICROORGANISM HAVING INCREASED ABILITY TO PRODUCE HYDROPHOBIC MATERIAL AND CELL-MEMBRANE ENGINEERING METHOD FOR PREPARATION THEREOF

CROSS-REFERENCE TO RELATED APPLICATION

The priority under 35 USC § 119 of Korean Patent Application 10-2020-0144521 filed Nov. 2, 2020 is hereby claimed. The disclosure of Korean Patent Application 10-2020-0144521 is hereby incorporated herein by reference, in its entirety, for all purposes.

REFERENCE TO SEQUENCE LISTING SUBMITTED VIA EFS-WEB

This application includes an electronically submitted sequence listing in .txt format. The .txt file contains a sequence listing entitled "589 SeqListing_ST25.txt" created on Oct. 31, 2021 and is 11,978 bytes in size. The sequence listing contained in this .txt file is part of the specification and is hereby incorporated by reference herein in its entirety

BACKGROUND OF THE INVENTION

Field of the Invention

The present invention relates to a recombinant microorganism having increased ability to produce a hydrophobic material and a cell-membrane engineering method for the preparation thereof, and more particularly to a recombinant microorganism for producing a hydrophobic material, which is subjected to cell-membrane engineering in order to be imparted with at least one characteristic among an increase in a cell-membrane area, an increase in the formation and secretion of an outer membrane vesicle, and an increase in the formation of an inner membrane vesicle, and to a cell-membrane engineering method for the preparation thereof.

Description of the Related Art

Due to global environmental problems, depletion of non-renewable resources, and demand for eco-friendly energy sources, interest in constructing cell factories based on reproductive organisms is increasing. Such a cell factory may be manufactured by engineering the intracellular metabolic network for the production of target metabolites (bio-energy, eco-friendly chemicals, new medicines, etc.), which requires various molecular biology technologies. The wide variety of materials produced based on petrochemicals may be classified into various categories, and one of the representative classification criteria is hydrophilicity vs. hydrophobicity. A representative group of hydrophobic materials includes hydrophobic pigments (such as carotenoids and violacein). Pigments are used extensively in industries including food additives, dyes, cosmetics, paints, and the like, and are inseparable from daily life. Since pigments, when ingested or applied to the skin, directly affect the human body, interest in and demand for natural pigments, which are considered safer than problematic petroleum-based synthetic pigments, is rapidly increasing with an increase in health concerns in modern society. It is also known that petroleum-based synthetic pigments cause serious environmental problems when dyeing textiles. Natural pigments derived from nature often have various pharmaceutical properties such as anticancer, antibiotic, antibacterial, and immunosuppressive activities, in addition to a variety of colors, so they may become increasingly useful in daily life. Currently, many pigments are produced based on petrochemicals, and natural pigments account for only a small proportion of pigments that are used. This leads to health problems and environmental problems, and is particularly problematic in that petrochemical-based pigments are widely used in products for children. Moreover, petrochemical-based pigments cause serious water pollution in the textile-dyeing process.

Accordingly, there have been efforts to produce large amounts of natural pigments using a microbial cell factory in an environmentally friendly manner, among which attempts to increase the production of hydrophobic pigments accumulated on the cell membrane by enlarging the area of the cell membrane have been reported (T. Wu et al., Membrane engineering—A novel strategy to enhance the production and accumulation of beta-carotene in *Escherichia coli*. Metab. Eng. 43, 85-91 (2017)), and attempts to increase the production of hydrophobic pigments through dissolution in intracellular lipids have been made (T. Ma et al., Lipid engineering combined with systematic metabolic engineering of *Saccharomyces cerevisiae* for high-yield production of lycopene. Metab. Eng. 52, 134-142 (2019)).

Against this background, the present inventors have made great efforts to increase the ability to produce hydrophobic materials by modifying the inherent properties of microorganisms for producing hydrophobic materials through cell-membrane engineering, and thus ascertained that, when *E. coli*, which produces carotenoids and violacein analogues as natural pigments, is subjected to cell-membrane engineering through suppression, introduction or overexpression of cell-morphology-related genes, outer-membrane-vesicle-related genes, or inner-membrane-vesicle-related genes, a space in which a natural lipophilic pigment material may accumulate is enlarged by virtue of an increase in the cell membrane area, an increase in the formation and secretion of outer membrane vesicles, and an increase in the formation of inner membrane vesicles, thereby significantly increasing the amount of the natural pigment that is produced, and moreover, the synergistic effect of individual elements was tested and verified, thereby culminating in the present invention.

The information described in the background section is only for improving understanding of the background of the present invention, and it is not to be construed as including information forming the related art already known to those skilled in the art to which the present invention belongs.

SUMMARY OF THE INVENTION

It is an object of the present invention to provide a recombinant microorganism having increased ability to produce a hydrophobic material through cell-membrane engineering and a method of preparing the same.

It is another object of the present invention to provide a method of producing a hydrophobic material by culturing the recombinant microorganism.

It is still another object of the present invention to provide a method of screening a recombinant microorganism having high ability to produce a specific hydrophobic material using a recombinant microorganism library subjected to cell-membrane engineering.

In order to accomplish the above objects, the present invention provides a recombinant microorganism for producing a hydrophobic material, which is subjected to cell-membrane engineering in order to be imparted with at least one characteristic among an increase in the cell membrane area, an increase in the formation and secretion of outer membrane vesicles, and an increase in the formation of inner membrane vesicles.

In addition, the present invention provides a method of preparing a recombinant microorganism for producing a hydrophobic material, including suppressing the expression of at least one gene among a cell-morphology-related gene and an outer-membrane-vesicle-related gene in the recombinant microorganism for producing a hydrophobic material, and/or introducing or overexpressing an inner-membrane-vesicle-related gene in the recombinant microorganism for producing a hydrophobic material.

In addition, the present invention provides a method of preparing a hydrophobic material, including producing a hydrophobic material by culturing the recombinant microorganism for producing a hydrophobic material, which is subjected to cell-membrane engineering, and obtaining the produced hydrophobic material.

In addition, the present invention provides a method of screening a recombinant microorganism having increased ability to produce a specific hydrophobic material, which is subjected to cell-membrane engineering, including (a) constructing a microorganism library for producing a hydrophobic material by performing cell-membrane engineering in a microorganism for producing a hydrophobic material through at least one among suppression of expression of a cell-morphology-related gene, suppression of expression of an outer-membrane-vesicle-related gene, and introduction or overexpression of an inner-membrane-vesicle-related gene, and (b) selecting a recombinant microorganism having high ability to produce a specific hydrophobic material by culturing the microorganism for producing a hydrophobic material.

BRIEF DESCRIPTION OF THE DRAWINGS

The above and other objects, features, and other advantages of the present invention will be more clearly understood from the following detailed description taken in conjunction with the accompanying drawings, in which:

FIG. 1 schematically shows a cell-membrane engineering strategy for cell membrane space expansion and a biosynthesis pathway for carotenoids and violacein analogues, in which cell morphology may be modified by suppressing expression of a related gene using a synthetic sRNA system, and outer membrane vesicles may also be formed in the same way, whereas inner membrane vesicles may be formed through expression of a foreign gene such as cav1 or the like, and in which curved arrows and T models designate a promoter and a transcription terminator, respectively, solid and dotted lines designate single and multiple responses, respectively, and abbreviations are as follows: G3P denoting glyceraldehyde 3-phosphate, E4P denoting erythrose 4-phosphate, PEP denoting phosphoenolpyruvate, PYR denoting pyruvate, DXP denoting 1-deoxy-D-xylulose 5-phosphate, SKM denoting shikimate, FPP denoting farnesyl diphosphate, GGPP denoting geranylgeranyl pyrophosphate, TRP denoting tryptophan, IPA denoting indole pyruvate, and Sp. denoting spontaneous;

FIGS. 2A to 2J show the results of construction of carotenoid-producing strains and of culture of the constructed strains, FIG. 2A schematically showing the plasmids of pLYC, pBTC, pZEA, and pATX libraries, curved arrows, hemispheres, and T models designating a promoter, a 5' UTR, and a transcription terminator, respectively, FIG. 2B showing the initial screening results of LYC strains, FIG. 2C showing the results of additional flask culture of good strains after conspicuous red colonies are selected and then test-tube cultured, FIGS. 2D to 2F showing the results of test-tube culture of BTC, ZEA, and ATX strains, respectively, FIG. 2G showing the results of HPLC analysis of 50 good strain samples of FIG. 2F, in which the area value of the peak corresponding to astaxanthin for each sample is plotted on the y-axis, FIGS. 2H, 2I and 2J showing the results of flask culture of BTC, ZEA, and ATX strains selected from among the results of test-tube culture, respectively, error bars representing mean±standard deviation (n=3), P<0.01, *P<0.001, NS (not significant) P 0.05 being determined by a two-tailed Student's t-test;

FIGS. 3A to 3G show the results of construction of violacein-analogue-producing strains and of culture of the constructed strains, FIG. 3A schematically showing the plasmids constructed for the production of violacein analogues, FIG. 3B showing the results of a comparison of the amount of violacein that is produced using glucose or glycerol as a single carbon source, FIG. 3C showing the results of production of prodeoxyviolacein and proviolacein in PDVIO and PVIO strains using glycerol, FIG. 3D showing the results of production of deoxyviolacein and violacein in DVIO and VIO strains using glycerol, FIGS. 3E and 3F showing LC-MS chromatograms and spectra of prodeoxyviolacein and proviolacein respectively produced from the E. coli strain, and FIG. 3G showing the absorption spectra of carotenoids and violacein analogues in the wavelength range of 350 to 750 nm, in which each data point in the graph of FIG. 3G is an average value obtained from three separate samples, and these points are connected to form a curve graph;

FIGS. 4A to 4J show the results of increased production of carotenoids and violacein analogues through modification of cell morphology and formation of inner membrane vesicles, FIG. 4A showing the mechanism of cell membrane space expansion through cell morphology modification of E. coli, FIGS. 4B and 4C respectively showing the results of production of β-carotene and deoxyviolacein through introduction of sRNA that suppress expression of cell-morphology-related genes, FIG. 4D showing the mechanism of formation of an inner membrane vesicle in E. coli, FIGS. 4E and 4F respectively showing the results of production of β-carotene and deoxyviolacein, and FIGS. 4G, 4H, 4I and 4J showing TEM (upper panel) and SEM (lower panel) images of a BTC1 strain as a β-carotene-producing control group, a β-carotene-producing strain expressing cav1, a DVIO strain as a deoxyviolacein-producing control group, and a deoxyviolacein-producing strain expressing cav1, respectively, error bars in the production graphs representing mean±standard deviation (n=3), *P<0.05, P<0.01, *P<0.001, NS (not significant) P≥0.05 being determined by two-tailed Student's t-test;

FIGS. 5A and 5B show microscope images of BTC1 and DVIO strains in which cell morphology is modified, FIG. 5A showing microscope images of the BTC1 strain and the BTC1 strain introduced with sRNA that suppresses expression of cell-morphology-related genes, and FIG. 5B showing microscope images of the DVIO strain and the DVIO strain introduced with sRNA that suppresses expression of cell-morphology-related genes, in which longer or shorter cell morphologies than the control group were observed in the strains introduced with sRNA that suppresses expression of cell-morphology-related genes, and for each micrograph, the corresponding expression suppression target gene is marked;

FIGS. 6A to 6J show the results of increased production of carotenoids and violacein analogues through an increase in the formation and secretion of outer membrane vesicles, FIG. 6A showing the mechanism of formation of an outer membrane vesicle in *E. coli*, FIGS. 6B and 6C showing the results of production of β-carotene and deoxyviolacein, respectively, FIGS. 6D and 6E showing TEM (upper panel) and SEM (lower panel) images of the BTC1 strain introduced with sRNA that suppresses expression of rffD and rfaD and the DVIO strain introduced with sRNA that suppresses expression of rfaI, respectively, FIG. 6F showing SEM images for analysis after purification of outer cell vesicles formed in the BTC1 strain introduced with sRNA that suppresses expression of rffD and rfaD (upper panel) and of outer cell vesicles formed in the DVIO strain introduced with sRNA that suppresses expression of rfaI (lower panel), FIG. 6G showing the results of production of β-carotene when both the inner and outer membrane vesicles are formed, FIG. 6H showing the results of production of deoxyviolacein when a combination of cell morphology modification and formation of inner and outer membrane vesicles is applied, and FIGS. 6I and 6J showing TEM (upper panel) and SEM (lower panel) images of the BTC1 strain introduced with sRNA that suppresses expression of rffD and rfaD and introduced with cav1-plsBC, and the DVIO strain introduced with sRNA that suppresses expression of rfaI and introduced with cav1, respectively;

FIGS. 7A to 7L show the results of quantitative analysis of carotenoids and violacein analogues secreted into the culture medium through outer membrane vesicles, FIG. 7A showing β-carotene extracted from the supernatant of the BTC1 strain culture solution introduced with sRNA for the expression of outer membrane vesicles (OMVs), FIG. 7B showing β-carotene extracted from purified outer membrane vesicles, in which OMV designates the BTC1 strain introduced with sRNA that suppresses expression of rffD and rfaD and IMV designates the BTC1 strain introduced with cav1 and plsBC, FIG. 7C showing deoxyviolacein extracted from the supernatant of the DVIO strain culture solution introduced with sRNA for the expression of outer membrane vesicles, FIG. 7D showing deoxyviolacein extracted from purified outer membrane vesicles, in which OMV designates the DVIO strain introduced with sRNA that suppresses expression of rfaI and IMV designates the DVIO strain introduced with cav1, FIG. 7E showing microscope images of the aggregates composed of cells, outer membrane vesicles, and deoxyviolacein crystals remaining after water washing during flask culture of DVIO introduced with sRNA that suppresses expression of rfaI, FIGS. 7F and 7G showing the results of flask culture through overexpression of the plsBC gene in β-carotene- and deoxyviolacein-producing strains expressing outer membrane vesicles, respectively, and FIGS. 7H, 7I, 7J, 7K and 7L showing graphs corresponding to the results of total production amount (represented by Tot) and secreted production amount (represented by Sec) of zeaxanthin, astaxanthin, prodeoxyviolacein, proviolacein, and violacein, respectively, upon expression of outer membrane vesicles or inner membrane vesicles, in which error bars represent mean±standard deviation (n=3), *$P<0.05$, $P<0.01$, *$P<0.001$, NS (not significant) $P \geq 0.05$ being determined by a two-tailed Student's t-test; and FIGS. 8A to 8G show the results of production of respective hydrophobic materials, such as astaxanthin, beta-carotene, zeaxanthin, proviolacein, prodeoxyviolacein, violacein, and deoxyviolacein, over time upon fed-batch fermentation using the recombinant microorganism of the present invention.

DETAILED DESCRIPTION OF THE INVENTION

Unless otherwise defined, all technical and scientific terms used herein have the same meanings as those typically understood by those skilled in the art to which the present invention belongs. Generally, the nomenclature used herein is well known in the art and is typical.

Unless otherwise indicated, nucleic acids are set forth in a 5'→direction from left to right and amino acids are set forth in an N-terminal→C-terminal direction from left to right. Numerical ranges recited within the specification are inclusive of the numbers defining the range, including each integer or any non-integer fraction within the defined range.

To date, many attempts have been made to increase the production of colored natural materials by manipulating the metabolic network of microorganisms, but some limitations are imposed thereon due to the characteristics of materials that accumulate in cells. In the present invention, the amounts of hydrophobic pigments that are produced are drastically increased by engineering the cell membrane in various ways to enlarge the area of the cell membrane, to expand the cell membrane by creating a structure within the cell, or to trap the corresponding materials in the vesicles to release the same out of the cell.

In an embodiment of the present invention, natural pigments such as carotenoids and violacein analogues were produced in *E. coli*. Carotenoids and violacein analogues are lipophilic materials that, when produced in *E. coli*, accumulate in the cell membrane, rather than in the cytoplasm or extracellularly. Based thereon, the cell membrane area is increased and vesicles are formed inside and outside the cells so as to expand the space in which the natural lipophilic pigment material is able to accumulate. Specifically, an *E. coli* strain producing each of three types of carotenoids and four types of violacein analogues was constructed, after which a change in the production amount depending on an increase in the cell membrane area and the formation of vesicles was observed. Moreover, the synergistic effect of individual elements of the present invention in the production of all materials was tested and verified. The strategy used in the present study may be efficiently applied to research into the production not only of natural pigments but also of a variety of different lipophilic materials, such as antioxidants, antibiotics, cosmetic additives, anticancer agents, food additives, and nutritional supplements, in *E. coli*.

In an embodiment of the present invention, a hydrophobic-material-producing strain capable of producing natural pigments, such as carotenoids and violacein, which are most frequently used in industry, was constructed, and with the goal of increasing the ability to produce a hydrophobic material, the hydrophobic-material-producing strain was subjected to cell-membrane engineering in order to exhibit characteristics such as i) an increase in the cell membrane area, ii) an increase in the formation and secretion of outer membrane vesicles, or iii) an increase in the formation of inner membrane vesicles. In order to impart the above characteristics to the strain through cell-membrane engineering, cell-morphology-related genes and outer-membrane-vesicle-related genes were screened, and when suppressing the expression of the corresponding gene through treatment with sRNA targeting the cell-morphology-related gene or the outer-membrane-vesicle-related gene or when overexpressing the inner-membrane-vesicle-related gene, it was confirmed that the ability of the strain to produce a natural pigment was significantly increased, and also that a combination of gene expression suppression and overexpression exhibited a synergistic effect.

In an embodiment of the present invention, it has been confirmed that an increase in the cell membrane area through suppression of cell-morphology-related genes in *E. coli*, an increase in the formation and secretion of outer membrane vesicles through suppression of outer-membrane-vesicle-related genes, and an increase in the formation of inner membrane vesicles through overexpression of inner-membrane-vesicle-related genes resulted in a significant improvement in ability to produce natural pigments, which are representative hydrophobic materials accumulating in the cell membrane. In general, it is readily understood that hydrophobic materials accumulate in the hydrophobic cell membrane or the inner and outer membranes of vesicles, so various hydrophobic materials that may be produced through microorganisms, in addition to natural pigments, may be produced at a level equivalent to the ability to produce natural pigments.

Therefore, the present invention pertains to a recombinant microorganism for producing a hydrophobic material, which is subjected to cell-membrane engineering in order to be imparted with at least one characteristic among an increase in the cell membrane area, an increase in the formation and secretion of outer membrane vesicles, and an increase in the formation of inner membrane vesicles.

As used herein, the term "cell-membrane engineering" refers to a technique for enhancing or reducing conventional cell-membrane characteristics of cells using genetic recombination technology or the like or for conferring new characteristics thereto. In the present invention, cell-membrane engineering was performed using suppression, overexpression and/or introduction of genes, and was intended to confer the characteristics of increasing the cell membrane area, increasing the formation and secretion of outer membrane vesicles, and/or increasing the formation of inner membrane vesicles.

In an embodiment of the present invention, the above characteristics were conferred by performing cell-membrane engineering through expression suppression, introduction, or overexpression of genes in a recombinant microorganism for producing a hydrophobic material.

Accordingly, an aspect of the present invention pertains to a recombinant microorganism for producing a hydrophobic material, in which at least one gene among a cell-morphology-related gene and an outer-membrane-vesicle-related gene is suppressed and/or in which an inner-membrane-vesicle-related gene is overexpressed or introduced.

In the present invention, the recombinant microorganism is engineered by performing suppression of at least one gene among a cell-morphology-related gene and an outer-membrane-vesicle-related gene and/or overexpression or introduction of an inner-membrane-vesicle-related gene in order to impart the recombinant microorganism with at least one characteristic among i) an increase in the cell membrane area, ii) an increase in the formation and secretion of outer membrane vesicles, and iii) an increase in the formation of inner membrane vesicles.

In the present invention, the hydrophobic material may be characterized by accumulating in the cell membrane. Examples of the hydrophobic material may include, but are not limited to, natural pigments, antioxidants, antibiotics, cosmetic additives, anticancer agents, food additives, and nutritional supplements.

In the present invention, the natural pigment is a pigment or an analogue thereof that is not artificially synthesized but is obtainable from nature, and examples thereof may include carotenoids, violacein, etc., and specific examples thereof may include, but are not limited to, lycopene, β-carotene, zeaxanthin, astaxanthin, proviolacein (PVIO), prodeoxyviolacein (PDVIO), deoxyviolacein (DVIO), violacein (VIO), and the like.

Examples of the antioxidant material may include, but are not limited to, quercetin, dihydroquercetin, kaempferol, dihydrokaempferol, astaxanthin, resveratrol, tocopherol, tocotrienol, coenzyme Q10, apigenin, and the like.

Examples of the cosmetic additive may include, but are not limited to, aloesin, vitamin A, ceramide, pantothenate, panthenol, lupeol, squalene, eucalyptol, valencene, and the like.

Examples of the food additive may include, but are not limited to, carminic acid, β-carotene, lycopene, and the like.

Examples of the nutritional supplement may include, but are not limited to, silymarin, lutein, vitamins, coenzyme-Q10, resveratrol, omega-3 polyunsaturated fatty acids, ubiquinone, glucosamine, luteolin, and the like.

In the present invention, the hydrophobic material is preferably selected from the group consisting of astaxanthin, beta-carotene, zeaxanthin, proviolacein, prodeoxyviolacein, deoxyviolacein and violacein.

As used herein, the term "cell-morphology-related gene" refers to a gene involved in maintaining the morphology of a cell, and in an embodiment of the present invention, expression of the cell-morphology-related gene was suppressed in order to increase the area of the cell membrane in which the hydrophobic material accumulates by making the filamentous recombinant cell morphology more irregular or spherical. In the present invention, any cell-morphology-related gene may be included without limitation, so long as it is a gene capable of increasing the cell area by modifying cell morphology upon suppression of expression thereof. Such a gene may be easily selected by those skilled in the art depending on the type of recombinant microorganism that is used, and is preferably selected from among genes necessary for forming, maintaining, or modifying the inherent cell morphology of the recombinant microorganism, but the present invention is not limited thereto.

In the present invention, the cell-morphology-related gene may be, for example, a gene involved in cell division or a gene involved in synthesis or maintenance of a cytoskeleton/cell wall, but is not limited thereto.

In the present invention, the gene involved in cell division may be a gene encoding a prokaryote-derived enzyme group involved in cell division, including, for example, cell division proteins (e.g. Fts proteins, etc.) and cell division inhibitors (e.g. MinC, MinD, etc.), but is not limited thereto.

In the present invention, the gene involved in the synthesis or maintenance of the cytoskeleton/cell wall may be a gene encoding a prokaryote-derived enzyme group, including, for example, penicillin-binding protein (PBP), cell-shape-determining protein (MreB, MreC, etc.), peptidoglycan D,D-transpeptidase (MrdA, PbpA, etc.), peptidoglycan glycosyltransferase (MrdB, etc.), cytoskeleton protein (RodZ, etc.), and the like, but is not limited thereto.

In an embodiment of the present invention, after preparation of recombinant *E. coli* to express a natural pigment, cell-membrane engineering was performed by suppressing the expression of 16 types of screened cell-morphologyrelated genes (Table 4). For example, when the recombinant microorganism is *E. coli*, the cell-morphology-related gene may be selected from the group consisting of rodZ (cytoskeleton protein), ftsA (cell division protein), ftsB (cell division protein), ftsI (peptidoglycan D,D-transpeptidase), ftsL (cell division protein), ftsQ (cell division protein), ftsW (probable peptidoglycan glycosyltransferase), ftsZ (cell division protein), minD (septum site-determining protein), mrdA (peptidoglycan D,D-transpeptidase), mrdB (peptidoglycan glycosyltransferase), mreB (cell-shape-determining protein), mreC (cell-shape-determining protein), zipA (cell division protein), murE (UDP-N-acetylmuramoyl-L-alanyl-D-glutamate-2,6-diaminopimelate ligase), pbpC (penicillin-binding protein 1C), and combinations thereof, but is not limited thereto.

More preferably, for example, deoxyviolacein-producing recombinant *E. coli* is characterized in that the expression of an mrdB gene, which is the cell-morphology-related gene, is suppressed.

In the present invention, the cell-morphology-related gene may be appropriately changed into or selected from a gene corresponding to the cell-morphology-related gene of *E. coli* suppressed in the embodiment of the present invention or a gene performing substantially the same function, depending on the microorganism that is used and the hydrophobic material to be produced.

As used herein, the term "outer-membrane-vesicle-related gene" refers to a gene involved in the formation or secretion of outer membrane vesicles. In the present invention, the outer-membrane-vesicle-related gene may be an endogenous gene of a microorganism. In an embodiment of the present invention, when releasing the hydrophobic material accumulated in the cell through outer membrane vesicles by suppressing the expression of a gene that plays a role in maintaining the connection between the outer membrane and the inner membrane of the cell or the peptidoglycan layer of the cell, which is the outer-membrane-vesicle-related gene, the ability to produce the hydrophobic material was significantly improved. In the present invention, any outer-membrane-vesicle-related gene may be included without limitation, so long as it is a gene capable of improving the formation and secretion of outer membrane vesicles upon suppression of expression thereof. Such a gene may be easily selected depending on the type of recombinant microorganism that is used, and is preferably a gene involved in maintaining the connection between the outer membrane and the inner membrane of the cell or the peptidoglycan layer of the cell, but is not limited thereto.

In the present invention, the outer-membrane-vesicle-related gene may be an outer membrane/peptidoglycan structure maintenance-related gene, an outer-membrane protein expression gene, or a cell-membrane metabolic-network-related gene, but is not limited thereto.

In the present invention, the outer membrane/peptidoglycan structure maintenance-related gene may be a gene encoding a prokaryote-derived enzyme group that contributes to maintenance of the outer membrane/peptidoglycan structure, such as lipoprotein (Lpp), Tol-Pal system protein (TolB, Pal, TolA, TolR, etc.), lipopolysaccharide core biosynthesis protein, lipopolysaccharide core heptosyltransferase, lipid A biosynthesis lauroyltransferase, or the like, but is not limited thereto.

In the present invention, the outer-membrane protein expression gene may be a gene encoding a prokaryote-derived enzyme group that contributes to expression of the outer-membrane protein, such as outer-membrane protein A (OmpA), outer-membrane protein C (OmpC), outer-membrane protein F (OmpF), OprF (OmpA homologue), envelope protein (RagA, RagB, etc.), or the like, but is not limited thereto.

In the present invention, the cell-membrane metabolic-network-related gene may be related with a expression of anti-sigma factor.

In the present invention, the cell-membrane metabolic-network-related gene may be a gene encoding a prokaryote-derived cell-membrane metabolic-network enzyme group, such as quinolone signal (PQS), anti-sigma-E factor, sigma factor H (AlgU), chaperone-protease (DegP), or the like, but is not limited thereto.

In an embodiment of the present invention, after preparation of recombinant *E. coli* to express a natural pigment, cell-membrane engineering was performed by suppressing the expression of 26 types of screened outer-membrane-vesicle-related genes (Table 7). For example, when the recombinant microorganism is *E. coli*, the outer-membrane-vesicle-related gene may be selected from the group consisting of rseA (anti-sigma-E factor), rseB (sigma-E factor regulatory protein), rffD (UDP-N-acetyl-D-mannosamine dehydrogenase), rffC (dTDP-fucosamine acetyltransferase), rffA (dTDP-4-amino-4,6-dideoxygalactose transaminase), ompR (DNA-binding dual transcriptional regulator), gmhB (D-glycero-beta-D-manno-heptose-1,7-bisphosphate 7-phosphatase), lpxL (lipid A biosynthesis lauroyltransferase), lpxM (lipid A biosynthesis myristoyltransferase), ompA (outer-membrane protein), ompC (outer-membrane protein), rfaB (lipopolysaccharide 1,6-galactosyltransferase), rfaC (lipopolysaccharide heptosyltransferase 1), rfaD (ADP-L-glycero-D-manno-heptose-6-epimerase), rfaE (bi-functional protein HldE), rfaG (lipopolysaccharide core biosynthesis protein), rfaI (lipopolysaccharide 1,3-galactosyltransferase), rfaJ (lipopolysaccharide 1,2-glucosyltransferase), rfaK (lipopolysaccharide 1,2-N-acetylglucosaminetransferase), rfaP (lipopolysaccharide core heptose (I) kinase), rfaQ (lipopolysaccharide core heptosyltransferase), rfaY (lipopolysaccharide core heptose (II) kinase), rfbA (glucose-1-phosphate thymidylyltransferase 1), rffH (glucose-1-phosphate thymidylyltransferase 2), wzxE (ECA polysaccharide chain length modulation protein), pnp (polyribonucleotide nucleotidyltransferase), tolA (colicin import membrane protein), tolB (Tol-Pal system periplasmic protein), tolC (outer-membrane protein), tolR (biopolymer transport protein), nlpI (lipoprotein), nlpD (murein hydrolase activator), ompF (outer-membrane pore protein), pal (peptidoglycan-associated outer membrane lipoprotein), degS (serine endoprotease), degP (serine endoprotease), tatC (sec-independent protein translocase protein), lpp (murein lipoprotein), and combinations thereof, but is not limited thereto.

For example, in recombinant *E. coli* producing carotenoids such as astaxanthin, β-carotene, or zeaxanthin, expression of at least one gene selected from among rfaD, rffD and rfaQ may be suppressed, and preferably, expression of rffD and rfaD genes have been suppressed.

In another example, in recombinant *E. coli* producing violacein and analogues thereof such as violacein, prodeoxyviolacein, proviolacein, or deoxyviolacein, expression of an rfaI or rfaQ gene may be suppressed, and preferably, expression of an rfaI gene may be suppressed.

In the present invention, the outer-membrane-vesicle-related gene may be appropriately changed into or selected from a gene corresponding to the outer-membrane-vesicle-related gene suppressed in the embodiment of the present invention or a gene performing substantially the same function, depending on the microorganism that is used and the hydrophobic material to be produced.

As used herein, the term "inner-membrane-vesicle-related gene" refers to a gene involved in the formation of inner membrane vesicles, and in an embodiment of the present invention, since E. coli, which is a prokaryote having no inner membrane vesicle system, was used, cell-membrane engineering was performed so as to form an inner membrane by introducing a human-derived caveola gene of the eukaryote-derived inner membrane vesicle system. In the present invention, any inner-membrane-vesicle-related gene may be selected and used without limitation, so long as it is a gene capable of improving the formation of inner membrane vesicles. In the present invention, when the recombinant microorganism for producing a hydrophobic material is a microorganism having no inner membrane vesicle system, another eukaryote- or prokaryote-derived inner membrane vesicle system gene that forms an inner membrane may be introduced. In the present invention, when the recombinant cell for producing a hydrophobic material inherently includes an inner membrane vesicle system, the inner membrane vesicle gene of the cell itself may be overexpressed, or another eukaryote- or prokaryote-derived inner membrane vesicle system gene may be additionally introduced.

In the present invention, the inner-membrane-vesicle-related gene may be a eukaryotic-cell-derived caveola system gene or a clathrin-epsin system gene, or may be a prokaryotic-cell-derived mgs-dgs system gene, and may more specifically be selected from the group consisting of cav1 (caveolin-1), cav2 (caveolin-2), cav3 (caveolin-3), EPN1 (epsin1), CLINT1 (epsinR), CLTC (clathrin heavy chain 1), CLTCL1 (clathrin heavy chain 2), CLTA (clathrin light chain A), CLTB (clathrin light chain B), AP180, AP2, almgs (1,2-diacylglycerol 3-glucosyltransferase), aldgs (1,2-diacylglycerol-3-glucose (1-2)-glucosyltransferase producing diglucosyldiacylglycerol), and combinations thereof, but is not limited thereto.

In the present invention, in recombinant E. coli producing carotenoids such as astaxanthin, β-carotene, and zeaxanthin, a cav1 gene may be introduced or overexpressed.

In the present invention, in recombinant E. coli producing violacein or analogues thereof (proviolacein, prodeoxyviolacein, and deoxyviolacein), a cav1 gene may be introduced or overexpressed.

In the present invention, the inner-membrane-vesicle-related gene may be appropriately changed or selected depending on the microorganism that is used and the hydrophobic material to be produced.

In an embodiment of the present invention, it has been confirmed that the combination of suppression of expression of the cell-morphology-related gene, suppression of expression of the outer-membrane-vesicle-related gene, and introduction of the inner-membrane-vesicle-related gene showed a synergistic effect, resulting in a greater increase in the production amount.

In the present invention, characteristics such as an increase in the cell membrane area, an increase in the formation and secretion of outer membrane vesicles, and an increase in the formation of inner membrane vesicles may be exhibited together through cell-membrane engineering depending on the type of recombinant microorganism and the type, amount, expression conditions, etc. of the hydrophobic material to be produced.

In the present invention, suppression of expression of the cell-morphology-related gene, suppression of expression of the outer-membrane-vesicle-related gene, and introduction or overexpression of the inner-membrane-vesicle-related gene may be combined depending on the type of recombinant microorganism and the type, amount, expression conditions, etc. of the hydrophobic material to be produced, and genes belonging to individual related genes may be combined.

In the present invention, the recombinant microorganism is characterized in that i) at least one gene selected from the group consisting of mrdB, rffD, rfaD, and rfaI is suppressed or knocked down, and/or ii) a cav1 gene has been introduced or overexpressed.

Combinations of suppression and introduction/overexpression of genes showing the greatest production ability in the recombinant microorganism for producing each hydrophobic material confirmed in the embodiment of the present invention are as follows: astaxanthin: rffD & rfaD knockdown (OMV);
  beta-carotene: rffD & rfaD knockdown (OMV);
  zeaxanthin: rffD & rfaD knockdown (OMV);
  proviolacein: rfaI knockdown & cav1 overexpression (OMV & IMV);
  prodeoxyviolacein: rfaI knockdown (OMV);
  violacein: rfaI knockdown & cav1 overexpression (OMV & IMV); and
  deoxyviolacein: rfaI knockdown & cav1 overexpression (OMV & IMV).

Therefore, in the present invention, in a recombinant microorganism that produces a carotenoid pigment group, it is most preferable to simultaneously suppress the expression of rfaD and rffD, but the present invention is not limited thereto.

In the present invention, in a recombinant microorganism that produces violacein and analogues thereof, it is most preferable to suppress the expression of rfaI and simultaneously introduce the cav1 gene or induce overexpression thereof, but the present invention is not limited thereto.

The recombinant strain for producing a hydrophobic material according to the present invention may be imparted with at least one characteristic among an increase in the cell membrane area, an increase in the formation and secretion of outer membrane vesicles, and an increase in the formation of inner membrane vesicles.

In an embodiment of the present invention, expression of a plsBC gene as a lipid synthase gene was amplified in order to facilitate lipid supply in response to the increase in the cell membrane area, the increase in the formation and secretion of outer membrane vesicles, and the increase in the formation of inner membrane vesicles. As such, a remarkable increase in the ability to produce carotenoid pigments was confirmed.

In the present invention, the recombinant microorganism for producing a hydrophobic material may be additionally characterized in that the lipid synthase gene is overexpressed.

For example, when the microorganism is E. coli, the overexpression of the lipid synthase gene may be overexpression of the plsBC gene.

As used herein, the term "suppression of gene expression" refers to suppressing or regulating the transcription or translation of the gene to be suppressed to thereby reduce or block expression of the encoding protein or to prevent the protein from properly functioning to thus lose the function of the gene. In the present invention, the term "suppression" may be used interchangeably with "knockdown". In the present invention, expression of the cell-morphology-related gene may be suppressed in order to increase the cell membrane area, and in order to increase the formation and secretion of outer membrane vesicles, expression of the outer membrane/peptidoglycan structure maintenance-related gene, the outer-membrane protein expression gene, or the cell-membrane metabolic-network-related gene may be suppressed. In the present invention, the suppression of gene expression may be performed through a variety of conventionally known methods. For example, gene expression may be suppressed through gene editing using restriction enzymes, ZFN, TALEN, or CRISPR/Cas, antisense oligonucleotides (Nature Reviews Drug Discovery 11 (2): 125-40), ribozyme (Human Molecular Genetics, 7 (10): 1649-1653), RNA interference technology using siRNA, miRNA, shRNA, etc., synthetic regulatory sRNA (Na et al., Nat. Biotechnol. 2013, 31(2):170-174), etc., but the present invention is not limited thereto.

As used herein, the term "gene introduction" refers to introduction of a new target gene or a vector including the same into a target cell or microorganism. In an embodiment of the present invention, for gene introduction, a gene encoding a natural pigment was introduced into $E.$ $coli$ using a plasmid vector in order to construct a natural-pigment-producing strain, and an inner-membrane-vesicle-related gene was introduced into a recombinant microorganism using a plasmid vector in order to promote the formation of inner membrane vesicles. In the present invention, the gene may be introduced into a recombinant microorganism through any of various methods known in the related art. In the present invention, the introduction is preferably introduction into a microorganism using a vector, but the present invention is not limited thereto. In the present invention, a gene may be directly introduced into the genome of a host cell, and may thus be present as a chromosomal factor. It will be apparent to those skilled in the art to which the present invention belongs that, even when the gene is inserted into the genome chromosome of the host cell, the same effect as when the recombinant vector is introduced into the host cell may be exhibited.

As used herein, the term "overexpression" of a gene means that expression of the gene is increased compared to an unmodified microorganism, leading to increased intracellular concentrations of ribonucleic acids, proteins or enzymes compared to the unmodified microorganism. A variety of conventionally known methods for overexpression of a gene may be selected and performed without limitation by those skilled in the art.

Examples of conventionally known techniques for overexpression are as follows:
  increasing the number of gene copies in a microorganism, in which a gene is encoded chromosomally or extrachromosomally, and when a gene is located on a chromosome, several copies of the gene may be introduced on the chromosome through recombination methods (including gene replacement) known to those skilled in the art, whereas when a gene is located extrachromosomally, it may be carried by various types of plasmids that differ in the replication origin in the cell and the number of copies thereof, these plasmids being present in microorganisms in 1 to 5 copies, about 20 copies, or a maximum of 500 copies, depending on the properties of the plasmid: low-copy-number plasmids having dense replication (pSC101, RK2), low-copy-number plasmids (pACYC, pRSF1010), or high-copy-number plasmids (pSK bluescript II);
  using promoters that lead to high gene expression, in which promoters, for example, Ptrc, Ptac, Plac, or lambda promoters PR and PL, may be widely used, but the present invention is not limited thereto, said promoters being "inducible" by certain compounds or under certain external conditions such as temperature or light, and said promoters being homologous or heterologous;
  attenuating the activity or expression of a specific or non-specific transcriptional repressor of a gene;
  using elements that stabilize the corresponding messenger RNA (Carrier and Keasling, 1999) or elements that stabilize proteins (e.g. GST tags, GE Healthcare); and
  altering the sequence of a 5' untranslated region (5' UTR), but the present invention is not limited thereto.

As used herein, the term "vector" refers to a nucleic acid molecule containing a nucleic acid sequence operably linked to a suitable expression control sequence capable of expressing a gene in a suitable host. The vector may be a plasmid, a phage particle, or a potential genomic insert. Upon transformation into an appropriate host, the vector may replicate and function independently of the host genome, or in some cases may be integrated into the genome itself. Since a plasmid is currently the most commonly used form of vector, "plasmid" and "vector" are sometimes used interchangeably in the context of the present invention. However, the present invention includes other forms of vectors having functions equivalent to those known or becoming known in the art. Examples of protein expression vectors used in $E.$ $coli$ may include pET series, pCDF series, pRSF series, pACYC series, and pCOLA series, available from Novagen (USA); pBAD series, available from Invitrogen (USA); pHCE or pCOLD, available from Takara (Japan); pACE series, available from Xenofocus (Korea); pTacl5K, pTrc99A, pTacCDFS, and pTrcCDFS series, available from KAIST (Korea); pBBR1MCS series, which may be used in a wide range of strains, and the like. In $Bacillus$ $subtilis$, protein expression may be realized by inserting a target gene into a certain portion of the genome, or a pHT vector available from MoBiTech (Germany) or the like may be used. In mold or yeast, protein expression is possible using genome insertion or self-replicating vectors. A plant protein expression vector may be used using a T-DNA system such as $Agrobacterium$ $tumefaciens$ or $Agrobacterium$ $rhizogenes$. Typical expression vectors for expression of a mammalian cell culture may be based on, for example, pRK5 (EP 307,247), pSV16B (WO 91/08291), and pVL1392 (Pharmingen).

The representation "expression control sequence" refers to a DNA sequence that is essential for the expression of an operably linked coding sequence in a certain host organism. Such a control sequence includes a promoter for transcription, an arbitrary operator sequence for regulating such transcription, a sequence encoding a suitable mRNA ribosome-binding site, and a sequence for regulating termination of transcription and translation. For example, a control sequence suitable for prokaryotes includes a promoter, an arbitrary operator sequence, and a ribosome-binding site. A eukaryotic cell includes a promoter, a polyadenylation signal, and an enhancer. The factor that most affects the expression level of a gene in the plasmid is a promoter. Preferred examples of the promoter for high expression include a SRα promoter and a cytomegalovirus-derived promoter.

In order to express the DNA sequence of the present invention, any of a wide variety of expression control sequences may be used in the vector. Examples of useful expression control sequences include, in addition to the promoters described above, early and late promoters of SV40 or adenovirus, lac system, trp system, TAC or TRC system, T3 and T7 promoters, major operator and promoter regions of phage lambda, control regions of fd coding protein, promoters for 3-phosphoglycerate kinase or other glycolytic enzymes, promoters of the phosphatase, such as Pho5, promoters of yeast alpha-mating systems, and other constitutive and inducible promoter sequences known to control the expression of genes in prokaryotic or eukaryotic cells or viruses thereof, and various combinations thereof. The T7 RNA polymerase promoter (may be useful in the expression of proteins in *E. coli*.

It should be naturally understood that not all vectors and expression control sequences function equally in expressing the DNA sequences of the present invention. Likewise, not all hosts function equally in the same expression system. However, those skilled in the art may make an appropriate selection among various vectors, expression control sequences, and hosts without departing from the scope of the present invention without undue experimental burden. For example, in selecting a vector, the host has to be taken into consideration. This is because the vector has to be replicated therein. The number of copies of the vector, the ability thereof to control the number of copies, and the expression of other proteins encoded by the vector, for example antibiotic markers, also have to be taken into consideration. In selecting the expression control sequence, various factors have to be taken into consideration. For example, the relative strength of sequences, the likelihood of control thereof, and compatibility with DNA sequences of the present invention, etc., should be taken into account, particularly with regard to possible secondary structures. The single-cell host should be selected in consideration of factors, such as the selected vector, the toxicity of the product encoded by the DNA sequence of the present invention, the secretory properties, the ability to correctly fold the protein, culture and fermentation requirements, and ease of purification of the product encoded by the DNA sequence of the present invention from the host. Within the scope of these factors, those skilled in the art may select various combinations of vectors, expression control sequences, and hosts capable of expressing the DNA sequences of the present invention in fermentation or large-scale animal culture. As a screening method for cloning cDNA through expression cloning, a binding method, a panning method, a film emulsion method, etc. may be applied.

In such vectors, a nucleic acid is said to be "operably linked" when placed in a functional relationship with another nucleic acid sequence. It may be a gene and control sequence(s) linked in such a manner that an appropriate molecule (e.g. a transcriptional activation protein), when bound to the control sequence(s), allows for gene expression. For example, DNA for a pre-sequence or secretory leader is operably linked to DNA for a polypeptide when expressed as a preprotein that participates in secretion of the polypeptide, a promoter or enhancer is operably linked to a coding sequence when affecting the transcription of the sequence, a ribosome-binding site is operably linked to a coding sequence when affecting the transcription of the sequence, or a ribosome-binding site is operably linked to a coding sequence when positioned to facilitate translation. In general, "operably linked" means that the linked DNA sequence is in contact therewith, and also that the secretory leader is in contact therewith and is present in the reading frame. However, the enhancer need not be in contact therewith. The linkage of these sequences is accomplished by ligation at convenient restriction enzyme sites. When no such site exists, a synthetic oligonucleotide adapter or linker according to a typical method is used.

The recombinant vector may be introduced into a host cell using a method such as transformation or transfection. As used herein, the term "transformation" refers to the introduction of DNA into a host such that the DNA becomes replicable either as an extrachromosomal factor or by chromosomal integration. As used herein, the term "transfection" means that an expression vector is accepted by a host cell, regardless of whether or not any coding sequence is actually expressed.

As is well known in the art, in order to increase the expression level of a transfected gene in a recombinant cell, the corresponding gene has to be operably linked to the transcriptional and translational expression control sequence that functions in the selected expression host. Preferably, the expression control sequence and the corresponding gene are contained in a single expression vector including both the bacterial selection marker and the replication origin. When the expression host is a eukaryotic cell, the expression vector may further include an expression marker useful in the eukaryotic expression host.

In the present invention, as the microorganism for producing a hydrophobic material, prokaryotic cells such as *E. coli, Bacillus subtillis*, etc., which may be cultured at a high concentration in a short time, are easy to genetically manipulate, and have well-known genetic and physiological characteristics, have been widely used. In addition to prokaryotic cells, recently, single-celled eukaryotic cells, such as yeast (*Pichia pastoris, Saccharomyces cerevisiae, Hansenula polymorpha*, etc.), filamentous fungi, insect cells, plant cells, cells of higher organisms such as mammals, etc., may be used as the host cells for the production of recombinant proteins in order to solve problems of post-translational modification of proteins, secretory process, active three-dimensional structure, and active state of proteins. The use not only of *E. coli* or recombinant microorganism exemplified in Examples but also of other host cells will be readily apparent to those skilled in the art. For example, a CHO cell line, a HEK cell line, etc. may be used as a host cell for expression, but the present invention is not limited thereto.

In the present invention, a wide variety of microorganism/host cell and vector combinations may be used. Expression vectors suitable for eukaryotic hosts include, for example, expression control sequences derived from SV40, bovine papillomavirus, adenovirus, adeno-associated virus, cytomegalovirus, and retrovirus. Expression vectors that may be used in bacterial hosts include bacterial plasmids, exemplified by those obtained from *E. coli*, such as pBluescript, pGEX2T, pUC vector, col E1, pCR1, pBR322, pMB9 and derivatives thereof, broad-host-range bacterial plasmids, such as pBBR1MCS and derivatives thereof, bacterial plasmids, such as pET, pCDF, pRSF, pACYC, pCOLA, pBAD, pHCE, pCOLD, pACE, pTacl5K, pTrc99A, pTacCDFS, pTrcCDFS and derivatives thereof, plasmids useful across a wide host range, such as RP4, phage DNA exemplified by a wide variety of phage lambda derivatives, such as λ and λNM989, and other DNA phages, such as M13 and filamentous single-stranded DNA phages. The expression vectors useful for yeast cells are 2p plasmids and derivatives thereof. A useful vector for insect cells is pVL 941.

In the present invention, the recombinant microorganism for producing a hydrophobic material is a microorganism that includes an endogenous or exogenous gene encoding a hydrophobic material and thus has the ability to express a hydrophobic material. When the gene encoding the hydrophobic material is an exogenous gene, the expression microorganism or the recombinant expression microorganism imparted with production ability through introduction into the expression cell may be subjected to cell-membrane engineering. Various methods of introducing an exogenous gene into a microorganism are known in the related art, non-limiting examples of which include transformation, transduction, etc., and an appropriate method may be selected by those skilled in the art to prepare microorganisms that produce hydrophobic materials.

In the present invention, the recombinant microorganism is preferably selected from the group consisting of *E. coli, Rhizobium, Bifidobacterium, Rhodococcus, Candida, Erwinia, Enterobacter, Pasteurella, Mannheimia, Actinobacillus, Aggregatibacter, Xanthomonas, Vibrio, Pseudomonas, Azotobacter, Acinetobacter, Ralstonia, Agrobacterium, Rhodobacter, Zymomonas, Bacillus, Staphylococcus, Lactococcus, Streptococcus, Lactobacillus, Clostridium, Corynebacterium, Streptomyces, Bifidobacterium, Cyanobacterium,* and *Cyclobacterium,* but is not limited thereto.

As used herein, the term "endogenous gene" means that the gene was present in the microorganism before any genetic modification. The endogenous gene may be overexpressed by introducing a heterologous sequence in addition to or in place of the endogenous regulatory element, or by introducing one or more complementary copies of the gene into a chromosome or plasmid. The endogenous gene may also be modified to modulate the expression and activity of the encoded protein corresponding thereto. For example, a mutation may be introduced into the coding sequence to modify the gene product, or a heterologous sequence may be introduced in addition to or in place of the endogenous regulatory element. Modulation of the endogenous gene may result in up-regulation and/or enhancement of the activity of the gene product, or alternatively, may down-regulate and/or decrease the activity of the endogenous gene product.

Another way to modulate expression is to exchange the endogenous promoter (e.g. a wild-type promoter) of a gene with a stronger or weaker promoter to up- or down-regulate the expression of the endogenous gene. These promoters may be homologous or heterologous. It is well within the ability of those skilled in the art to select appropriate promoters.

Conversely, the term "exogenous gene" means that the gene was introduced into a microorganism by means well known to those skilled in the art and that this gene is not naturally occurring in the microorganism. The exogenous gene may be integrated into the host chromosome, or may be expressed extrachromosomally by a plasmid or vector. A variety of plasmids, which differ in the replication origin in the cell and the number of copies thereof, are well known in the art. These genes may be homologous.

As used herein, the term "homologous gene" is not limited to designating genes having a theoretical common genetic ancestor, but includes genes that, despite being genetically unrelated, have evolved to encode proteins that perform similar functions and/or have similar structures. Thus, the term "functional homologue" for the purposes of the present invention relates to the fact that certain enzymatic activity may be provided not only by a specific protein having a defined amino acid sequence, but also by proteins of similar sequence from other (un)related microorganisms.

Using references given in GenBank for known genes, those skilled in the art may determine equivalent genes in other organisms, bacterial strains, yeast, fungi, mammals, plants, and the like. This routine work is advantageously conducted using consensus sequences that may be determined by performing sequence alignment with genes derived from other microorganisms and designing degenerate probes to clone the corresponding gene in another organism. These routine methods of molecular biology are well known to those skilled in the art.

Another aspect of the present invention pertains to a method of preparing a recombinant microorganism for producing a hydrophobic material including performing cell-membrane engineering through at least one among suppression of at least one gene among a cell-morphology-related gene and an outer-membrane-vesicle-related gene, and overexpression or introduction of an inner-membrane-vesicle-related gene.

In the present invention, the cell-membrane engineering step may be additionally characterized by an increase in the expression of a lipid synthase gene.

For example, when the microorganism is *E. coli*, the increase in the expression of the lipid synthase gene may be additional overexpression of the plsBC gene.

In the present invention, the recombinant microorganism prepared using the method described above may exhibit at least one characteristic among an increase in the cell surface area, an increase in the formation and secretion of outer membrane vesicles, and an increase in the formation of inner membrane vesicles.

The recombinant microorganism prepared using the method of the present invention has at least one characteristic among an increase in the cell surface area, an increase in the formation and secretion of outer membrane vesicles, and an increase in the formation of inner membrane vesicles, thereby greatly increasing the ability of the recombinant microorganism to produce hydrophobic material that accumulates in the cell membrane.

In the present invention, the cell-morphology-related gene may be, for example, a gene involved in cell division or a gene involved in synthesis or maintenance of a cytoskeleton/cell wall, but is not limited thereto.

In the present invention, the gene involved in cell division may be a gene encoding a prokaryote-derived enzyme group involved in cell division, including, for example, cell division proteins (e.g. Fts proteins, etc.) and cell division inhibitors (e.g. MinC, MinD, etc.), but is not limited thereto.

In the present invention, the gene involved in synthesis or maintenance of the cytoskeleton/cell wall may be a gene encoding a prokaryote-derived enzyme group, including, for example, penicillin-binding protein (PBP), cell-shape-determining protein (MreB, MreC, etc.), peptidoglycan D,D-transpeptidase (MrdA, PbpA, etc.), peptidoglycan glycosyltransferase (MrdB, etc.), cytoskeleton protein (RodZ, etc.), and the like, but is not limited thereto.

For example, when the recombinant microorganism is *E. coli*, the cell-morphology-related gene may be selected from the group consisting of rodZ (cytoskeleton protein), ftsA (cell division protein), ftsB (cell division protein), ftsI (peptidoglycan D,D-transpeptidase), ftsL (cell division protein), ftsQ (cell division protein), ftsW (probable peptidoglycan glycosyltransferase), ftsZ (cell division protein), minD (septum site-determining protein), mrdA (peptidoglycan D,D-transpeptidase), mrdB (peptidoglycan glycosyltransferase), mreB (cell-shape-determining protein), mreC (cell-shape-determining protein), zipA (cell division protein), murE (UDP-N-acetylmuramoyl-L-alanyl-D-glutamate-2,6-diaminopimelate ligase), pbpC (penicillin-binding protein 1C), and combinations thereof, but is not limited thereto. In the present invention, when producing deoxyviolacein, it is most preferable to suppress the expression of an mrdB gene.

In the present invention, any outer-membrane-vesicle-related gene may be included without limitation, so long as it is a gene capable of enhancing the formation and secretion of outer membrane vesicles when suppressed, and may be easily selected depending on the type of recombinant microorganism that is used.

In the present invention, the outer-membrane-vesicle-related gene may be an outer membrane/peptidoglycan structure maintenance-related gene, an outer-membrane protein expression gene, or a cell-membrane metabolic-network-related gene, but is not limited thereto.

In the present invention, the outer membrane/peptidoglycan structure maintenance-related gene may be a gene encoding a prokaryote-derived enzyme group that contributes to the maintenance of the outer membrane/peptidoglycan structure, such as lipoprotein (Lpp), Tol-Pal system protein (TolB, Pal, TolA, TolR, etc.), lipopolysaccharide core biosynthesis protein, lipopolysaccharide core heptosyltransferase, lipid A biosynthesis lauroyltransferase, or the like, but is not limited thereto.

In the present invention, the outer-membrane protein expression gene may be a gene encoding a prokaryote-derived enzyme group that contributes to the expression of the outer-membrane protein, such as outer-membrane protein A (OmpA), outer-membrane protein C (OmpC), outer-membrane protein F (OmpF), OprF (OmpA homologue), envelope protein (RagA, RagB, etc.), or the like, but is not limited thereto.

In the present invention, the cell-membrane metabolic-network-related gene may be a gene encoding a prokaryote-derived cell-membrane metabolic-network enzyme group, such as quinolone signal (PQS), anti-sigma-E factor, sigma factor H (AlgU), chaperone-protease (DegP), or the like, but is not limited thereto.

In an embodiment of the present invention, after preparation of recombinant E. coli to express a natural pigment, cell-membrane engineering was performed by suppressing the expression of 26 types of screened outer-membrane-vesicle-related genes (Table 7). In the present invention, when the recombinant microorganism is E. coli, the outer-membrane-vesicle-related gene may be selected from the group consisting of rseA (anti-sigma-E factor), rseB (sigma-E factor regulatory protein), rffD (UDP-N-acetyl-D-mannosamine dehydrogenase), rffC (dTDP-fucosamine acetyltransferase), rffA (dTDP-4-amino-4,6-dideoxygalactose transaminase), ompR (DNA-binding dual transcriptional regulator), gmhB (D-glycero-beta-D-manno-heptose-1,7-bisphosphatase), lpxL (lipid A biosynthesis lauroyltransferase), lpxM (lipid A biosynthesis myristoyltransferase), ompA (outer-membrane protein), ompC (outer-membrane protein), rfaB (lipopolysaccharide 1,6-galactosyltransferase), rfaC (lipopolysaccharide heptosyltransferase 1), rfaD (ADP-L-glycero-D-manno-heptose-6-epimerase), rfaE (bifunctional protein HldE), rfaG (lipopolysaccharide core biosynthesis protein), rfaI (lipopolysaccharide 1,3-galactosyltransferase), rfaJ (lipopolysaccharide 1,2-glucosyltransferase), rfaK (lipopolysaccharide 1,2-N-acetylglucosaminetransferase), rfaP (lipopolysaccharide core heptose (I) kinase), rfaQ (lipopolysaccharide core heptosyltransferase), rfaY (lipopolysaccharide core heptose (II) kinase), rfbA (glucose-1-phosphate thymidylyltransferase 1), rffH (glucose-1-phosphate thymidylyltransferase 2), wzxE (ECA polysaccharide chain-length modulation protein), pnp (polyribonucleotide nucleotidyltransferase), tolA (colicin import membrane protein), tolB (Tol-Pal system periplasmic protein), tolC (outer-membrane protein), tolR (biopolymer transport protein), nlpI (lipoprotein), nlpD (murein hydrolase activator), ompF (outer-membrane pore protein), pal (peptidoglycan-associated outer membrane lipoprotein), degS (serine endoprotease), degP (serine endoprotease), tatC (sec-independent protein translocase protein), lpp (murein lipoprotein), and combinations thereof, but is not limited thereto.

In the present invention, when the recombinant microorganism for producing a hydrophobic material is a microorganism having no inner membrane vesicle system, another eukaryote- or prokaryote-derived inner membrane vesicle system gene that forms an inner membrane may be introduced. In the present invention, when the recombinant cell for producing a hydrophobic material inherently includes an inner membrane vesicle system, the inner membrane vesicle gene of the cell itself may be overexpressed, or another eukaryote- or prokaryote-derived inner membrane vesicle system gene may be additionally introduced. In the present invention, the inner-membrane-vesicle-related gene may be a eukaryotic-cell-derived caveola system gene or a clathrin-epsin system gene, or may be a prokaryotic-cell-derived mgs-dgs system gene, and more specifically may be selected from the group consisting of cav1 (caveolin-1), cav2 (caveolin-2), cav3 (caveolin-3), EPN1 (epsin1), CLINT1 (epsinR), CLTC (clathrin heavy chain 1), CLTCL1 (clathrin heavy chain 2), CLTA (clathrin light chain A), CLTB (clathrin light chain B), AP180, AP2, almgs (1,2-diacylglycerol 3-glucosyltransferase), aldgs (1,2-diacylglycerol-3-glucose (1-2)-glucosyltransferase producing diglucosyldiacylglycerol), and combinations thereof, but is not limited thereto.

In the present invention, the recombinant microorganism may be selected from the group consisting of E. coli, Rhizobium, Bifidobacterium, Rhodococcus, Candida, Erwinia, Enterobacter, Pasteurella, Mannheimia, Actinobacillus, Aggregatibacter, Xanthomonas, Vibrio, Pseudomonas, Azotobacter, Acinetobacter, Ralstonia, Agrobacterium, Rhodobacter, Zymomonas, Bacillus, Staphylococcus, Lactococcus, Streptococcus, Lactobacillus, Clostridium, Corynebacterinum, Streptomyces, Bifidobacterium, Cyanobacterium, and Cyclobacterium.

Still another aspect of the present invention pertains to a method of preparing a hydrophobic material including producing a hydrophobic material by culturing the recombinant microorganism for producing a hydrophobic material according to the present invention or a recombinant microorganism for producing a hydrophobic material prepared using the method described above and obtaining the produced hydrophobic material.

In the present invention, the step of producing the hydrophobic material by culturing the recombinant microorganism for producing a hydrophobic material may be performed without limitation through a variety of conventionally known microorganism culture methods, and culture may be carried out by appropriately selecting the culture medium, culture conditions (temperature, time, physical conditions) and the like depending on the strain, the material to be produced, etc.

As used herein, the term "culture" means culturing a microorganism to obtain the desired efficacy, and the desired efficacy in the present invention is the production of a hydrophobic material. Culture may generally be carried out in an incubator having an appropriate culture medium adapted to the microorganism that is used and containing at least one simple carbon source, and, as necessary, a co-substrate.

In the present invention, the term "culture" may be used interchangeably with "fermentation" in the sense of producing a hydrophobic material through microbial culture.

In the present invention, the step of producing the hydrophobic material by culturing the recombinant microorganism may be performed through fed-batch fermentation.

As used herein, the terms "fed-batch culture" and "fed-batch fermentation" refer to culture/fermentation by intermittently additionally supplying a medium to control the concentration of the culture solution.

The "appropriate culture medium" may include a carbon source, a carbon substrate, a nitrogen source such as peptone, glucose, glycerol, yeast extract, meat extract, malt extract, urea, ammonium sulfate, ammonium chloride, ammonium nitrate, or ammonium phosphate, a phosphorus source such as monopotassium phosphate or dipotassium phosphate, trace elements (e.g. metal salts) such as magnesium salts, cobalt salts, and/or manganese salts, growth factors such as amino acids and vitamins, which are nutrients essential or beneficial to maintenance and/or growth of cells, yeast extracts, antibiotics, and the like. In the present invention, culture may be carried out within an appropriate temperature range in order to produce a hydrophobic material, for example, 30 to 40° C., and preferably 35 to 38° C., but the present invention is not limited thereto, and the culture conditions may vary depending on the species of the host microorganism, the material to be expressed, and the like.

The present invention is intended to increase the ability to produce a hydrophobic material that accumulates in the cell membrane through an increase in the cell membrane area, an increase in the formation and secretion of outer membrane vesicles, or an increase in the formation of inner membrane vesicles by performing cell-membrane engineering. In an embodiment of the present invention, it has been confirmed that the increase in the cell membrane area through suppression of expression of cell-morphology-related genes in $E.$ $coli$, the increase in the formation and secretion of outer membrane vesicles through suppression of expression of outer-membrane-vesicle-related genes, and the increase in the formation of inner membrane vesicles through overexpression of inner-membrane-vesicle-related genes result in greatly increased ability to produce a natural pigment, which is a representative hydrophobic material that accumulates in the cell membrane. In general, since a hydrophobic material accumulates in a hydrophobic cell membrane or the inner and outer membranes of vesicles, it will be obvious that improved ability to produce various hydrophobic materials capable of being produced by microorganisms, in addition to natural pigments, may be exhibited.

Therefore, the hydrophobic material produced by the recombinant microorganism according to the present invention may be characterized by accumulating in the cell membrane. Examples of the hydrophobic material may be, but are not limited to, natural pigments, antioxidants, antibiotics, cosmetic additives, anticancer agents, food additives, and nutritional supplements.

In the present invention, the natural pigment is a pigment or an analogue thereof that is not artificially synthesized but is obtainable from nature, and examples thereof may include carotenoids, violacein, etc., and specific examples thereof may include, but are not limited to, lycopene, β-carotene, zeaxanthin, astaxanthin, proviolacein (PVIO), prodeoxyviolacein (PDVIO), deoxyviolacein (DVIO), violacein (VIO), and the like.

Examples of the antioxidant material may include, but are not limited to, quercetin, dihydroquercetin, kaempferol, dihydrokaempferol, astaxanthin, resveratrol, tocopherol, tocotrienol, coenzyme Q10, apigenin, and the like.

Examples of the cosmetic additive may include, but are not limited to, aloesin, vitamin A, ceramide, pantothenate, panthenol, lupeol, squalene, eucalyptol, valencene, and the like.

Examples of the food additive may include, but are not limited to, carminic acid, β-carotene, lycopene, and the like.

Examples of the nutritional supplement may include, but are not limited to, silymarin, lutein, vitamins, coenzyme-Q10, resveratrol, omega-3 polyunsaturated fatty acids, ubiquinone, glucosamine, luteolin, and the like.

In an embodiment of the present invention, it was confirmed that, by performing suppression, introduction, or overexpression of various genes as described above, the recombinant microorganism for producing a hydrophobic material according to the present invention was prepared and the overall ability thereof to produce the hydrophobic material was maintained or significantly improved, but that the cell-membrane engineering of the gene combination showing the most remarkable effect of enhancing production ability was different depending on the hydrophobic material to be produced.

Since the hydrophobic material exhibits the phenomenon of accumulation in the cell membrane, which is hydrophobic, the recombinant microorganism of the present invention subjected to cell-membrane engineering for increasing the cell membrane area, increasing the formation and secretion of outer membrane vesicles, and increasing the formation of inner membrane vesicles may exhibit increased ability to produce a hydrophobic material.

Therefore, the microorganism for producing a hydrophobic material subjected to cell-membrane engineering of the present invention may be constructed into a library through suppression, introduction, or overexpression of various gene combinations, and screening a strain showing high ability to produce a specific hydrophobic material using the library may be useful from aspects of cost, procedure, and time for the selection and development of a recombinant strain having increased ability to produce the hydrophobic material.

Therefore, yet another aspect of the present invention pertains to a microorganism library for producing a hydrophobic material obtained by performing cell-membrane engineering in a microorganism for producing a hydrophobic material through at least one among suppression of expression of a cell-morphology-related gene, suppression of expression of an outer-membrane-vesicle-related gene, and introduction or overexpression of an inner-membrane-vesicle-related gene.

Still yet another aspect of the present invention pertains to a method of screening a recombinant microorganism having increased ability to produce a specific hydrophobic material, which is subjected to cell-membrane engineering, including (a) constructing a microorganism library for producing a hydrophobic material by performing cell-membrane engineering in a microorganism for producing a hydrophobic material through at least one among suppression of expression of a cell-morphology-related gene, suppression of expression of an outer-membrane-vesicle-related gene, and introduction or overexpression of an inner-membrane-vesicle-related gene, and (b) selecting a recombinant microorganism having high ability to produce a specific hydrophobic material by culturing the microorganism for producing a hydrophobic material.

In the present invention, the microorganism library for producing a hydrophobic material having characteristics such as an increase in the cell membrane area, an increase in the formation and secretion of outer membrane vesicles, and/or an increase in the formation of inner membrane vesicles may be produced by performing cell-membrane engineering through suppression or overexpression of the related gene group using the phenomenon by which the hydrophobic material accumulates in the cell membrane, and based thereon, a recombinant strain having increased ability to produce a specific hydrophobic material may be screened.

In the present invention, the "microorganism library for producing a hydrophobic material" may be obtained by performing suppression of expression of the cell-morphology-related gene, suppression of expression of the outer-membrane-vesicle-related gene, and introduction or overexpression of the inner-membrane-vesicle-related gene, either alone or in any combination.

In the present invention, the cell-membrane engineering in step (a) may be additionally characterized in that expression of a lipid synthase gene is increased in the microorganism library for producing a hydrophobic material.

In the present invention, the library may include all of recombinant microorganisms in which the expression of cell-morphology-related genes alone or in any combination is suppressed.

In the present invention, the cell-morphology-related gene may include any gene involved in maintaining cell morphology.

In the present invention, any cell-morphology-related gene may be included without limitation, so long as it is a gene capable of increasing the cell area by modifying cell morphology upon suppression of expression thereof, and this gene may be easily selected by those skilled in the art depending on the type of recombinant microorganism that is used.

In the present invention, the cell-morphology-related gene may be, for example, a gene involved in cell division or a gene involved in synthesis or maintenance of a cytoskeleton/cell wall, but is not limited thereto.

In the present invention, the gene involved in cell division may be an endogenous gene encoding a prokaryote-derived enzyme group, such as cell division proteins (e.g. Fts proteins, etc.) or cell division inhibitors (e.g. MinC, MinD, etc.), but is not limited thereto.

In the present invention, the gene involved in synthesis or maintenance of the cytoskeleton/cell wall may be an endogenous gene encoding a prokaryote-derived enzyme group, such as penicillin-binding protein (PBP), cell-shape-determining protein (MreB, MreC, etc.), peptidoglycan D,D-transpeptidase (MrdA, PbpA, etc.), peptidoglycan glycosyltransferase (MrdB, etc.), cytoskeleton protein (RodZ, etc.), or the like, but is not limited thereto.

In the present invention, for example, when the recombinant microorganism used for preparing the library is *E. coli*, the cell-morphology-related gene may be selected from the group consisting of rodZ (cytoskeleton protein), ftsA (cell division protein), ftsB (cell division protein), ftsI (peptidoglycan D,D-transpeptidase), ftsL (cell division protein), ftsQ (cell division protein), ftsW (probable peptidoglycan glycosyltransferase), ftsZ (cell division protein), minD (septum site-determining protein), mrdA (peptidoglycan D,D-transpeptidase), mrdB (peptidoglycan glycosyltransferase), mreB (cell-shape-determining protein), mreC (cell-shape-determining protein), zipA (cell division protein), murE (UDP-N-acetylmuramoyl-L-alanyl-D-glutamate-2,6-diaminopimelate ligase), pbpC (penicillin-binding protein 1C), and combinations thereof, but is not limited thereto.

In the present invention, the library may include all of recombinant microorganisms in which the expression of outer-membrane-vesicle-related genes alone or in any combination is suppressed.

In the present invention, any outer-membrane-vesicle-related gene may be included without limitation, so long as it is a gene involved in the formation or secretion of outer membrane vesicles.

In the present invention, the outer-membrane-vesicle-related gene may be a gene that plays a role in maintaining the connection between the outer membrane and the inner membrane of the cell or the peptidoglycan layer of the cell.

In the present invention, the outer-membrane-vesicle-related gene may be an outer membrane/peptidoglycan structure maintenance-related gene, an outer-membrane protein expression gene, or a cell-membrane metabolic-network-related gene, but is not limited thereto.

In the present invention, the outer membrane/peptidoglycan structure maintenance-related gene may be a gene encoding a prokaryote-derived enzyme group that contributes to the maintenance of the outer membrane/peptidoglycan structure, such as lipoprotein (Lpp), Tol-Pal system protein (TolB, Pal, TolA, TolR, etc.), lipopolysaccharide core biosynthesis protein, lipopolysaccharide core heptosyltransferase, lipid A biosynthesis lauroyltransferase, or the like, but is not limited thereto.

In the present invention, the outer-membrane protein expression gene may be a gene encoding a prokaryote-derived enzyme group that contributes to the expression of the outer-membrane protein, such as outer-membrane protein A (OmpA), outer-membrane protein C (OmpC), outer-membrane protein F (OmpF), OprF (OmpA homologue), envelope protein (RagA, RagB, etc.), or the like, but is not limited thereto.

In the present invention, the cell-membrane metabolic-network-related gene may be a gene encoding a prokaryote-derived cell-membrane metabolic-network enzyme group, such as quinolone signal (PQS), anti-sigma-E factor, sigma factor H (AlgU), chaperone-protease (DegP), or the like, but is not limited thereto.

In the present invention, for example, when the recombinant microorganism is *E. coli*, the outer-membrane-vesicle-related gene may be selected from the group consisting of rseA (anti-sigma-E factor), rseB (sigma-E factor regulatory protein), rffD (UDP-N-acetyl-D-mannosamine dehydrogenase), rffC (dTDP-fucosamine acetyltransferase), rffA (dTDP-4-amino-4,6-dideoxygalactose transaminase), ompR (DNA-binding dual transcriptional regulator), gmhB (D-glycero-beta-D-manno-heptose-1,7-bisphosphate 7-phosphatase), lpxL (lipid A biosynthesis lauroyltransferase), lpxM (lipid A biosynthesis myristoyltransferase), ompA (outer-membrane protein), ompC (outer-membrane protein), rfaB (lipopolysaccharide 1,6-galactosyltransferase), rfaC (lipopolysaccharide heptosyltransferase 1), rfaD (ADP-L-glycero-D-manno-heptose-6-epimerase), rfaE (bifunctional protein HldE), rfaG (lipopolysaccharide core biosynthesis protein), rfaI (lipopolysaccharide 1,3-galactosyltransferase), rfaJ (lipopolysaccharide 1,2-glucosyltransferase), rfaK (lipopolysaccharide 1,2-N-acetylglucosaminetransferase), rfaP (lipopolysaccharide core heptose (I) kinase), rfaQ (lipopolysaccharide core heptosyltransferase), rfaY (lipopolysaccharide core heptose (II) kinase), rfbA (glucose-1-phosphate thymidylyltransferase 1), rffH (glucose-1-phosphate thymidylyltransferase 2), wzxE (ECA polysaccharide chain-length modulation protein), pnp (polyribonucleotide nucleotidyltransferase), tolA (colicin import membrane protein), tolB (Tol-Pal system periplasmic protein), tolC (outer-membrane protein), tolR (biopolymer transport protein), nlpI (lipoprotein), nlpD (murein hydrolase activator), ompF (outer-membrane pore protein), pal (peptidoglycan-associated outer membrane lipoprotein), degS (serine endoprotease), degP (serine endoprotease), tatC (sec-independent protein translocase protein), lpp (murein lipoprotein), and combinations thereof, but is not limited thereto.

In the present invention, the library may include all of recombinant microorganisms in which the expression of inner-membrane-vesicle-related genes alone or in any combination is suppressed.

In the present invention, any inner-membrane-vesicle-related gene may be included without limitation, so long as it is a gene involved in the formation of inner membrane vesicles.

In the present invention, any inner-membrane-vesicle-related gene may be selected and used without limitation, so long as it is a gene capable of improving the formation of inner membrane vesicles. In the present invention, when the recombinant microorganism for producing a hydrophobic material is a microorganism having no inner membrane vesicle system, another eukaryote- or prokaryote-derived inner membrane vesicle system gene that forms an inner membrane may be introduced to afford a library.

In the present invention, when the recombinant microorganism for producing a hydrophobic material inherently includes an inner membrane vesicle system, the inner-membrane-vesicle-related gene may be overexpressed, or another eukaryote- or prokaryote-derived inner membrane vesicle system gene may be additionally introduced.

In the present invention, the inner-membrane-vesicle-related gene may be a eukaryotic-cell-derived caveola system gene or a clathrin-epsin system gene, or may be a prokaryotic-cell-derived mgs-dgs system gene, and may more specifically be selected from the group consisting of cav1 (caveolin-1), cav2 (caveolin-2), cav3 (caveolin-3), EPN1 (epsin1), CLINT1 (epsinR), CLTC (clathrin heavy chain 1), CLTCL1 (clathrin heavy chain 2), CLTA (clathrin light chain A), CLTB (clathrin light chain B), AP180, AP2, almgs (1,2-diacylglycerol 3-glucosyltransferase), aldgs (1,2-diacylglycerol-3-glucose (1-2)-glucosyltransferase producing diglucosyldiacylglycerol), and combinations thereof, but is not limited thereto.

In the present invention, the microorganism library for producing a hydrophobic material may include recombinant microorganisms in which any one gene selected from the group consisting of cell-morphology-related genes, outer-membrane-vesicle-related genes, and inner-membrane-vesicle-related genes or any combination of these genes is suppressed, introduced, or overexpressed.

In the present invention, the microorganism library for producing a hydrophobic material may include a single genus or a single species of microorganisms, and may include a mixture thereof with a different genus or species of microorganisms.

In the present invention, the microorganism library for producing a hydrophobic material may include any microorganism selected from the group consisting of E. coli, Rhizobium, Bifidobacterium, Rhodococcus, Candida, Erwinia, Enterobacter, Pasteurella, Mannheimia, Actinobacillus, Aggregatibacter, Xanthomonas, Vibrio, Pseudomonas, Azotobacter, Acinetobacter, Ralstonia, Agrobacterium, Rhodobacter, Zymomonas, Bacillus, Staphylococcus, Lactococcus, Streptococcus, Lactobacillus, Clostridium, Corynebacterinum, Streptomyces, Bifidobacterium, Cyanobacterium, Cyclobacterium, and combinations thereof.

In the present invention, the microorganism library for producing a hydrophobic material may be imparted with at least one characteristic among an increase in the cell membrane area, an increase in the formation and secretion of outer membrane vesicles, and an increase in the formation of inner membrane vesicles.

EXAMPLES

A better understanding of the present invention may be obtained through the following examples. However, these examples are not to be construed as limiting the present invention, and it will be apparent to those skilled in the art that various modifications or alterations may be made within the spirit and scope of the present invention.

Example 1: Construction of Natural-Pigment-Producing Strain

Example 1-1: Construction of Carotenoid-Producing Strain

Carotenoids are responsible for red, orange, and yellow colors in the visible spectrum. Representative carotenoids are β-carotene, zeaxanthin, and astaxanthin, having orange, yellow, and red colors, respectively. Before construction of E. coli that produces three types of carotenoids, a strain producing lycopene as the precursor thereof was first constructed. Since E. coli is able to produce farnesyl diphosphate through the 1-deoxy-D-xylulose 5-phosphate production pathway, it is necessary to introduce three genes, namely crtE, crtB, and crtI, in order to produce lycopene, which is located upstream of the carotenoid synthesis pathway (FIG. 1). In order to prevent the accumulation of unnecessary precursors and to balance the metabolic flow, various combinations of expression levels of individual genes were screened. The expression level was regulated by altering the sequence of the 5' untranslated region (5' UTR) (FIG. 2A). A 5' UTR sequence library composed of a total of 16 5' UTR sequences was constructed for each gene using a UTR library designer program. Individual genes in which 16 different 5' UTR sequences were fused were combined and introduced into a pTac15K plasmid to construct a pLYC library. In order to construct the pLYC library, the pTac15K plasmid was first linearized through PCR amplification using primers of [SEQ ID NO: 1] and [SEQ ID NO: 2]. Next, crtE, crtB, and crtI genes were subjected to PCR amplification using primers of [SEQ ID NO: 3] and [SEQ ID NO: 4], [SEQ ID NO: 5] and [SEQ ID NO: 6], and [SEQ ID NO: 7] and [SEQ ID NO: 8], respectively, in a pCar184 plasmid (Choi et al., Appl. Environ. Microbiol. 2010, 76(10):3097-3105), and then cloned into the linearized pTac15k plasmid through Gibson assembly.

TABLE 1

Primers used in construction of lycopene-producing strains

| Name | Sequence | SEQ ID NO: |
|---|---|---|
| pTac15K plasmid-primer (Forward) | CTTGGCTGTTTTGGCGGATG | 1 |
| pTac15K plasmid-primer (Reverse) | TGTTTCCTGTGTGAAATTGTTATCCGCTC | 2 |
| crtE primer (Forward) | ATAACAATTT CACACAGGAA ACACGYTCMG CGGAAAGRAG CATCGWCCAT GTATCCGTTT ATAAGGACA | 3 |
| crtE primer (Reverse) | TTAACTGACGGCAGCGAGTT | 4 |
| crtB primer (Forward) | CGCTGCCGTC AGTTAAARCC TTGTTCAAAG GMSYATCTAG GATGAATAAT CCGTCGTTAC T | 5 |
| crtB primer (Reverse) | TTCGAACGGTTCTTAGAGCGGGCGCTGCCA | 6 |
| crtI primer (Forward) | GCTCTAAGAACCGTTCGAAWGSAGCRTMCAAGATGAAA CCAACTACGGTAAT | 7 |
| crtI primer (Reverse) | CGCCAAAACAGCCAAGTTAAATCAGATCCTCCAGC | 8 |

The constructed pLYC library was introduced into the *E. coli* WLGB-RPP strain developed in the prior study by the present research team, after which 200 colonies having a particularly dark color were selected from among colonies 10 times the size of the pLYC library and then subjected to test-tube culture, after which the produced lycopene was extracted, absorbance at 474 nm was measured, and the results thereof were compared. Among these, the top 10 strains were further cultured in a flask, and lycopene was produced in the greatest amount of 23.90 mg/L in the LYC79 strain.

Based on the selected LYC79 strain, strains producing β-carotene, zeaxanthin, and astaxanthin were constructed in the same way. First, a crtY gene for the production of β-carotene from lycopene, crtZ for the production of zeaxanthin from β-carotene, and BKT for the production of astaxanthin from zeaxanthin are additionally required. For each of these genes, a 5' UTR library composed of 16 different 5' UTR sequences was constructed and fused to the 5' end of the gene.

In order to construct a pBTC library, first, a pTrcCDFS plasmid was linearized through PCR amplification using primers of [SEQ ID NO: 9] and [SEQ ID NO: 10]. Also, crtY PCR-amplified using primers of [SEQ ID NO: 11] and [SEQ ID NO: 12] from the pCar184 plasmid was cloned into the linearized pTrcCDFS through Gibson assembly. For construction of a pZEA library, crtY and crtZ PCR-amplified using primers of [SEQ ID NO: 11] and [SEQ ID NO: 13] and primers of [SEQ ID NO: 14] and [SEQ ID NO: 15] from pCar184 were cloned into the linearized pTrcCDFS through Gibson assembly. In order to construct a pATX library, trCrBKT PCR-amplified using primers of [SEQ ID NO: 16] and [SEQ ID NO: 17] in the pAX1 plasmid (Park et al., Metab. Eng. 2018, 49:105-115) was inserted into the SalI/HindIII site of pZEA.

TABLE 2

Primers used for construction of strains producing β-carotene, zeaxanthin, and astaxanthin

| Name | Sequence | SEQ ID NO: |
|---|---|---|
| pTrcCDFS plasmid-primer (Forward) | 5'-TCTAGAGTCGACCTGCAG-3' | 9 |
| pTrcCDFS plasmid-primer (Reverse) | 5'-TCTGTTTCCTGTGTGAAATT-3' | 10 |
| crtY primer (Forward) | 5'-CAATTTCACA CAGGAAACAG ACCTTCCTCC AWAAGRAGCA TCMASTATGG GAGCGGCTAT G-3' | 11 |

TABLE 2-continued

Primers used for construction of strains producing β-carotene, zeaxanthin, and astaxanthin

| Name | Sequence | SEQ ID NO: |
|---|---|---|
| crtY primer1 (Reverse) | 5'-GCAGGTCGACTCTAGATTAACGATGAGTCGTCATAA-3' | 12 |
| crtY primer2 (Reverse) | 5'-TTAACGATGAGTCGTCATAA-3' | 13 |
| crtZ primer (Forward) | 5'-CATTATGACG ACTCATCGTT AAAGTACATC CGAMMGSAGC ATCCTTKATG TTGTGGATTT GGAATGC-3' | 14 |
| crtZ primer (Reverse) | 5'-GCAGGTCGACTCTAGATTACTTCCCGGATGC-3' | 15 |
| trCrBKT primer Forward) | 5'-AGACAGGTCGACKCCACCCCGCAAAGGAGSATCGKCRAT GGGTCCGGGCATC-3' | 16 |
| trCrBKT primer (Reverse) | 5'-AGACAGAAGCTTTTACGCCAGCGCCGC-3' | 17 |

Each of the constructed pBTC, pZEA, and pATX libraries was introduced into the LYC79 strain, and 20, 40, and 200 colonies were selected through visual inspection and then cultured in test tubes. The produced β-carotene, zeaxanthin, and astaxanthin were extracted with acetone, absorbance was measured at wavelengths of 473, 452, and 475 nm, and the production concentrations were compared. Here, since the color of astaxanthin cannot be distinguished from that of canthaxanthin, which is the precursor thereof, with the naked eye or through absorbance measurement, HPLC analysis was additionally performed on the top 50 strains based on the results of absorbance measurement. Flask culture was performed on 3, 5, and 10 strains, which produced β-carotene, zeaxanthin, and astaxanthin in the greatest amounts upon test-tube culture. The BTC1, ZEA20, and ATX68 strains showed the highest production of β-carotene (18.65 mg/L), zeaxanthin (12.67 mg/L), and astaxanthin (14.49 mg/L), respectively, and were selected as the final strains (FIGS. 2A to 2J).

1-2. Construction of Violacein-Analogue-Producing Strain

In addition to carotenoids, in order to complete the visible spectrum, violacein analogues were produced by the present research team. Violacein analogues are classified as bis-indole pigments, are produced from bacteria such as *Chromobacterium violaceum*, *Janthinobacterium lividum*, etc., and are known to have various pharmacological effects, such as anticancer effects. Therefore, the present research team constructed a biosynthesis pathway to produce four types of violacein analogues, namely prodeoxyviolacein, proviolacein, deoxyviolacein, and violacein (FIGS. 1 and 3A), and observed the colors of the materials produced therefrom (FIG. 3G). Since the present research team already constructed a strain overproducing tryptophan, which is a common precursor of violacein analogues, through previous studies (IND5 harboring pTacGEL), plasmids in which the pTacCDFS-vector-based violacein analogue biosynthesis pathway was introduced to the corresponding strain were transformed, thus preparing basic strains producing violacein analogues.

First, using a pTacCDFS plasmid as a basic vector, reverse PCR reaction was performed using primers of [SEQ ID NO: 18] and [SEQ ID NO: 19] to linearize the plasmid. Thereafter, a vioAB gene was split into two gene fragments and amplified. The first fragment was amplified using [SEQ ID NO: 20] and [SEQ ID NO: 21], and the second fragment was amplified using [SEQ ID NO: 22] and [SEQ ID NO: 23]. The two DNA fragments were cloned using the linearized plasmid and Gibson assembly to prepare a pTacCDFS-vioAB plasmid. Also, pTacCDFS-vioC, pTacCDFS-vioD, pTacCDFS-vioCD, and pTacCDFS-vioE plasmids were constructed using the same method. The vioC, vioD, vioCD, and vioF genes were subjected to PCR amplification using respective primer pairs [SEQ ID NO: 24] and [SEQ ID NO: 25], [SEQ ID NO: 26] and [SEQ ID NO: 27], [SEQ ID NO: 24] and [SEQ ID NO: 27], and [SEQ ID NO: 28] and [SEQ ID NO: 29]. The pPDVIO (pTacCDFS-vioABE) plasmid for the production of prodeoxyviolacein (PDVIO) was constructed as follows. Using the pTacCDFS-vioE plasmid as a template, the vioE gene fragment was amplified using primers of [SEQ ID NO: 30] and [SEQ ID NO: 31] and was then inserted into the SacI site in the pTacCDFS-vioAB plasmid. The pPVIO (pTacCDFS-vioABDE), pDVIO (pTacCDFS-vioABCE), and pVIO (pTacCDFS-vioABCDE) plasmids for the production of proviolacein (PVIO), deoxyviolacein (DVIO), and violacein (VIO), respectively, were constructed as follows. Respectively using pTacCDFS-vioC, pTacCDFS-vioD, and pTacCDFS-vioCD plasmids as templates, the gene fragments vioC, vioD, and vioCD were amplified using common primers of [SEQ ID NO: 32] and [SEQ ID NO: 31]. The amplified genes were inserted into the SacI site of the pTacCDFS-vioABE plasmid, thereby completing pDVIO (pTacCDFS-vioABCE), pPVIO (pTacCDFS-vioABDE), and pVIO (pTacCDFS-vioABCDE) plasmids.

TABLE 3

Primers used in construction of violacein-analogue-producing strains

| Name | Sequence | SEQ ID NO: |
|---|---|---|
| pTacCDFS plasmid primer (Forward) | 5'-TGGAATTCGAGCTCGGTACC-3' | 18 |
| pTacCDFS plasmid primer (Reverse) | 5'-TTCACACAGGAAACAGACCA-3' | 19 |
| vioAB primer (Forward) | 5'-CACACAGGAAACAGACCAATGAAGCATTCTTCCGATATCTGC-3' | 20 |
| vioAB_mid primer (Reverse) | 5'-GCCAGGCTTCGGAATCGAATG-3' | 21 |
| vioAB_mid primer (Forward) | 5'-CATTCGATTCCGAAGCCTGGC-3' | 22 |
| vioAB primer (Reverse) | 5'-GGTACCGAGCTCGAATTCCATTATCAGGCCTCTCTAGAAAGCTTTCC-3' | 23 |
| vioC primer (Forward) | 5'-CACACAGGAAACAGACCAATGAAAAGAGCAATCATAGTCGG-3' | 24 |
| vioC primer (Reverse) | 5'-GGTACCGAGCTCGAATTCCATTATCAGTTGACCCTCCCTATCTTG-3' | 25 |
| vioD primer (Forward) | 5'-CACACAGGAAACAGACCAATGAAGATTCTGGTCATCGGC-3' | 26 |
| vioD primer (Reverse) | 5'-GGTACCGAGCTCGAATTCCATTATCAGCGTTGCAGCGCGTAG-3' | 27 |
| vioE primer (Forward) | 5'-CACACAGGAAACAGACCAATGGAAAACCGGGAACCGCC-3' | 28 |
| vioE primer (Reverse) | 5'-GGTACCGAGCTCGAATTCCATTACTAGCGCTTGGCGGCGAAG-3' | 29 |
| vioE_frag primer (Forward) | 5'-CCTGATAATGGAATTCGAGCTGACTGCACGGTGCACCAATG-3' | 30 |
| vioE_frag primer (Reverse) | 5'-CAGGTCGACTCTAGAGGATCC-3' | 31 |
| vio_frag primer (Forward) | 5'-GCTAGTAATGGAATTCGAGCTGACTGCACGGTGCACCAATG-3' | 32 |

As for flask culture of the violacein-producing strains using glucose or glycerol as a carbon source, violacein was produced at a higher concentration when using glycerol as the carbon source, as shown in FIG. 3B. Accordingly, all violacein analogues utilized glycerol as a carbon source. From the strains constructed as above, 1.09 g/L of deoxyviolacein was produced when a vioABCE biosynthesis gene cluster (BGC) was introduced, and 1.36 g/L of violacein and 0.13 g/L of deoxyviolacein were produced when vioABCDE BGC was introduced (FIG. 3D). When vioABE BGC was introduced, prodeoxyviolacein was produced, and when vioABDE BGC was introduced, proviolacein was produced. Due to the absence of standard materials of proviolacein and prodeoxyviolacein, they were purified by fraction collector attached to HPLC and their concentrations were calculated based on the HPLC calibration tables.

The flask culture conditions were as follows. For carotenoid-producing strains, colonies were inoculated into 3 mL of a TB (terrific broth; 20 g of tryptone, 24 g of a yeast extract, 4 mL of glycerol, 0.017 M $KH_2PO_4$, and 0.072 M $K_2HPO_4$ per liter) medium supplemented with an appropriate concentration of antibiotics, followed by culture at 30° C. When $OD_{600}$ of the culture solution reached 1-2, 1 mL of the culture solution was subcultured in a 250 mL round-bottom flask containing 20 mL of a TB medium, and culture was continued until $OD_{600}$ reached 1-2. For violacein analogues, colonies were inoculated into 10 mL of an LB medium supplemented with an appropriate concentration of antibiotics, followed by culture overnight at 37° C. Thereafter, the prepared carotenoid or violacein-analogue culture solution was transferred to a 250 mL baffled flask containing 50 mL of an R/2 medium supplemented with 3 g/L of a yeast extract and 20 g/L of glycerol (with further addition of 3 g/L of $(NH_4)_2SO_4$ for violacein analogues), followed by culture at 30° C. and 200 rpm. The R/2 medium (pH 6.8) had the following composition (per liter): 2 g of $(NH_4)_2HPO_4$, 6.75 g of $KH_2PO_4$, 0.85 g of citric acid, 0.7 g of $MgSO_4 \cdot 7H_2O$, and 5 ml of a trace metal solution (TMS) [10 g of $FeSO_4 \cdot 7H_2O$, 2.25 g of $ZnSO_4 \cdot 7H_2O$, 1 g of $CuSO_4 \cdot 5H_2O$, 0.5 g of $MnSO_4 \cdot 5H_2O$, 0.23 g of $Na_2B_4O_7 \cdot 10H_2O$, 2 g of $CaCl_2 \cdot 2H_2O$, and 0.1 g of $(NH_4)_6Mo_7O_{24}$ per liter of 5 M HCl]. When $OD_{600}$ of the culture solution reached 0.6-0.8, 1 mM isopropyl β-D-1-thiogalactopyranoside (IPTG) was added to induce expression of a foreign gene. After induction, culture was carried out for 36 hours for carotenoids and 48 hours for violacein analogues.

After culture, the production amount was analyzed under the following conditions. For carotenoids, cells were collected by centrifuging 1 mL of the culture solution, the supernatant was removed, 1 mL of acetone was added thereto, and the material inside the cells was extracted through vigorous vortexing at 55° C. and 1,500 rpm. Cell debris in the extract was filtered using a centrifuge, thus obtaining a carotenoid extract of the supernatant. For violacein analogues, 50 μL of the culture solution (the volume of the culture solution that is added may be adjusted appropriately depending on the estimated concentration range; the amount of DMSO that is added is adjusted so that the total volume is 1 mL) was mixed with 950 μL of dimethylsulfoxide (DMSO), followed by vigorous vortexing at 40° C. and 1,500 rpm, thereby extracting materials inside and outside the cells. Thereafter, cell debris in the extract was filtered using a centrifuge in the same manner as above, thus obtaining a violacein analogue extract of the supernatant. Quantitative analysis of each extract was performed using HPLC. In the case of violacein analogues, LC-MS was performed due to the absence of a standard material (FIGS. 3E to 3F).

Example 2. Increased Production of Rainbow Pigments Through Cell Morphology Engineering Carotenoids having long carbon chains and violacein analogues having hydrophobic carbon rings are hydrophobic. Because of these properties, when carotenoids and violacein analogues are produced in E. coli, they accumulate inside the cell, particularly in the cell membrane, rather than being released out of the cell. Therefore, attempts have been made to increase the accommodation capacity by increasing the cell membrane area in order to produce the corresponding materials in larger amounts. To this end, an attempt was made to suppress the expression of genes responsible for a cell-membrane-related metabolic network. For suppression of expression of a target gene, a synthetic regulatory sRNA tool (Na et al., Nat. Biotechnol. 2013, 31(2):170-174) was utilized. As the expression suppression target, 16 genes involved in cell division and cell morphology maintenance were selected (Table 4). The expression suppression target genes were selected according to two criteria, the first criterion being genes involved in cell division (ftsABILQWZ, minD, zipA). Suppression of cell division is expected to change cell length (FIG. 4A). The second criterion is genes involved in cell-wall synthesis or maintenance (rodZ, mrdAB, mreBCE, murE). Since the cell wall determines the rod-shaped morphology of E. coli, suppressing the expression of the cell-wall-related gene is expected to change the cell morphology more spherically and irregularly (FIG. 4A). In the present example, gene targets regarded as the most effective were selected based on the above two criteria, but the scope of the invention is not necessarily limited thereto, and other genes corresponding to the above two criteria may also be utilized as targets.

TABLE 4

16 types of cell-morphology-related gene targets

| Gene | Protein function | Essentiality* | NCBI ID |
|---|---|---|---|
| rodZ | transmembrane component of cytoskeleton | NE | 946992 |
| ftsA | ATP-binding cell division protein involved in recruitment of FtsK to Z ring | E | 944778 |
| ftsB | cell division protein | E | 946033 |
| ftsI | transpeptidase involved in septal peptidoglycan synthesis | E | 944799 |
| ftsL | membrane bound cell division protein at septum containing leucine zipper motif | E | 944803 |
| ftsQ | membrane anchored protein involved in growth of wall at septum | E | 944823 |
| ftsW | integral membrane protein involved in stabilising FstZ ring during cell division | E | 946322 |
| ftsZ | GTP-binding tubulin-like cell division protein | E | 944786 |
| minD | membrane ATPase of the MinC-MinD-MinE system | E | 945741 |
| mrdA | transpeptidase involved in peptidoglycan synthesis | E | 945240 |
| mrdB | cell wall shape-determining protein | E | 945238 |
| mreB | cell wall structural complex MreBCD, actin-like component MreB | E | 948588 |
| mreC | cell wall structural complex MreBCD transmembrane component MreC | E | 947655 |
| zipA | cell division protein involved in Z ring assembly | E | 946869 |
| murE | UDP-N-acetylmuramoyl-L-alanyl-D-glutamate:meso-diaminopimelate ligase | E | 944791 |
| pbpC | fused transglycosylase and transpeptidase | NE | 947152 |

*E, a gene essential for E. coli cell growth when cultured in a minimal medium; NE, a gene that is not essential for E. coli cell growth when cultured in a minimal medium Most of the target genes were essential genes, so sRNA technology is required. In this experiment, testing was typically performed using a β-carotene-producing strain and a deoxyviolacein-producing strain, and the results thereof are shown in FIGS. 4B and 4C.

As seen in FIGS. 4A to 4J, 5A, and 5B, in the β-carotene-producing strain, when the expression of cell-membrane-related genes was suppressed, changes in cell morphology were observed, but the production amounts were decreased.

On the other hand, in the deoxyviolacein-producing strain, when the expression of the mrdB gene was suppressed, the production amount was increased significantly, and reached 1.37 g/L (25% increased production). When the expression of mrdB was suppressed, as expected, the cell length was shortened and the cell showed a more spherical shape, resulting in a decreased cell membrane area.

Example 3. Increased Production of Rainbow Pigments Through Formation of Inner Membrane Vesicles In order to further increase the amounts of rainbow pigments that are produced, the present research team tried to introduce inner membrane vesicles present in eukaryotic cell systems, whereby attempts were made to increase the production of materials accumulated in the membrane by enlarging the membrane area inside the cell while maintaining the volume of the cell itself (FIG. 4D). The introduced inner membrane vesicle gene borrowed from caveola, among eukaryotic inner membrane vesicle systems, caveola being responsible for the wrinkled shape of the Golgi body or vesicles. First, the cav1, cav2, or cav3 gene was introduced into the pTrc99A plasmid, and was then introduced into each of the β-carotene- and deoxyviolacein-producing strains, followed by flask culture. Although the caveola system of eukaryotes was borrowed in the present example, other eukaryote- or prokaryote-derived systems (eukaryotic clathrin-epsin system, prokaryotic mgs-dgs system, etc.) that form the inner membrane also fall within the scope of the present invention.

Each of cav1 [SEQ ID NO: 36], cav2 [SEQ ID NO: 37], and cav3 [SEQ ID NO: 38] genes was utilized after *E. coli* codon optimization of the gene sequence derived from *Homo sapiens*. In order to construct a pTrc99A-cav1 plasmid, the cav1 gene was inserted into the EcoRI and BamHI sites of the pTrc99A plasmid. For the construction of pTrc99A-cav2 and pTrc99A-cav3, the cav2 and cav3 genes were inserted into the NcoI and BamHI sites of the pTrc99A plasmid, respectively. For the construction of a pTrc99A-cav12 plasmid (containing both cav1 and cav2), the cav2 gene was amplified using primers of [SEQ ID NO: 33] and [SEQ ID NO: 34], and was then inserted into the BamHI and PstI sites of the pTrc99A-cav1 plasmid. For the construction of pTrc99A-cav23 and pTrc99A-cav13, the cav3 gene was amplified using primers of [SEQ ID NO: 35] and [SEQ ID NO: 34], and was then inserted into the PstI site of each of pTrc99A-cav2 and pTrc99A-cav1 plasmids. For the construction of a pTrc99A-cav123 plasmid, the amplified cav3 gene was inserted into the PstI site of the pTrc99A-cav12 plasmid.

TABLE 5

Introduced inner-membrane-vesicle-related gene and primer sequences

| Name | Sequence | SEQ ID No: |
|---|---|---|
| cav2 primer (Forward) | TTAACTGGATCCTTTCACACAGGAAACAGACCATGGGGCTTGAGACTGAGAAG | 33 |
| cav primer (Reverse) | CATCCGCCAAAACAGCCAAGCTTG | 34 |
| cav3 primer (Forward) | TTAACTCTGCAGTTTCACACAGGAAACAGACCATGATGGCCGAAGAGCATACC | 35 |
| cav1 | atgtctgggg gcaaatacgt agactcggag ggacatctct acaccgttcc catccgggaa cagggcaaca tctacaagcc caacaacaag gccatggcag acgagctgag cgagaagcaa gtgtacgacg cgcacaccaa ggagatcgac ctggtcaacc gcgaccctaa acacctcaac gatgacgtgg tcaagattga ctttgaagat gtgattgcag aaccagaagg gacacacagt tttcacggca tttggaaggc cagcttcacc accttcactg tgacgaaata ctggttttac cgcttgctgt ctgccctctt tggcatcccg atggcactca tctgggcat ttacttcgcc attctctctt tcctgcacat ctgggcagtt gtaccatgca ttaagagctt cctgattgag attcagtgca ccagccgtgt ctattccatc tacgtccaca ccgtctgtga cccactcttt gaagctgttg ggaaaatatt cagcaatgtc cgcatcaact tgcagaaaga aatataa | 36 |
| cav2 | atggggcttgagactgagaaggcagatgtccaactgttcatggatgatga ttcttactcacatcactcaggactggaatatgcagatccagaaaagtttgc ggactccgaccaggatcgtgaccccaccgcttaaatagtcacttaaaact gggctttgaagatgtgatcgcggagcctgtcacaactcatagtttcgataa ggtttggatttgctcacacgcattatttgaaatttcaaagtacgttatgta taagttccttactgtattttggccatccctcttgcctttatcgcaggaat cctgttcgctaccttgagttgtctgcacatttggattcttatgccattcgt aaagacatgccttatggtgttgccatcagtgcaaaccatctggaagtccgt cactgatgtaattattgcccctttgtgtacatctgtgggccgctgcttttc gagcgtctcacttcaattgtcgcaggattaa | 37 |

TABLE 5-continued

Introduced inner-membrane-vesicle-related gene and primer sequences

| Name | Sequence | SEQ ID No: |
|---|---|---|
| cav3 | atgatggccgaagagcataccgatcttgaagctcaaattgtaaaggatatt cattgtaaggaaattgacttggttaatcgtgatcctaagaacatcaacgag gatatcgttaaggtagacttcgaggatgttattgcagaacctgttggaaca tacagtttcgacggtgtctggaaggtgtcgtacactacgtttaccgttagt aagtattggtgctatcgcttactgtccactctgttgggtgtccccttgct ttgctttggggattcctgttcgcgtgtatctcttttttgccatatttgggct gtcgttccatgtattaaatcgtacttaattgagattcaatgtatctctcat atttatagtctttgtatccgcacgttctgtaatcccctttttgcggccttg gggcaggtgtgctcaagtattaaggttgtacttcgtaaggaggtctaa | 38 |

The plsBC gene of *E. coli* was amplified in order to further supply cell-membrane lipids, the amount of which may be insufficient due to the formation of the inner membrane structure. To this end, the pTrc99A-plsBC plasmid was first constructed. Therefore, the plsB and plsC genes were amplified using primers of [SEQ ID NO: 39] and [SEQ ID NO: 40] and primers of [SEQ ID NO: 41] and [SEQ ID NO: 42] from the genomic DNA of *E. coli*, respectively, and then inserted into the PstI and HindIII sites of the pTrc99A plasmid using Gibson assembly. After cleaving the constructed plasmid using PstI and HindIII restriction enzymes, the plsBC gene fragment was isolated and inserted into the PstI and HindIII sites of the pTrc99A-cav1 plasmid, thereby constructing a pTrc99A-cav1-plsBC plasmid.

TABLE 6

Primers used for cell-membrane lipid synthase gene amplification

| Name | Sequence | SEQ ID NO: |
|---|---|---|
| plsB primer (Forward) | CTAGAGTCGACCTGCAGTTTCACACAGGAAACAGACCATGTC CGGCTGGCCACGA | 39 |
| plsB primer (Reverse) | TCTGTTTCCTGTGTGAAATTACCCTTCGCCCTGCGTC | 40 |
| plsC primer (Forward) | GAAGGGTAATTTCACACAGGAAACAGACCATGCTATATATCT TTCGTCTTATTATTACC | 41 |
| plsC primer 1 (Reverse) | CCGCCAAAACAGCCAAGCTTTTAAACTTTTCCGGCGGC | 42 |

Based on the results thereof, when both the β-carotene- and deoxyviolacein-producing strains expressed the cav1 gene, the production amounts thereby were greatly increased, to 21.89 mg/L and 1.28 g/L, respectively. Particularly in the deoxyviolacein-producing strain, it was found that, when two or three of cav1, cav2, and cav3 were expressed together, the production amount was drastically reduced (FIGS. 4E and 4F). Based on the results of observing whether the formation of inner membrane vesicles was induced in the control group (FIGS. 4G and 4I) and the cav1-overexpressing strain (FIGS. 4H and 4J), TEM (top of each figure) and SEM (bottom of each figure) showed that the inner membrane vesicles were successfully formed in the cav1-overexpressing strain without a great difference in cell morphology from the control group.

Example 4. Increased Production of Rainbow Pigments Through Increase in Formation and Secretion of Outer Membrane Vesicles In order to further increase the amounts of rainbow pigments that were produced, the present research team tried to release the rainbow pigments accumulated in cells through vesicles by increasing the expression of the inherent outer-membrane-vesicle-forming gene of a microorganism (FIG. 6A). It has been reported that, for expression of outer membrane vesicles, it is important not to express specific genes but to suppress the expression of genes that play a role in maintaining the connection between the outer membrane and the inner membrane of the cell or the peptidoglycan layer of the cell. Therefore, the present research team also tried to suppress the expression intensity of a total of 26 target genes using a sRNA-based target gene expression suppression system. The selected 26 expression suppression gene targets were as follows: rseA, rseB, rffD, rffC, rffA, ompR, gmhB, lpxL, ompA, ompC, rfaB, rfaC, rfaD, rfaE, rfaG, rfaI, rfaJ, rfaK, rfaP, rfaQ, rfaY, rfbA, rffH, wzxE, and pnp (Table 7). Here, (1) gene targets involved in maintaining the outer membrane/peptidoglycan structure were rfaG, rffA, rffC, rffD, rffH, etc., (2) gene targets corresponding to expression of the outer-membrane protein were ompR, ompC, etc., and (3) gene targets involved in expression of anti-sigma factor in a cell-membrane metabolic network were rseA, rseB, etc. In the present example, the gene targets regarded as the most effective were selected based on the above three criteria, but the scope of the invention is not necessarily limited thereto, and other genes corresponding to the above three criteria may also be utilized as targets. The results of measurement of the amounts of β-carotene and deoxyviolacein that were produced when expression of the corresponding gene targets was suppressed are shown in FIGS. 6B and 6C. When the expression of rfaD, rffD, and rfaQ was suppressed, the amounts of β-carotene that was produced were effectively increased to 26.43, 24.21, and 20.29 mg/L, respectively. In particular, when the expression of rfaI and rfaQ was suppressed, the amount of deoxyviolacein that was produced was greatly increased. In the strain in which the expression of rfaI was suppressed, deoxyviolacein was produced in an amount of 1.74 g/L.

Based on the results of SEM and TEM of the BTC1 strain introduced with sRNA suppressing expression of rffD and rfaD and the DVIO strain introduced with sRNA suppressing expression of rfaI, a significant increase in the formation and secretion of outer membrane vesicles was observed (FIGS. 6D to 6F). In particular, when the DVIO strain introduced with sRNA suppressing expression of rfaI was cultured, it was found that the outer membrane vesicles, deoxyviolacein, and cell debris aggregated on the wall of the flask. The micrographs thereof are shown in FIG. 7E.

TABLE 7

26 gene targets involved in outer membrane vesicles for increasing formation and secretion of outer membrane vesicles

| Target gene | Protein function | Essentiality* | NCBI ID |
|---|---|---|---|
| rseA | Inhibitor of σE | NE | 947053 |
| rseB | Inhibitor of σE | E | 947054 |
| rffD | Genes involved in ECA pathway | E | 948977 |
| rffC | Genes involved in ECA pathway | NE | 948298 |
| rffA | Genes involved in ECA pathway | NE | 948296 |
| ompR | Response regulator for ompC and ompF | NE | 947913 |
| gmhB | Genes involved in LPS pathway | NE | 944879 |
| lpxL | Genes involved in LPS pathway | NE | 946216 |
| lpxM | Genes involved in LPS pathway | NE | 945143 |
| ompA | Outer-membrane protein A | NE | 945571 |
| ompC | Outer-membrane protein | NE | 946716 |
| rfaB | Genes involved in LPS pathway | E | 948144 |
| rfaC | Genes involved in LPS pathway | NE | 948136 |
| rfaD | Genes involved in LPS pathway | NE | 948134 |
| rfaE | Genes involved in LPS pathway | NE | 947548 |
| rfaG | LPS core biosynthesis; glucosyl transferase | NE | 948149 |
| rfaI | Genes involved in LPS pathway | NE | 948143 |
| rfaJ | Genes involved in LPS pathway | E | 948142 |
| rfaK | Genes involved in LPS pathway | E | 948147 |
| rfaP | Genes involved in LPS pathway | E | 948150 |
| rfaQ | Genes involved in LPS pathway | E | 948155 |
| rfaY | Genes involved in LPS pathway | E | 948145 |
| rfbA | Genes involved in ECA pathway | NE | 945154 |
| rffH | Genes involved in ECA pathway | E | 948299 |
| wzxE | Inner membrane translocase for a component of ECA | NE | 948294 |
| pnp | Polynucleotide phosphorylase | NE | 947672 |

*E, a gene essential for *E. coli* cell growth when cultured in a minimal medium; NE, a gene that is not essential for *E. coli* cell growth when cultured in a minimal medium Example 5. Confirmation of Synergistic Effect of Cell Morphology Modification and Vesicle Formation Based on the above results, the synergistic effect was evaluated through combinations of the genetically engineered targets having the best effect in each category.

sRNA plasmid cloning for simultaneous multiple target gene knockdown was performed as follows. The first sRNA fragment was PCR-amplified using primers of [SEQ ID NO: 43] and [SEQ ID NO: 44], and the plasmid containing the second sRNA fragment was linearized through reverse PCR using primers of [SEQ ID NO: 45] and [SEQ ID NO: 46]. The two sRNA-containing fragments thus obtained were combined using Gibson assembly to complete a sRNA plasmid for double knockdown. In order to insert *E. coli* plsBC into the sRNA-containing plasmid, the plsBC gene was PCR-amplified using primers of [SEQ ID NO: 47] and [SEQ ID NO: 48] and using the pTrc99A-plsBC plasmid as a template, and was then inserted into the SphI site of the sRNA-containing plasmid. In order to insert the cav1 gene into the sRNA-containing plasmid, the gene was inserted into the SphI site of the sRNA-containing plasmid using primers of [SEQ ID NO: 47] and [SEQ ID NO: 49] and using the pTrc99A-cav1 plasmid as a template.

TABLE 8

Primers used for cell-membrane lipid synthase gene amplification

| Name | Sequence | SEQ ID NO: |
|---|---|---|
| sRNA primer 1 (Forward) | CACTAGATCTCAAATGTGCTGGAATTCTAACACCGTGCGTG | 43 |

TABLE 8-continued

Primers used for cell-membrane lipid synthase gene amplification

| Name | Sequence | SEQ ID NO: |
|---|---|---|
| sRNA primer 1 (Reverse) | CCTTATAAATCAAACATGTGCGGCGAATTGGGTACCTATAAAC | 44 |
| sRNA primer 2 (Forward) | GCACATGTTTGATTTATAAGGG | 45 |
| sRNA primer 2 (Reverse) | CAGCACATTTGAGATCTAGTGG | 46 |
| ptrc primer (Forward) | ATGTGACAGCTTATCGCATGCTTGACAATTAATCATCCGG | 47 |
| plsC primer 2 (Reverse) | CCTGGGTTTACCTAGGCATGCTTAAACTTTTCCGGCGGCTTC | 48 |
| cav1 primer (Reverse) | CCTGGGTTTACCTAGGCATGCTTATATTTCTTTCTGCAAGTTG | 49 |

In the β-carotene-producing strain, when the expression of the cell-membrane metabolic-network-related gene of Example 2 was suppressed, an increase in the production amount was not confirmed, so the combination of overexpression of the inner membrane vesicle expression gene (cav1) of Example 3 and suppression of expression of the outer membrane vesicle expression target genes (rfaD, rffD, rfaD) of Example 4 was applied. First, the expression of different combinations of three outer membrane vesicle expression target genes was suppressed. When the expression of rfaD and rffD was simultaneously suppressed, the amount of β-carotene that was produced was greatly increased to 34.2 mg/L (FIG. 6B). Although the cav1 gene was additionally overexpressed to form inner membrane vesicles in the corresponding strain, the production amount was decreased (FIG. 6G).

In the deoxyviolacein-producing strain, combinations of two or three among the cell-membrane metabolic-network target gene (mrdB) of Example 2, the inner membrane vesicle expression gene (cav1) of Example 3, and the outer membrane vesicle expression target gene (rfaI) of Example 4 were expressed, and the amount of deoxyviolacein that was produced was observed. Based on the results thereof, in the strain in which expression of rfaI was suppressed and cav1 was overexpressed, deoxyviolacein was produced in an amount of 1.9 g/L, which is evaluated to be the greatest (FIG. 6H).

Based on the results of SEM and TEM of the BTC1 strain introduced with sRNA suppressing expression of rffD and rfaD and introduced with cav1-plsBC and the DVIO strain introduced with sRNA suppressing expression of rfaI and introduced with cav1, an increase in the formation and secretion of outer membrane vesicles and an increase in the formation of inner membrane vesicles were simultaneously observed (FIGS. 6I and 6J).

Example 6. Application of Cell Membrane Expansion Strategy for Production of Different Rainbow Pigments The strategy used in the Examples above was applied to other hydrophobic pigments in order to show the versatility of the present invention. Accordingly, the cell-membrane engineering strategy, which was the most effective for increased production of β-carotene, which is a representative carotenoid compound, and deoxyviolacein, which is a representative violacein analogue compound, was applied to the remaining rainbow pigments in each category. In the increased production of β-carotene, the formation of inner membrane vesicles through simultaneous overexpression of cav1 and plsBC genes and the formation of outer membrane vesicles through suppression of expression of rffD and rfaD genes were effectively improved, and thus this strategy was applied to ZEA20 and ATX68, which are strains producing zeaxanthin and astaxanthin. Based on the test results thereof, the formation of inner membrane vesicles decreased the production of zeaxanthin and slightly increased the production of astaxanthin. On the other hand, the formation of outer membrane vesicles increased the production of both zeaxanthin and astaxanthin (18.38 mg/L in FIG. 7H, and 22.69 mg/L in FIG. 7I, respectively). For violacein analogues, simultaneous expression of inner membrane vesicles and outer membrane vesicles led to the highest production of deoxyviolacein, so the effects thereof were evaluated by expressing inner membrane vesicles and outer membrane vesicles separately or simultaneously. Accordingly, three strategies were tested: (1) rfaI knockdown for overexpression of outer membrane vesicles, (2) cav1 overexpression for overexpression of inner membrane vesicles, and (3) both rfaI knockdown and cav1 overexpression. Proviolacein and violacein were produced in the greatest amounts when the inner membrane vesicles and the outer membrane vesicles were simultaneously expressed (402 mg/L in FIG. 7K and 2.84 g/L in FIG. 7L). However, prodeoxyviolacein was produced in the greatest amount when only the outer membrane vesicles were expressed (341 mg/L in FIG. 7J). Here, commercially available reagents for proviolacein and prodeoxyviolacein could not be purchased, so the corresponding materials were purified and then quantified using a fraction collector connected to an HPLC apparatus.

Example 7. Development of Fed-Batch Fermentation Process for High-Efficiency Production of Rainbow Pigments Fed-batch fermentation was performed in a 6.6 L fermenter using the recombinant E. coli strains constructed in the Examples above. Fed-batch fermentation was carried out under the following conditions. The carotenoid-producing strains were cultured in a 6.6 L fermenter (BioFlo 320, Eppendorf) supplemented with 1.6 L of an R/2 medium (pH 6.95) containing 30 g/L of glucose or glycerol, 3 g/L of a yeast extract, and antibiotics. The violacein-analogue-producing strains were cultured in a 6.6 L fermenter (BioFlo 320, Eppendorf) supplemented with 1.95 L of an R/2 medium (pH 6.8) containing 20 g/L of glucose or glycerol, 3 g/L of a yeast extract, 3 g/L of $(NH_4)_2SO_4$, and antibiotics. For the carotenoid-producing strains, colonies were inoculated into 3 mL of a TB medium containing an appropriate concentration of antibiotics, followed by culture at 30° C. For the violacein analogues, colonies were inoculated into 10 mL of an LB medium supplemented with an appropriate concentration of antibiotics, followed by culture overnight at 37° C. Thereafter, the prepared carotenoid or violacein-analogue culture solution was transferred to a 250 mL baffled flask containing 50 mL of an R/2 medium supplemented with 3 g/L of a yeast extract and 20 g/L of glycerol or glucose (with further addition of 3 g/L of $(NH_4)_2SO_4$ for violacein analogues), followed by culture at 30° C. and 200 rpm. Here, culture was continued until $OD_{600}$ reached 3-4, and the culture solution was inoculated in the fermenter. The pH was maintained at 6.8 using a 28% (v/v) aqueous ammonia solution, and the temperature was maintained at 30° C. The dissolved oxygen (DO) value was maintained at 40% by providing air at 2 L/min, automatically adjusting a stirring speed up to 1,000 rpm, and increasing oxygen flow. Nutritional supply was carried out using a pH-stat strategy, and the feed was automatically allowed to flow when the pH value exceeded 7 for carotenoids and 6.85 for violacein derivatives. The feed solution for production of carotenoids had the following components per 1 L: 800 g of glucose or 817 g of glycerol, 6 mL of a trace metal solution, and 12 g of $MgSO_4 \cdot 7H_2O$. The feed solution for production of violacein derivatives had the following components per 1 L: 650 g of glucose or 800 g of glycerol, 6 mL of a trace metal solution, 85 g of $(NH_4)_2SO_4$, and 8 g of $MgSO_4 \cdot 7H_2O$. After inoculation, when $OD_{600}$ reached 20-30, expression of a foreign protein was induced using 1 mM IPTG.

The concentration of each pigment obtained through fed-batch culture of recombinant E. coli, which showed the greatest production ability for each pigment, was as follows:
 i) astaxanthin-producing recombinant microorganism ATX68 (pWAS, rffD, rfaD expression suppression): 322 mg/L (FIG. 8A);
 ii) β-carotene-producing recombinant microorganism BTC1 (pWAS, rffD, rfaD expression suppression): 343 mg/L (FIG. 8B);
 iii) zeaxanthin-producing recombinant microorganism ZEA20 (pWAS, rffD, rfaD expression suppression): 218 mg/L (FIG. 8C);
 iv) proviolacein-producing recombinant microorganism PVIO (pWAS, rfaI expression suppression & cav1 overexpression): 1.3 g/L (FIG. 8D);
 v) prodeoxyviolacein-producing recombinant microorganism PDVIO (pWAS, rfaI expression suppression): 0.855 g/L (FIG. 8E);
 vi) violacein-producing recombinant microorganism VIO (pWAS, rfaI expression suppression & cav1 overexpression: 6.69 g/L of violacein produced (1.39 g/L of deoxyviolacein also produced) (FIG. 8F); and
 vii) deoxyviolacein-producing recombinant microorganism DVIO (pWAS, rfaI expression suppression & cav1 overexpression): 11.3 g/L (FIG. 8G).

All seven hydrophobic pigments were capable of being produced at high concentrations using the E. coli strains developed according to the present invention, indicating that the present invention is effective for high-efficiency production of hydrophobic materials.

INDUSTRIAL APPLICABILITY

According to the present invention, a cell-membrane engineering method is broadly classified into three methods: first, cell morphology is modified by suppressing expression of a gene involved in cell division; second, an inner membrane structure is enlarged by introducing or overexpressing a gene involved in expression of inner membrane vesicles; and third, outer membrane vesicles are overproduced by suppressing expression of a target gene involved in cell-membrane metabolism in order to express outer membrane vesicles.

These three methods, when used alone or in combination, exhibit a synergistic effect, which is useful for producing an insoluble hydrophobic material with high efficiency. The recombinant microorganism for high-efficiency production of carotenoids or violacein analogues developed through the method of screening a recombinant microorganism having high ability to produce a hydrophobic material according to the present invention is useful as a microorganism for producing a natural pigment. Moreover, the natural pigment production technology developed in the present invention achieves a remarkable increase in production ability. Therefore, the present invention can be effectively applied to the preparation of a recombinant strain for the efficient production of a variety of industrially and medically useful metabolites and to the establishment of an efficient preparation method.

Although specific embodiments of the present invention have been disclosed in detail as described above, it will be obvious to those skilled in the art that the description is merely of preferable exemplary embodiments and is not to be construed as limiting the scope of the present invention. Therefore, the substantial scope of the present invention will be defined by the appended claims and equivalents thereof.

What is claimed is:

1. A recombinant bacterium, obtained by engineering a hydrophobic-pigment-producing bacterium by: i) rfaD gene encoding ADP-L-glycero-D-manno-heptose-6-epimerase and rffD gene encoding UDP-N-acetyl-D-mannosamine dehydrogenase are suppressed, ii) rfaI gene encoding lipopolysaccharide 1,3-galactosyltransferase is suppressed, and cav1 gene encoding caveolin-1 is introduced or overexpressed, or iii) rfaD gene and rffD gene are suppressed and cav1 gene is introduced or overexpressed, and the engineered bacterium is increasingly capable of producing a hydrophobic pigment.

2. The recombinant bacterium according to claim 1, wherein the recombinant bacterium is further engineered by performing suppression of a gene selected from the group consisting of rodZ, ftsA, ftsB, ftsI, ftsL, ftsQ, ftsW, ftsZ, minD, mrdA, mrdB, mreB, mreC, zipA, murE, pbpC, and combinations thereof.

3. The recombinant bacterium according to claim 1, wherein the bacterium is *Escherichia coli, Rhizobium, Rhodococcus, Candida, Erwinia, Enterobacter, Pasteurella, Mannheima, Actinobacillus, Aggregatibacter, Xanthomonas, Vibrio, Pseudomonas, Azotobacter, Acinetobacter, Ralstonia, Agrobacterium, Rhodobacter, Zymomonas, Bacillus, Staphylococcus, Lactococcus, Streptococcus, Lactobacillus, Clostridium, Corynebacterium, Streptomyces, Bifidobacterium, Cyanobacterium,* or *Cyclobacterium.*

4. The recombinant bacterium according to claim 1, wherein the hydrophobic pigment is selected from the group consisting of astaxanthin, beta-carotene, zeaxanthin, proviolacein, prodeoxyviolacein, deoxyviolacein, and violacein.

5. The recombinant bacterium according to claim 1, wherein the hydrophobic pigment is a carotenoid pigment, and expression of rffD and rfaD genes have been suppressed in the recombinant bacterium.

6. The recombinant bacterium according to claim 1, wherein the hydrophobic pigment is violacein or an analogue thereof, and expression of an rfaI gene has been suppressed and a cav1 gene has been introduced or overexpressed in the recombinant bacterium-bacteria.

7. A method of preparing a hydrophobic pigment, comprising:
producing a hydrophobic pigment by culturing the recombinant bacterium according to claim 1; and
recovering the produced hydrophobic pigment.

8. The method according to claim 7, wherein the culturing is carried out in fed-batch culture.

* * * * *

UNITED STATES PATENT AND TRADEMARK OFFICE
CERTIFICATE OF CORRECTION

PATENT NO. : 12,134,793 B2
APPLICATION NO. : 17/515614
DATED : November 5, 2024
INVENTOR(S) : Sang Yup Lee et al.

Page 1 of 1

It is certified that error appears in the above-identified patent and that said Letters Patent is hereby corrected as shown below:

In the Specification

Column 1, Line 21, "589 SeqListing_ST25.txt" should be -- "589_SeqListing_ST25.txt" --.

Column 4, Line 13, "P 0.05" should be -- $P \geq 0.05$ --.

Column 5, Line 23, "6l" should be -- 6I --.

Column 15, Line 6, "promoter (may" should be -- promoter Φ may --.

Column 16, Line 55, "2p" should be -- 2µ --.

Column 20, Lines 34-35, "*Corynebacterinum*" should be -- *Corynebacterium* --.

Column 26, Lines 3-4, "*Corynebacterinum*" should be -- *Corynebacterium* --.

Column 30, Line 43, "vioF" should be -- vioE --.

In the Claims

Claim 3, Column 61, Line 36, "*Mannheima*" should be -- *Mannheimia* --.

Claim 6, Column 62, Line 29, "bacterium-bacteria" should be -- bacterium --.

Signed and Sealed this
Twenty-second Day of April, 2025

Coke Morgan Stewart
*Acting Director of the United States Patent and Trademark Office*